(12) United States Patent
Ascher et al.

(10) Patent No.: US 6,531,465 B1
(45) Date of Patent: Mar. 11, 2003

(54) ANTIBACTERIAL CEPHALOSPORINS

(75) Inventors: Gerd Ascher, Kundl (AT); Johannes Ludescher, Breitenbach (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/861,838

(22) Filed: May 21, 2001

Related U.S. Application Data

(63) Continuation of application No. 09/357,194, filed on Jul. 20, 1999, now abandoned, which is a continuation of application No. 08/952,244, filed as application No. PCT/EP96/02023.

(30) Foreign Application Priority Data

| May 11, 1995 | (AT) | ............................................. 794/95 |
| Jun. 12, 1995 | (AT) | ............................................. 992/95 |
| Apr. 17, 1996 | (AT) | ............................................. 698/96 |
| Apr. 23, 1996 | (AT) | ............................................. 733/96 |

(51) Int. Cl.$^7$ .................... C07D 501/24; A61K 31/545; A61K 31/546; A61P 31/04
(52) U.S. Cl. ....................... 514/200; 514/203; 514/204; 514/205; 514/206; 514/208; 540/215; 540/222; 540/224; 540/225; 540/226; 540/229
(58) Field of Search ............................... 540/215, 222, 540/224, 225, 226, 229; 514/200, 203, 204, 205, 206, 268

(56) References Cited

U.S. PATENT DOCUMENTS

| 3,945,888 A | 3/1976 | Takahashi et al. |
| 3,987,039 A | 10/1976 | Yoshioka et al. ....... 260/243 C |
| 3,997,528 A | 12/1976 | Yoshioka et al. ....... 260/243 C |
| 4,053,469 A | 10/1977 | Yoshioka et al. ............. 544/21 |
| 4,101,658 A | 7/1978 | Yoshioka et al. ........... 424/246 |
| 4,463,172 A | * 7/1984 | Horii .......................... 540/226 |

FOREIGN PATENT DOCUMENTS

| FR | 2191881 | * 2/1974 |
| FR | 2220248 | 10/1974 |
| FR | 2248845 | 5/1975 |
| IE | 37209 | 12/1972 |

OTHER PUBLICATIONS

Chemical Abstracts, vol. 88, No. 17—Apr. 24, 1978 Abstract No. 121203u of JP 5L/083865.
Chemical Abstracts, vol. 92, No. 9—Mar. 3, 1980 Abstract No. 76491f of JP 54/070294.
Chemical Abstracts, vol. 85, No. 7—Aug. 16, 1976 Abstract No. 46704r of JP 50/131982.
Chemical Abstracts, vol. 84, No. 11—Mar. 15, 1976 Abstract No. 74282z of JP–A–07593990.
Chemical Abstracts, vol. 84, No. 7—Feb. 16, 1976 Abstract No. 44095y of JP 50/083391.
Chemical Abstracts, vol. 84, No. 5—Feb. 2, 1976 Abstract No. 31096z of JP 50/076085.
Chemical Abstracts, vol. 83, No. 1—Jul. 7, 1975 Abstract No. 10104q of JP 49/124091.
Chemical Abstracts, vol. 83, No. 25—Dec. 22, 1975 Abstract No. 206299b of JP 50/013389.
Derwent Abstract No. 06630V Shionogi—7/72 of NL 7309511.
Derwent Abstract No. 31030W Shionogi—Oct. 25, 1973 of DT 2450618.
Derwent Abstract No. 77150W Shionogi—Jun. 20, 1975 of BE 830492.
Derwent Abstract No. 51915B Takeda—Nov. 9, 1977 of J5 04070294.
Derwent Abstract No. 65706V Shionogi—Feb. 28, 1973 of NL74022776.
Derwent Abstract No. 46456W Takeda—Dec. 20, 1973 of DT 2458695.
Derwent Abstract No 91780X Takeda—May 12, 1975 of NL 7605032.
Lilly—Derwent Abstract—Patent No. NL–7217421—Dec. 23, 1971 of NL 7217421.
Derwent Abstract No. 61602Y Takeda—Jan. 1, 1976 of J5–2083865.
Derwent Abstract No. 40302U Lilly—Dec. 20, 1972 of DT–2262500.
Derwent No. 16829W Takeda—Mar. 3, 1973 of J4–9124091.
Derwent No. 56269W Takeda—Jun. 8, 1973 of J5–0013389.
Derwent No. 68060W Shionogi—Oct. 31, 1973 of J5–0076085.
Derwent No. 82371W Shionogi—Nov. 28, 1973 of J5–83391.
Derwent No. 85221Y Shionogi—Apr. 5, 1974 of J5–0131982.
Sugawara, et al. Chem. Pharm. Bull., vol. 27, 2544–2546 (1979).
Sugawara, et al. Chem. Pharm. Bull., vol. 28, 2116–2128 (1980).

* cited by examiner

*Primary Examiner*—Mark L. Berch
(74) *Attorney, Agent, or Firm*—Gabriel Lopez

(57) ABSTRACT

A compound of formula $$\text{AcNH} \begin{array}{c} S \\ \diagup \diagdown \\ N \\ \diagdown \diagup \\ O \end{array} \begin{array}{c} \\ \text{CH}=\text{N}-R_2 \\ \text{COOR}_1 \end{array} \quad I$$

wherein Ac, $R_1$ and $R_2$ have various meanings, a process for a preparation thereof and its use as a pharmaceutical, i.e. as antibacterial agent.

17 Claims, No Drawings

ANTIBACTERIAL CEPHALOSPORINS

Continuation of Ser. No. 09/357,194, Jul. 20, 1999, abandoned, which is a continuation of Ser. No. 08/952,244, Oct. 29, 1997, abandoned, which is a 371 of PCT/EP96/02023, Oct. 5, 1996.

The present invention relates to antibacterial compounds which are 7-acylamino-3-(imino)methyl cephalosporins.

Particularly the present invention provides a compound of formula

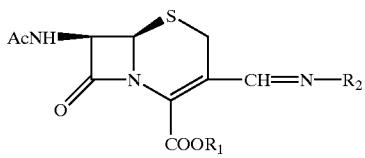

I wherein
$R_1$ denotes hydrogen or an ester moiety,
$R_2$ denotes a group of formula

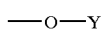

IIa

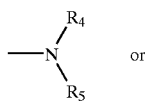

IIb or

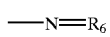

IIc wherein
Y denotes hydrogen, alkyl, alkenyl, acyl, carbamoyl or aryl
$R_4$ denotes hydrogen, alkyl, alkenyl, cycloalkyl, aryl, acyl or heterocyclyl
$R_5$ denotes hydrogen, alkyl, alkenyl, cycloalkyl, aryl, heterocyclyl, or a group of formula

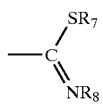

IId

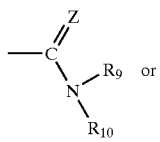

IIe

IIf wherein
$R_7$ denotes alkyl or aryl
$R_8$ denotes hydrogen, cycloalkyl or alkyl
$R_9$ denotes hydrogen or alkyl
$R_{10}$ denotes hydrogen, alkyl, hydroxy, amino, phenyl, alkenyl, cycloalkyl, aryl, heterocyclyl or a group of formula

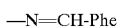

wherein Phe denotes aryl $R_9$ and $R_{10}$ together with the nitrogen atom denote heterocyclyl,
Z denotes oxygen, sulphur or N—$R_{13}$, wherein
$R_{13}$ denotes hydrogen, alkyl or cycloalkyl
$R_{11}$ denotes hydrogen, alkyl, aryl, cycloalkyl or heterocyclyl, or
$R_4$ and $R_5$ together with the nitrogen atom denote heterocyclyl,
$R_6$ denotes heterocyclyl, and
Ac denotes
(i) a group

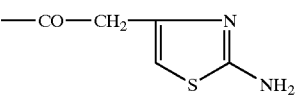

(ii) a group of formula

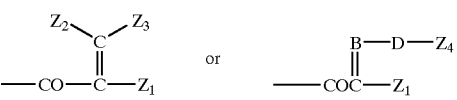

wherein
B denotes N or CH
$Z_1$ denotes aryl, cycloalkyl, 1,4-cyclohexadienyl or heterocyclyl
$Z_2$ denotes hydrogen, alkyl or —$CH_2COOZ_5$, wherein
$Z_5$ denotes hydrogen, alkyl or cycloalkyl
$Z_3$ denotes hydrogen or alkyl
$Z_4$ denotes hydrogen or an organic radical
D denotes oxygen or $CH_2$.

A subgroup of the invention comprises any of the individual groups of significances mentioned therein.

$R_1$ may be hydrogen or an ester moiety. An ester moiety includes alkyl, preferably $C_{1-6}$alkyl; arylalkyl, for example benzyl, alkoxybenzyl, such as 4-methoxybenzyl; indanyl, phthalidyl, alkoxymethyl, e.g. methoxymethyl; ($C_{1-6}$) alkanoyloxy($C_{1-6}$)alkyl, ($C_{1-6}$)alkoxycarbonyl-oxy($C_{1-6}$) alkyl, glycyloxymethyl, phenylglycyloxymethyl, (5-methyl-2-oxo-1,3-dioxolen4-yl)methyl and ester moieties which form with the COO— group a physiologically hydrolysable and acceptable ester, e.g. such known to be hydrolysable ester groups in the field of cephalosporins. A compound of formula I may thus be in the form of an physiologically-hydrolysable and -acceptable ester. By physiologically-hydrolysable and -acceptable esters as used herein is meant an ester in which the COO— group is esterified and which is hydrolysable under physiological conditions to yield an acid which is itself physilogically tolerable at dosages to be administered. The term is thus to be understood as defining regular pro-drug forms. An ester moiety may be preferably a group which is easily hydrolysable under physiological conditions. Such esters may be administered preferably orally. Parenteral administration may be indicated if the ester per se is an active compound or, if hydrolysis occurs in the blood.

Y may be preferably hydrogen, unsubstituted alkyl or alkyl substituted by e.g. hydroxy or, preferably the residue of a carboxylic acid. The residue of a carboxylic acid includes the residue of a carboxylic acid in free form or in salt form, of a carboxylic acid ester and of a carboxylic acid amide. The carboxylic acid is, for example, a $C_{1-7}$ carboxylic acid, preferably a $C_{1-5}$ aliphatic carboxylic acid, an alkyl part thereof including lower alkyl. The alkoxy group of a carboxylic acid ester includes $C_{1-6}$, preferably $C_{1-4}$alkoxy. Alkyl is preferably lower alkyl. The alkyl group is preferably unsubstituted or substituted by carboxylic acid residues.

$R_4$ may be preferably hydrogen or alkyl, for example lower alkyl.

$R_5$ may be preferably hydrogen; unsubstituted alkyl; alkyl substituted for example by oxo, alkyl or halogenated alkyl; amino; one or several fold substituted heterocyclyl; or a group of formulae IId, IIe, IIf. Heterocyclyl includes unsaturated or saturated heterocyclyl having, e.g. 5 or 6 ring members and, for example, 1 to 3 hetero atoms, such as N, O, S, preferably N, or condensed heterocyclyl, such as benzothiazolyl.

$R_4$ and $R_5$ together with the nitrogen atom may be heterocyclyl, having preferably 5 or 6 ring members and having preferably 1 to 3 heteroatoms, for example N atoms; which may be unsubstituted heterocyclyl; or one or several fold substituted heterocyclyl, for example by oxo, amino, alkyl.

$R_6$ may be saturated or unsaturated heterocyclyl; having preferably 5 or 6 ring members and having for example 1 or 2 nitrogen hetero atoms; for example unsubstituted heterocyclyl; or one or several fold substituted heterocyclyl, for example by amino, alkyl or thiono.

$R_7$ may be preferably alkyl.

$R_8$ may be preferably alkyl or cycloalkyl.

$R_9$ may be preferably hydrogen or lower alkyl.

$R_{13}$ may be preferably alkyl.

$R_{10}$ may be preferably hydrogen; aryl; alkenyl; cycloalkyl; unsubstituted alkyl; substituted alkyl, for example by hydroxy, halogen, heterocyclyl, such as pyridyl, amino, for example N(alkyl)$_2$ or N$^+$(alkyl)$_3$; or a group

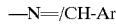
—N=/CH-Ar wherein Ar denotes heterocyclyl; unsubstituted aryl; or substituted aryl, for example by hydroxy or alkoxy; preferably aryl which may be preferably phenyl.

$R_9$ and $R_{10}$ together with the nitrogen atom may be heterocyclyl having preferably 5 or 6 ring members and 1 to 3 hetero atoms such as N, S, O, for example N, O; preferably saturated heterocyclyl. Heterocyclyl includes unsubstituted heterocyclyl, or substituted heterocyclyl, for example by acyl, formyl, alkyl, for example lower alkyl. Examples include pyrrolidine, morpholine, piperazine, preferably piperazine.

$R_{11}$ may be preferably hydrogen; unsubstituted alkyl; substituted alkyl, for example by aminoalkyl, diaminoalkyl, triaminoalkyl; aryl, such as dihydroxyphenyl; cycloalkyl; or unsubstituted heterocyclyl; or substituted heterocyclyl, for example by alkyl, thiono heterocyclyl; heterocyclyl having preferably 5 or 6 ring members and 1 to 3 hetero, preferably N atoms.

If not otherwise stated therein any carbon containing group may contain up to 20 carbon atoms, e.g. alkyl includes $C_{1-20}$, e.g. $C_{1-8}$ alkyl. Lower alkyl includes e.g. $C_{1-4}$alkyl, preferably $C_{1-2}$alkyl. Alkenyl includes $C_{2-20}$, e.g. $C_{2-8}$ alkenyl. Lower alkenyl includes e.g. $C_{3-5}$alkenyl, preferably $C_3$alkyl. Cycloalkyl includes, for example, $C_{3-6}$Cycloalkyl, particularly $C_3$, $C_5$ or $C_6$cycloalkyl. Alkyl, alkenyl and cycloalkyl include unsubstituted alkyl, alkenyl and cycloalkyl; and, substituted alkyl, alkenyl and cycloalkyl, for example, by halogen, a sulphonic acid derivative, such as SO$_3$H, CF$_3$, hydroxy, alkoxy, acyl, alkylamino, pyridyl. Cycloalkyl is preferably unsubstituted. Acyl includes $C_{1-12}$, e.g. $C_{1-6}$acyl, particularly $C_{1-4}$acyl. Acyl includes unsubstituted acyl and substituted acyl, for example, by hydroxy, alkoxy, amino. Aryl includes phenyl. Aryl may be unsubstituted aryl or substituted aryl, for example by alkyl, alkoxy, acyl, halogen, hydroxy, unprotected or protected amino. Alkoxy includes alkoxy wherein the alkyl part is as defined above.

Heterocyclyl includes heterocyclyl having 5 or 6 ring members and 1 to 3 nitrogen, sulphur and/or oxygen hetero atoms including, for example, condensed heterocyclyl, such as for example benzthiazolyl. Heterocyclyl includes further unsubstituted hetercyclyl and substituted heterocyclyl, for example by oxo, alkoxy, hydroxy, thiono, mercapto, alkylthio, imino, alkylamino, alkylimino, amino, halogen, acyl, CF$_3$, CHO, alkyl, cycloalkyl.

Carbamoyl includes the carbamoyl group or carbamoyl having alkyl and aryl residues.

$Z_1$ denotes unsubstituted cycloalkyl, 1,4-cyclohexadienyl, heterocyclyl or aryl; and one or several fold substituted cycloalkyl, 1,4-cyclohexadiene, heterocyclyl or aryl; for example by carboxyl, amino, nitro, cyano, lower alkyl, lower alkoxy, hydroxy, halogen, —CO—N(Z$_5$Z$_6$), —N(Z$_6$)—COOZ, Z$_6$CO—, Z$_6$OCO—, Z$_6$COO—.

$Z_2$ denotes hydrogen; CH$_2$COOZ$_5$; unsubstituted lower alkyl; one or several fold substituted lower alkyl, for example by carboxyl, amino, nitro, cyano, lower alkyl, lower alkoxy, hydroxy, halogen, —COZ$_5$Z$_6$, —N(Z$_6$)—COOZ$_7$, Z$_6$CO—, Z$_6$OCO— or Z$_6$COO—.

$Z_3$ denotes hydrogen or lower alkyl.

$Z_4$ denotes hydrogen or an organic radical; preferably hydrogen; lower alkyl; cycloalkyl; aralkyl; acyl; carboxyalkyl; Z$_6$CO—, —C(Z$_7$Z$_8$)COOZ$_6$ or, preferably in the case that $Z_1$ in group

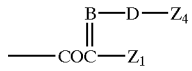

denotes a group 2-amino-thiazol-4yl or 2-amino-thia-3,5-diazol-4yl, $Z_4$ denotes a group of formula

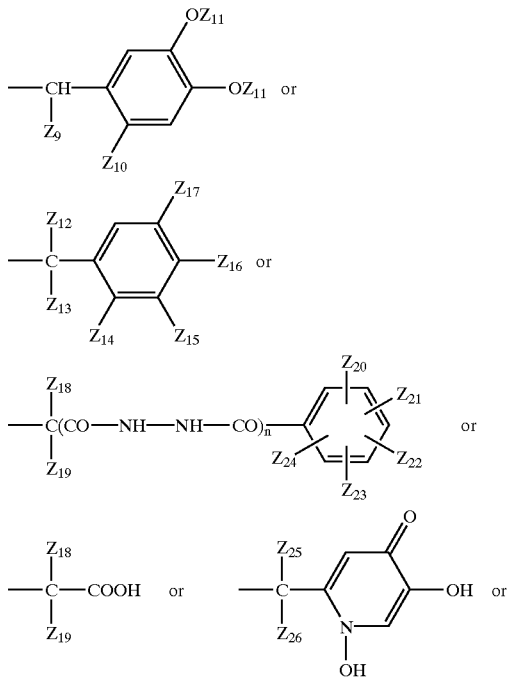

-continued

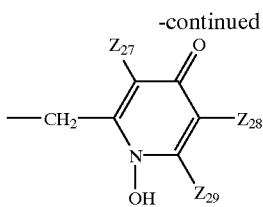

wherein
$Z_9$ and $Z_{10}$ independently of one another denote hydrogen or protected or unprotected carboxyl
$Z_{11}$ denotes hydrogen or acetyl,
$Z_{12}$ denotes unprotected or protected carboxyl,
$Z_{13}$ denotes hydrogen or methyl,
$Z_{14}$ denotes hydrogen; chloro; unprotected or protected carboxyl; methyl; isopropyl; hydroxy; methoxy; acetoxy,
$Z_{15}$ and $Z_{16}$ denote independently from one another hydrogen, hydroxy, methoxy, ethoxy, 2-methoxyethoxymethoxy, acetoxy, chloroacetoxy, butanoyloxy, methansulfonyloxy, p-toluenesulfonyloxy, amino, acetylamino, benzyloxycarbonylamino or methansulfonyl; or,
$Z_{15}$ and $Z_{16}$ denote together ethylendioxy or carbonyldioxy,
$Z_{17}$ denotes hydrogen, hydroxy, acetoxy, methyl, methoxy, chloroacetoxy, with the proviso, that not all of $Z_{14}$, $Z_{15}$, $Z_{16}$ and $Z_{17}$ denote hydrogen,
$Z_{18}$ and $Z_{19}$ denote independently of one another hydrogen or methyl,
$Z_{20}$, $Z_{21}$, $Z_{22}$, $Z_{23}$ and $Z_{24}$ denote independently of one another hydrogen, halogen or hydroxy,
$Z_{25}$ and $Z_{26}$ denote independently from one another hydrogen; $C_{1-5}$alkyl; unsubstituted phenyl; or substituted phenyl,
$Z_{27}$ denotes unsubstituted lower alkyl; or substituted lower alkyl,
$Z_{28}$ and $Z_{29}$ denote independently of one another hydrogen or hydroxy, and
n denotes 0 or 1,
$Z_5$ denotes hydrogen, alkyl, preferably lower alkyl,
$Z_6$ and $Z_7$ independently of one another denote hydrogen or alkyl, preferably lower alkyl,
$Z_6$ and $Z_7$ together with the carbon atom denote cycloalkyl, and
$Z_5$ and $Z_6$ together denote cycloalkyl.
$Z_4$ may be selected from the following groups:

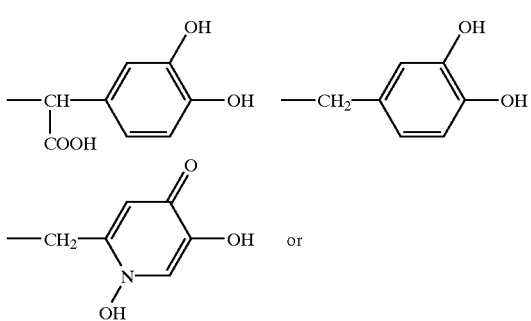

-continued

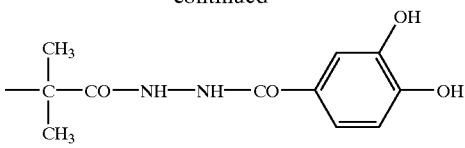

For example, Ac may denote a group of formula

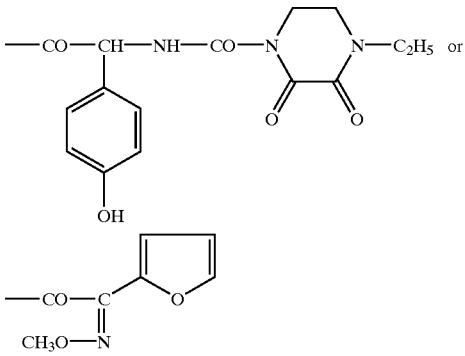

Preferably Ac denotes a compound of formula

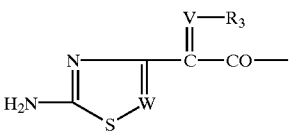

wherein
W denotes CH or N
V denotes CH or N—O and
$R_3$ denotes hydrogen, acyl, carboxyl, alkyl.
The configuration of $R_3$ in group of —C=V—$R_3$ may be syn [(Z)] and anti [(E)] and is preferably syn [(Z)].
If $R_3$ denotes alkyl, $R_3$ includes unsubstituted alkyl or substituted alkyl, for example by halogen, carboxyl. Preferably W denotes CH.
In another aspect the present invention provides a compound of formula

IA

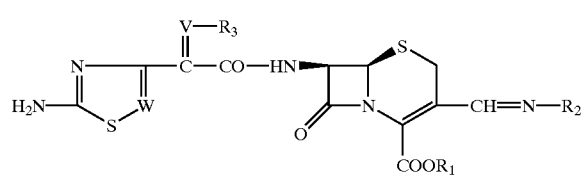

wherein
W denotes CH or N
V denotes CH or N—O
$R_1$ denotes hydrogen or an ester moiety,
$R_2$ denotes a group of formula IIa

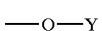

-continued

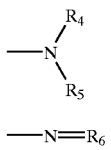  IIb

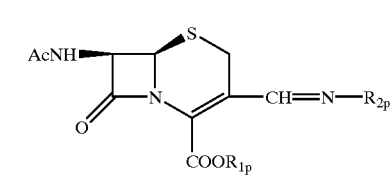  Ip wherein
Y denotes hydrogen; unsubstituted lower alkyl; or substituted lower alkyl, by the residue of a carboxylic acid, a carboxylic acid ester or a carboxylic acid amide,
$R_4$ denotes hydrogen, phenyl, cycloalkyl or lower alkyl
$R_5$ denotes hydrogen, lower alkyl, heterocyclyl or a group of formulae wherein
$R_{1p}$ is the same as $R_1$ in formula I,
Ac is as defined in formula I,
$R_{2p}$ denotes a group of formulae —$OY_p$  or  IIap

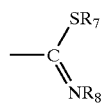  IId

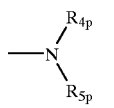  IIbp

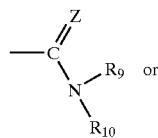  IIe wherein
$Y_p$ is the same as Y in formula IA,
$R_{4p}$ is the same as $R_4$ in formula IA, and
$R_{5p}$ denotes hydrogen, cycloalkyl, lower alkyl or a group of formula

  IIf

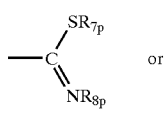  IIdp

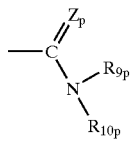  IIep wherein
$R_7$ denotes lower alkyl
$R_8$ denotes hydrogen, cycloalkyl or lower alkyl
$R_9$ denotes hydrogen or lower alkyl,
$R_{10}$ denotes hydrogen, hydroxy; amino; phenyl; alkenyl; cycloalkyl; heterocyclyl; unsubstituted alkyl; substituted alkyl, by $CF_3$, OH, alkoxy, carboxyl, halogen, amino, monoalkylamino, dialkylamino, trialkylamino, pyridyl or a a sulfonic acid residue; a group of formula

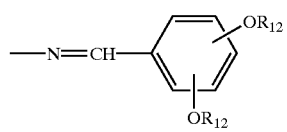

wherein
$R_{12}$ denotes hydrogen or lower alkyl,
Z denotes oxygen, sulphur, or N—$R_{13}$, wherein
$R_{13}$ denotes hydrogen or lower alkyl, and
$R_{11}$ denotes hydrogen; dihydroxyphenyl; cycloalkyl; heterocyclyl; unsubstituted lower alkyl; substituted lower alkyl by pyridyl or monoalkylamino, dialkylamino or trialkylamino; and,
$R_4$ and $R_5$ and/or $R_9$ and $R_{10}$ independently of one another together with the nitrogen denote heterocyclyl,
$R_6$ denotes heterocyclyl, and
$R_3$ denotes hydrogen; acyl; carboxyl; unsubstituted alkyl; substituted alkyl by halogen or carboxyl.

In another aspect the present invention provides a compound of formula wherein
$R_{8p}$ is the same as $R_8$ in formula IA,
$Z_p$ is the same as Z in formula IA,
$R_{9p}$ is the same as $R_9$ in formula IA,
$R_{7p}$ denotes methyl,
$R_{10p}$ denotes hydrogen, lower alkyl or hydroxy, and
$R_{4p}$ and $R_{5p}$ and/or $R_{9p}$ and $R_{10p}$ independently of one another together with the nitrogen denote heterocyclyl, and
a compound of formulae IIbp, IIdp and IIep denote any tautomeric form, in free form, or, where such a form exists, in form of an acid addition salt, inner salt, quaternary salt or hydrate thereof.

In another aspect the present invention provides a compound of formula

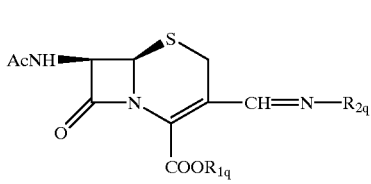  Iq wherein
Ac is as defined in formula I $R_{1q}$ is he same as $R_1$ in formula IA, and
$R_{2q}$ denotes a group of formula

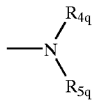    IIaq or

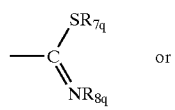    IIbq wherein
$Y_q$ is the same as Y in formula IA,
$R_{4q}$ is the same as $R_4$ in formula IA, and
$R_{5q}$ denotes hydrogen, cycloalkyl, lower alkyl or a group of formulae

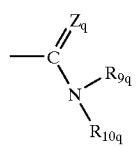    IIdq or

IIeq wherein
$R_{7q}$ is the same as $R_7$ in formula IA,
$R_{8q}$ is the same as $R_8$ in formula IA,
$Z_q$ is the same as Z in formula IA,
$R_{9q}$ is the same as $R_9$ in formula IA,
$R_{10q}$ denotes hydrogen, lower alkyl or hydroxy, and
$R_{4q}$ and $R_{5q}$ and/or $R_{9q}$ and $R_{10q}$ independently of one another together with the nitrogen denote heterocyclyl, and a compound of formulae IIbp, IIdp and IIep denote any tautomeric form, in free form, or, where such a form exists, in form of an acid addition salt, inner salt, quaternary salt or hydrate thereof.

In a further aspect the present invention provides a compound of formula

Is

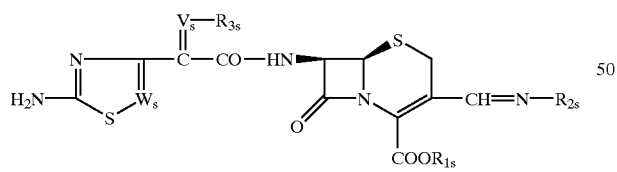

wherein
$R_{1s}$ is the same as $R_1$ in formula IA,
$V_s$ is the same as V in formula IA,
$W_s$ is the same as W in formula IA
$R_{3s}$ denotes hydrogen, lower acyl; unsubstituted alkyl; substituted lower alkyl, by carboxyl and/or fluoro; and
$R_{2s}$ denotes a group of formula —$OY_s$    IIas

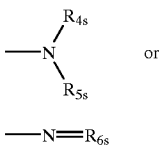    IIbs or

—N=$R_{6s}$    IIcs wherein
$Y_s$ denotes hydrogen; unsubstituted lower alkyl; or substituted alkyl by carboxyl,
$R_{4s}$ denotes hydrogen or lower alkyl, and
$R_{5s}$ denotes hydrogen; saturated or unsaturated, unsubstituted heterocyclyl having 5 or 6 ring members and 1 to 3 nitrogen hetero atoms; saturated or unsaturated one or several fold substituted heterocyclyl by oxo, lower alkyl, amino or $CF_3$, having 5 or 6 ring members and 1 to 3 nitrogen hetero atoms; benzothiazolyl; or a group of formula

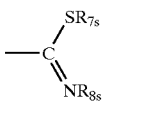    IIds

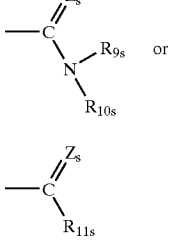    IIes or

IIfs wherein
$Z_s$ is the same as Z in formula I,
$R_{7s}$ denotes lower alkyl,
$R_{8s}$ denotes hydrogen, cycloalkyl or lower alkyl,
$R_{9s}$ denotes hydrogen or lower alkyl,
$R_{10s}$ denotes hydrogen; phenyl; allyl; cycloalkyl; unsubstituted alkyl; substituted alkyl by $CF_3$, dialkylamino, trialkylamino, hydroxy, pyridyl or $SO_3H$, and
$R_{11s}$ denotes hydrogen; pyridyl; cycloalkyl; unsubstituted lower alkyl; substituted lower alkyl by pyridyl or trialkylamino; saturated or unsaturated heterocyclyl having 5 or 6 ring members and 1 to 3 nitrogen hetero atoms; or one or several fold substituted heterocyclyl by lower alkyl and/or thiono, having 5 or 6 ring members and 1 to 3 nitrogen hetero atoms;
$R_{4s}$ and $R_{5s}$ together with the nitrogen atom denote heterocyclyl selected from saturated, unsubstituted heterocyclyl having 5 or 6 ring members and 1 or 2 nitrogen hetero atoms; saturated, one or several fold substituted heterocyclyl by oxo or lower alkyl, having 5 or 6 ring members and 1 or 2 nitrogen hetero atoms; and/or
$R_{9s}$ and $R_{10s}$ together with the nitrogen atom denote saturated, unsubstituted heterocyclyl having 5 or 6 ring members and 1 or 2 nitrogen and/or oxygen hetero atoms; unsaturated, one or several fold substituted heterocyclyl by CHO or lower alkyl, having 5 or 6 ring members and 1 or 2 nitrogen and/or oxygen hetero atoms.

In another aspect the present invention provides a compound of formula $$\text{IA}$$

wherein

W denotes CH or N

V denotes CH or N—O $R_1$ denotes hydrogen or an ester moiety, and $R_2$ denotes a group of formula —N($R_4R_5$)   IIb wherein
$R_4$ is as defined in claim 1 and
$R_5$ denotes a group of formula $$\text{IIe}$$

wherein
Z denotes —N—$R_{13}$, wherein
$R_{13}$ is as defined in claim 1, and
$R_9$ and $R_{10}$ together with the nitrogen atom denote heterocyclyl which is a piperazinyl.

In another aspect the present invention provides a compound selected from

7-[[(2-amino-4-thiazolyl)-(Z)-(hydroxyimino)acetyl] amino]-3-[[(aminoininomethyl)hydrazono]methyl]-3-cephem-4-carboxylic acid (compound of Example 2), 7-[[(2-amino-4-thiazolyl)-(Z)-(hydroxyimino)acetyl]-amino]-3-[[(piperazinoiminomethyl)hydrazono]methyl]-3-cephem-4-carboxylic acid (compound of Example 96)

7-[[(5-Amino-1,2,4-thiadiazol-3-yl)-(Z)-(fluormethoxyimino)acetyl]amino]-3-[[(piperazinoiminomethyl)hydrazono]methyl]-3-cephem-4-carboxylic acid (compound of Example 139).

A compound of formulae I, IA, $I_p$, $I_q$, $I_s$, IVi, IVa and VIa may exist in equilibrium with tautomeric forms. The present invention includes a compound of formulae I, IA, $I_p$, $I_q$, $I_s$ IVi, IVa and VIa in any tautomeric form in which it may exists.

In another aspect the present invention provides a process for the production of a compound of formula I by reaction of a compound of formula $$\text{II}$$

wherein Ac is as defined in formula I and
a) either
α) $R_b$ denotes hydroxy and $R_c$ and $R_d$ together form a bond, or
β) $R_d$ denotes hydrogen, a cation, an ester forming group or a silyl group, and $R_b$ and $R_c$ together denote oxo, in free form or in form of an acid addition salt with a group of formula $H_2N—R_2$   IV wherein $R_2$ is as defined in formula I, or
b) reacting a compound of formula $$\text{VI}$$

wherein $R_1$ and $R_2$ are as defined in formula I, with a compound of formula

Ac-X'   VII wherein Ac is as defined in formula I and X' denotes a leaving group.

If desired reactive groups may be protected with protecting groups, which may be, or, which are split off under the reaction conditions, or after termination of the reaction described above. A compound of formula I wherein $R_1$ denotes hydrogen may be converted into a compound of formula I, wherein $R_1$ denotes an carboxylic acid ester group. A compound of formula I may be isolated from the reaction mixture in conventional manner.

Process a) may be carried out as follows:

A compound of formula III in a solvent which is inert under the reaction conditions, such as water, a mixture of water and a lower alcohol and/or dioxane, or a dipolar aprotic solvent, for example dimethylformamide or dimethylsulfoxide, optionally mixed with an alcohol or water is reacted with a compound of formula IV at a temperature of about −20 to 50° C. An optimal pH may be adjusted by addition of an inorganic or organic acid or base. A compound of formula I thus obtained may be isolated in conventional manner, for example by addition of an anti-solvent or by chromatographic techniques.

Process b) may be carried out as follows:

The reaction may be carried out as conventional, e.g. a compound of formula VI may be reacted with a compound of formula VII in a solvent, for example dissolved or suspended in a mixture of acetone/water, for example at room temperature.

A reactive group may be protected, preferably by silyl protecting group technology. Suitable solvents include solvents which are inert under the reaction conditions, such as chlorinated hydrocarbons, nitrites, such as acetonitrile, ethers, such as tetrahydrofuran or a mixture of such solvents. Further suitable solvents include dipolar aprotic solvents, e.g. N,N-dimethylformamide. Protecting groups may be split off in conventional manner.

A starting compound of formula II may, for example, be obtained by a) reaction of a compound of formula

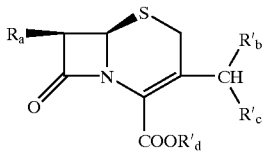
IIIc wherein either
α) $R_a$ denotes a salt of —$NH_2$ with an inorganic or organic acid, $R'_b$ denotes hydroxy, and $R'_c$ and $R'_d$ denote together a bond, or
β) $R_a$ denotes $NH_2$, $R'_d$ denotes hydrogen and $R'_b$ and $R'_c$ together denote oxo, with a silylation agent and, a compound obtained in step a) of formula

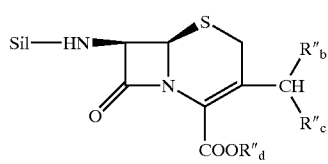
IIId wherein Sil denotes a silyl group and either
α) $R''_b$ denotes —OSil and $R''_c$ and $R''_d$ together denote a bond
β) $R''_c$ denotes Sil and $R''_b$ and $R''_c$ together denote oxo is acylated either directly in the reaction mixture or after isolation from the reaction mixture.

Acylation may be carried out in conventional manner.
A compound of formula IIc may be obtained
a) for the production of a compound of formula

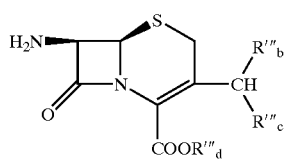
IIIe which is an the form of a salt of an inorganic or organic acid and wherein $R'''_b$ denotes hydroxy and $R'''_c$ and $R'''_d$ together denote a bond, reacting a salt of an inorganic or organic acid of a compound of formula

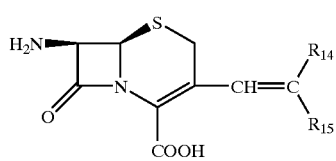
V wherein
$R_{14}$ and $R_{15}$ are the same or different and each denote hydrogen or an organic residue in an organic solvent optionally in the presence of water with ozone b) for the production of a compound of formula

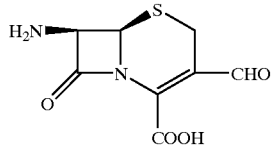
IIIg treating a compound of formula IIIe wherein $R'''_b$, $R'''_c$ and $R'''_d$ ar as defined above, with a base.

Compounds of formulae IV are partially new and may be obtained analogously to conventional methods, or, as described in the examples.

In another aspect the present invention provides a compound of formula $$H_2N—R_{2i} \quad\quad IVi$$

wherein $R_{2i}$ denotes a group of formula $$—N(R_{4i}R_{5i}) \quad\quad IIbi$$

wherein $R_{4i}$ is the same as $R_4$ in formula I and denotes preferably hydrogen or alkyl and $R_{5i}$ denotes a group of formula

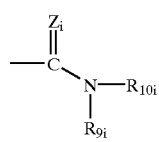
IIei wherein $Z_i$ denotes N—$R_{13i}$, wherein
$R_{13i}$ is the same as $R_{13}$ in formula I and denotes preferably hydrogen or alkyl, and
$R_{9i}$ and $R_{10i}$ together with the nitrogen atom denote heterocyclyl which is a piperazinyl; or $R_{4i}$ is the same as $R_4$ in formula I and denotes preferably hydrogen, and $R_{5i}$ denotes a group of formula

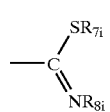
IIdi wherein $R_{8i}$ denotes alkyl, preferably at least $C_2$ alkyl; or cycloalkyl, preferably cyclopropyl, and $R_{7i}$ denotes alkyl, preferably methyl; or $R_{4i}$ is the same as $R_4$ in formula I and denotes preferably hydrogen or alkyl and $R_{5i}$ denotes a group of formula

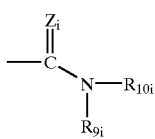
IIei wherein
$Z_i$ denotes N—$R_{13i}$, wherein
$R_{13i}$ denotes hydrogen, alkyl or cycloalkyl, preferably hydrogen or alkyl
$R_{9i}$ denotes hydrogen and
$R_{10i}$ denotes $CH_2CF_3$, $C(CH_3)_3$, OH or an alkyl group having at least 2 carbon atoms which is substituted by dialkyl amine or trialkyl ammonium, hydroxy; or
$R_{4i}$ is the same as $R_4$ in formula I and denotes preferably hydrogen
$R_{5i}$ denotes a group of formula

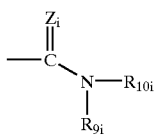
IIei wherein
$Z_i$ denotes N—$R_{13i}$, wherein
$R_{13i}$ denotes alkyl or cycloalkyl, preferably alkyl, and
$R_{9i}$ and $R_{10i}$ together with the nitrogen atom denote heterocyclyl which is morpholyl or pyrrolidinyl; or
$R_{4i}$ is the same as $R_4$ in formula I and denotes preferably hydrogen
$R_{5i}$ denotes a group of formula

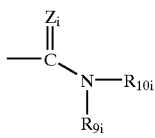
IIei wherein
$Z_i$ denotes N—$R_{13i}$, wherein
$R_{13i}$ denotes hydrogen, alkyl or cycloalkyl, preferably hydrogen, and
$R_{9i}$ denotes hydrogen, and
$R_{10i}$ denotes cycloalkyl, preferably cyclopropyl; or
$R_{4i}$ is the same as $R_4$ in formula I and denotes preferably hydrogen
$R_{5i}$ denotes a group of formula

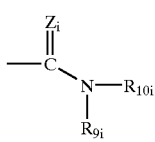
IIei wherein
$Z_i$ denotes N—$R_{13i}$, wherein
$R_{13i}$ is the same as $R_{13}$ in formula I and denotes preferably hydrogen, $R_{9i}$ denotes hydrogen or alkyl, preferably hydrogen, and
$R_{10i}$ denotes a group

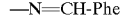
—N=CH-Phe wherein Phe denotes phenyl, preferably a dihydroxy phenyl, or
$R_{4i}$ is the same as $R_4$ in formula I and denotes preferably hydrogen
$R_{5i}$ denotes a group of formula

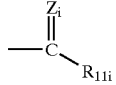
IIfi wherein
$Z_i$ denotes N—$R_{13i}$, wherein
$R_{13i}$ denotes hydrogen, alkyl or cycloalkyl, preferably hydrogen,
$R_{11i}$ denotes a dihydroxyphenyl or substituted pyrrolidyl by alkyl; or
$Z_i$ denotes oxygen and
$R_{11i}$ denotes the group of formula

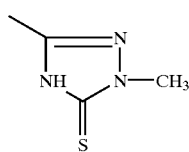

In another aspect the present invention provides a compound of formula

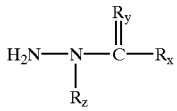
IVa wherein
$R_x$ is a group of formula

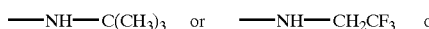
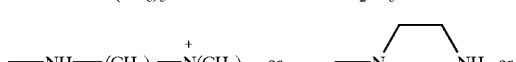
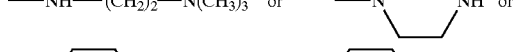
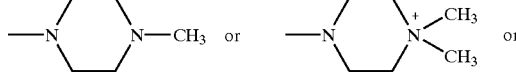
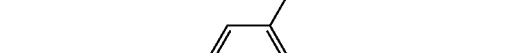
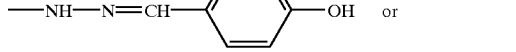

-continued

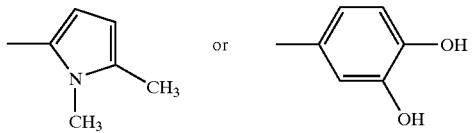

$R_y$ is NH and
$R_z$ is hydrogen; or
$R_x$ is a group of formula

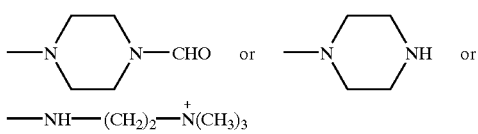

$R_y$ is NH and
$R_z$ is $CH_3$; or
$R_x$ is —$SCH_3$
$R_y$ is a group of formula

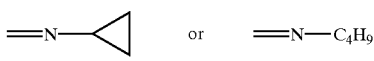

and
$R_z$ is hydrogen, or
$R_x$ is a group of formula

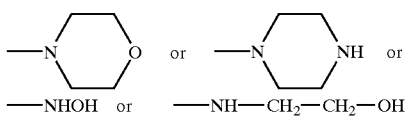

$R_y$ is N—$CH_3$ and
$R_z$ is hydrogen; or
$R_x$ is the group

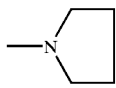

$R_y$ is N—$C_2H_5$ and
$R_z$ is hydrogen; or
$R_x$ is the group

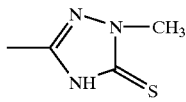

$R_y$ is oxygen and
$R_z$ is hydrogen.

Compounds of formulae VI are partially new and may be obtained analogously to conventional methods, or, as described in the examples.

In another aspect the present invention provides a compound of formula

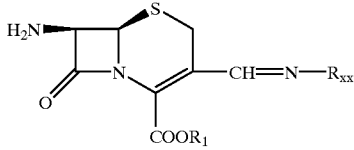

VIa wherein
$R_1$ is as defined in formula I and
$R_{xx}$ denotes the group

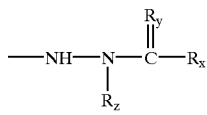

wherein
$R_x$, $R_y$ and $R_z$ as defined above.

In this specification unless otherwise indicated terms such as "compound of formula I, IA, $I_s$, $I_p$, $I_q$, IVi, IVa and VIa" embrace the compound in any form, for example in salt form and free base form. The present invention thus includes a compound in free or base form or, where such forms exist, in salt form, for example in form of an acid addition salt, inner salt, quaternary salt and/or in solvate, for example hydrate form thereof. A salt may be a pharmaceutically acceptable salt of a compound of formulae I, IA, $I_s$, $I_p$, $I_q$ such as a metal salt or an amine salt. Metal salts include for example sodium, potassium, calcium, barium, zinc, aluminum salts, preferably sodium or potassium salts. Amine salts include for example trialkylamine, procaine, dibenzylamine and benzylamine salts. A free form of a compound of formulae I, IA, $I_s$, $I_p$, $I_q$, IVi, IVa and VIa may be converted into a salt form and vice versa.

In a further aspect the present invention provides a compound of formulae I, IA, $I_s$, $I_p$, $I_q$, IVi, IVa and VIa in free form; or in salt form, for example in acid addition salt form or in metal salt form; and a compound of formulae I, IA, $I_s$, $I_p$, $I_q$, IVi and VIa and VIa in solvate form.

A compound of formula I may also be obtained analogously to other processes conventional in the β-lactam chemistry.

The compounds of formula I, hereinafter designated as "active compound(s) of the invention" exhibits pharmacological activity and are therefore useful as pharmaceuticals. In particular, the active compounds of the invention show antimicrobial, e.g. antibacterial, activity against gram negative and gram positive bacteria such as Pseudomonas, e.g. *Pseudomonas aeruginosa, Pseudomonas fluorescens*; Enterobacter, e.g. *Enterobacter cloacae*; Enterococcus, e.g. *Enterococcus faecalis*; Moraxella, e.g. *Moraxella catarrhalis*; Haemophilus, e.g. *Haemophilus influenza*; Klebsiella, e.g. *Klebsiella edwardsii, Klebsiella pneumoniae*; Streptococcus, e.g. *Streptococcus pneumoniae, Streptococcus durans, Streptococcus faecium, Streptococcus pyogenes*; Staphylococcus, e.g. *Staphylococcus aureus, Staphylococcus pyogenes*; Escherichia, e.g. *Escherichia coli*; and Proteus, e.g. *Proteus mirabilis* in vitro in the Agar Dilution Test according to National Commitee for Clinical Laboratory Standards (NCCLS) 1993, Document M7-A3Vol.13, No. 25: "Methods for dilution Antimicrobial Susceptibility Tests for Bacteria that Grow Aerobically—Third Edition, Approved Standard" and in vivo in the septikaemic mouse model. The active compounds of the invention show activity in the mouse when administerd at dosages from about 0.05 to 50 mg/kg body weight ($ED_{50}$ values).The active compounds show an MHK($\mu$g/ml) in the Agar Dilution Test from about 0.005 to ca. 50. The active compounds of the invention show an surprising overall activity spectrum.

It has, for example, been determined that the MHK ($\mu$g/ml) of the compound of Example 139 against, for example *Enterococcus faecalis* strains ATTC 29212 or ATCC 51299, is of ca. 0.08 to 0.25; ainst *Staphylococcus aureus* strains ATCC 29213 or ATCC 9144 is of ca. 0.2 to 0.4 and against *Pseudomonas aeruginosa* strain 27853 is ca. 0.8.

The active compounds of the invention are, therefore, useful for the treatment of microbial, e.g. bacterial diseases.

In another aspect the present invention provides a compound of claim 1 for use as a pharmaceutical, preferably as an antimicrobial agent, such as an antibiotic.

In a further aspect the present invention provides a compound of claim 1 for use in the preparation of a medicament for the treatment of microbial diseases, for example of diseases caused by bacterias selected from Pseudomonas, Enterobacter, Enterococcus, Moraxelia, Haemophilus, Klebsiella, Streptococcus, Staphylococcus, Escherichia, and Proteus.

In a further aspect the present invention provides a method of treatment of microbial diseases which comprises administering to a subject in need of such treatment an effective amount of a compound of formula I.

For this indication, the appropriate dosage will, of course, vary depending upon, for example, the compound of formula I employed, the host, the mode of administration and the nature and severity of the conditions being treated. However, in general, for satisfactory results in larger mammals, for example humans, an indicated daily dosage is in the range from about 0.05 to 5 g, for example 0.1 to about 2.5 g, of an active compound of the invention conveniently administered, for example, in divided doses up to four times a day.

An active compound of the invention may be administered by any conventional route, for example orally, e.g. in form of tablets or capsules, or parenterally in the form of injectable solutions or suspensions, e.g. in analogous manner to cefotaxime.

The compound 7-[[(5-Amino-1,2,4-thiadiazol-3-yl)-(Z)-(fluormethoxyimino)acetyl]amino]-3-[[(piperazinoiminomethyl)hydrazono]methyl]-3-cephem-4-carboxylic acid (compound of Example 139) is the preferred compound of the invention for use as an antimicrobial agent.

It has, for example been determined that the MHK ($\mu$g/ml) of the compound of Example 139 (tested in form of the trihydrochloride) against, for example *Streptococcus pneumoniae*, strain ATCC 49619 is ca. 0.01 whereas, for example ceftriaxone shows an MHK ($\mu$g/ml) of ca. 0.02. It is therefore, indicated that for the treatment of microbial diseases, e.g. bacterial diseases the preferred compounds of the invention may be administered to larger mammals, for example humans, by similar modes of administration at similar dosages than conventionally employed with ceftriaxone.

The compounds of formula I may be administered in pharmaceutically acceptable salt form, e.g. acid addition salt form or base addition salt form or in the corresponding free forms, optionally in solvate form. Such salts exhibit the same order of activity as the free forms.

The present invention also provides pharmaceutical compositions comprising a compound of formula I in pharmaceutically acceptable salt form or free form in association with at least one pharmaceutical carrier or diluent.

Such compositions may be manufactured in conventional manner.

Unit dosage form may contain, for example 10 mg to about 1 g, for example 10 mg to about 700 mg.

In the following Examples the temperatures indicated are in degree Celsius.

EXAMPLE 1

Dibydrochloride of 7-[(2-Amino-4-thiazolyl)-(Z)-(methoxyimino)acetyl]amino-3-[[(aminoiminomethyl)hydrazono]methyl]-3-cephem-4-carboxylic acid (Process a)

1.24 g of the hydrogen carbonate of aminoguanidine are dissolved in 9.15 ml of 2 N HCl and added under stirring to a solution of 3.2 g of the trifluoroacetate of N-(1,4,5a,6-tetrahydro-3-hydroxy-1,7-dioxo-3H,7H-azeto[2,1-b]furo[3,4-d][1,3]-thiazin-6-yl)-2-(2-aminothiazol-4yl)-(Z)-2-methoxyimino acetic acid amide in 125 ml of 4% aqueous acetonitrile. After ca. 90 minutes the precipitated dihydrochloride of 7-[(2-Amino-4-thiazolyl)(methoxyimino)acetyl]amino-3-[[(aminoimino-methyl)-hydrazono]methyl]-3-cephem-4-carboxylic acid is filtered off, washed with acetonitrile and dried.

EXAMPLE 2

Dihydrochloride of 7-[[(2-Amino-4-thiazolyl)-(Z)-(hydroxyimino)acetyl]amino]-3-[[(amino-iminomethyl)hydrazono]methyl]-3-cephem-4-carboxylic acid (Process a)

a) 10 g of the hydrochloride of N-(1,4,5a,6-tetrahydro-3-hydroxy-1,7-dioxo-3H,7H-azeto[2,1-b]furo[3,4-d][1,3]-thiazin-6-yl)-2-(2-aminothiazol4-yl)-(Z)-2-(acetoxyimino)-acetic acid amide are suspended in 160 ml of acetonitrile and treated with 53 ml of water and 11 ml of 8 N HCl. The reaction mixture is stirred for ca. 14 hours at room temperature. A clear solution is obtained in which the acetoxyimino group being hydrolyzed to give the hydroxyimino group.

b) 3 g of the hydrogen carbonate of aminoguanidine are dissolved in 11 ml of 1 N HCl and added dropwise to the solution obtained in step a) which is cooled to 0°. After ca. 30 minutes the reaction mixture is warmed to room temperature and stirred for ca. another 2.5 hours. The dihydrochloride of 7-[[(2-Amino4-thiazolyl)-(Z)-(hydroxyimino) acetyl]amino]-3-[[(amino-iminomethyl)hydrazono]methyl]-3-cephem-4-carboxylic acid precipitate, is filtered off, washed with a mixture of acetonitrile and water, acetonitrile and with ether and dried.

EXAMPLE 3

Sodium salt of 7-[(2-Amino-4-thiazolyl)(methoxyimino)acetyl]amino-3-[(methoxyimino)methyl]-3-cephem-4-carboxylic acid (Process b)

0.5 g of 7-amino-3-[(methoxyimino)methyl]-3-cephem-4-carboxylic acid and 0.75 g of (2-amino-4-thiazolyl)(methoxyimino)acetic acid mercaptobenzthiazolyl ester are suspended in a mixture of 2.4 ml of water and 4.8 ml of acetone. Ca. 1.8 ml of 2N sodium hydroxide solution are added dropwise in such a way that a pH of 8.0 is kept. The reaction mixture is stirred at 20° for ca. 1 hour. 2.4 ml of acetone are added dropwise. A clear solution is obtained within 3 hours. 120 ml of acetone are slowly added. A suspension is obtained which is cooled to 0°. After ca. 5 hours the precipitate formed is filtered off and redissolved in 4 ml of water. The clear solution is treated with 0.2 g of active charcoal and stirred for ca. 15 minutes. Active charcoal is filtered off and 100 ml of acetone are added within ca. 1 hour at 0°. The sodium salt of 7-[(2-amino-4-thiazolyl)(methoxyimino)acetyl]amino-3-[(methoxy-imino)methyl]-3-cephem-4-carboxylic acid is obtained in form of colourless crystals, which are filtered off, washed with ca. 5 ml of acetone and dried.

The compounds of the following TABLE 1 of formula IA (V is =N—O— in all of the Examples; and W is CH in Examples 4 to 68 and 70 to 138; and W is N in Examples 69 and 139 of TABLE 1) may be obtained in analogous manner to that described in Examples 1 to 3. Salt forms are exemplified. The configuration of $R_3$ in group —C=N—$R_3$ is syn [(Z)].

TABLE 1

| Example | $R_3$ | $R_2$ | $R_1$ | Salt |
|---|---|---|---|---|
| 4 | $CH_3$ | OH | H | — |
| 5 | —$CH_2COOH$ | —NH—C(=NH)—$NH_2$ | H | 2HCl |
| 6 | $CH_3$ | —$OCH_2COONa$ | Na | — |
| 7 | $CH_3$ | —NH—CO—$NH_2$ | H | — |
| 8 | $CH_3$ | —NH—C(=NH)—NH—$CH_3$ | H | 2HCl |
| 9 | $CH_3$ | —NH—$C_6H_5$ | H | — |
| 10 | $COCH_3$ | —NH—C(=NH)—$NH_2$ | H | 2HCl |
| 11 | $CH_3$ | —NH—C(=NH)—NH—$C_2H_5$ | H | 2HCl |
| 12 | $CH_3$ | —NH—C(=NH)—N(pyrrolidinyl) | H | 2HCl |
| 13 | $CH_3$ | —NH—C(=N—$CH_3$)—NH—$CH_3$ | H | 2HCl |
| 14 | $CH_3$ | —NH—(4,5-dihydroimidazol-2-yl)—NH | H | 2HCl |
| 15 | $CH_3$ | —NH—C(=O)—NH—$C_6H_5$ | H | 2HCl |
| 16 | H | —NH—C(=NH)—NH—$CH_3$ | H | 2HCl |
| 17 | H | —NH—C(=NH)—N(pyrrolidinyl) | H | 2HCl |

TABLE 1-continued

| Example | R₃ | R₂ | R₁ | Salt |
|---|---|---|---|---|
| 18 | H | 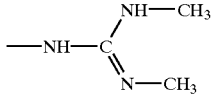 —NH—C(=N—CH₃)(NH—CH₃) | H | 2HCl |
| 19 | H | 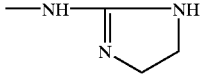 —NH-(2-imidazolin-2-yl) | H | 2HCl |
| 20 | CH₃ | —NH—CS—NH₂ | H | 2HCl |
| 21 | CH₃ | 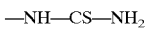 —NH—C(=S)—NH—C₆H₅ | H | HCl |
| 22 | CH₃ | 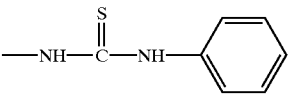 —NH—C(=O)—NH—C₆H₅ | H | HCl |
| 23 | CH₃ | 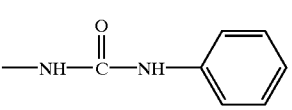 —NH—C(=S)—NH—CH₃ | H | HCl |
| 24 | CH₃ | 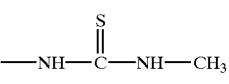 4-methylpiperazin-1-yl | H | 2HCl |
| 25 | CH₃ | 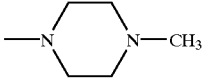 —NH—C(=NH)—NH—CH₂CH=CH₂ | H | 2HCl |
| 26 | CH₃ | 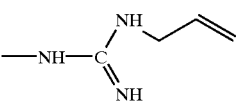 —NH-(1,4,5,6-tetrahydropyrimidin-2-yl) | H | 2HCl |
| 27 | CH₃ | 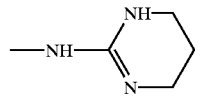 —NH—C(=NH)—NH—C₄H₉ | H | 2HCl |
| 28 | CH₃ | 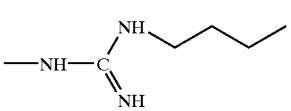 —N(CH₃)—C(=S)—NH—CH₃ | H | HCl |
| 29 | CH₃ | 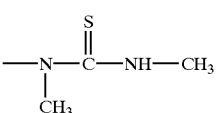 —NH—C(=N—CH₃)-morpholino | H | 2HCl |
| 30 | CH₃ | 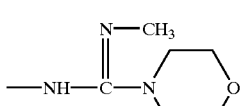 —NH—C(=NH)—NH—C(CH₃)₃ | H | 2HCl |
| 31 | CH₃ | 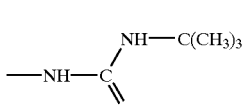 —NH—C(=N—CH₃)—N(CH₃)₂ 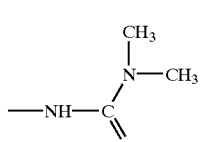 | H | 2HCl |

TABLE 1-continued

| Example | $R_3$ | $R_2$ | $R_1$ | Salt |
|---|---|---|---|---|
| 32 | $CH_3$ | —HN—C(=NH)—NH—CH$_2$—CF$_3$ | H | 2HCl |
| 33 | $CH_3$ | —NH—C(=NH)—N(morpholine) | H | 2HCl |
| 34 | $CH_3$ | —NH—C(=O)—CH$_2$—N$^+$(CH$_3$)$_3$ | H | Cl— |
| 35 | $CH_3$ | —NH—C(=NH)—NH—cyclopropyl | H | 2HCl |
| 36 | $CH_3$ | —NH—C(=NH)—NH—OH | H | 2HCl |
| 37 | $CH_3$ | —NH—C(=NH)—N(CH$_3$)$_2$ | H | 2HCl |
| 38 | $CH_3$ | —NH—C(=NH)—NH—CH$_2$-(2-pyridyl) | H | 2HCl |
| 39 | $CH_3$ | —NH—C(=NH)—NH—CH$_2$-(3-pyridyl) | H | 2HCl |
| 40 | $CH_3$ | —NH—C(=NH)—NH—CH$_2$-(4-pyridyl) | H | 2HCl |
| 41 | $CH_3$ | (1-methyl-hydantoin-3-yl) | H | HCl |
| 42 | $CH_3$ | —NH—C(=N—CH$_3$)—N(piperazine) | H | 3HCl |
| 43 | $CH_3$ | —NH-(2-pyridyl) | H | 2HCl |

TABLE 1-continued

| Example | R₃ | R₂ | R₁ | Salt |
|---|---|---|---|---|
| 44 | CH₃ | (5-amino-3-thioxo-1,2,4-triazolidin-3-yl)amino group with NH₂, S, NH—NH | H | HCl |
| 45 | CH₃ | —NH—C(=NH)—N(piperidinyl) | H | 2HCl |
| 46 | CH₃ | —NH—C(=NH)—N(piperazinyl)NH | H | 3HCl |
| 47 | CH₃ | —NH—C(=N—CH₃)—NH—OH | H | 2HCl |
| 48 | CH₃ | =N—C(N(CH₃)CH₂CH₂N(CH₃)) (1,3-dimethylimidazolidin-2-ylidene) | H | 2HCl |
| 49 | CH₃ | —NH—C(=O)—(4-pyridyl) | H | HCl |
| 50 | CH₃ | —NH—C(=N—CH₃)—N(piperazinyl-N'-CHO) | H | 2HCl |
| 51 | CH₃ | —NH—C(=O)—CH₂—⁺N(pyridinium) | H | Cl— |
| 52 | CH₃ | —NH—C(=O)—(3-methyl-5-thioxo-1,2,4-triazol-1-yl) with HN, N—CH₃, S | H | HCl |
| 53 | CH₃ | —NH—(6-methyl-4-amino-5-oxo-1,2,4-triazin-3-yl) with N=N, CH₃, NH₂, O | H | 2HCl |
| 54 | CH₃ | —NH—C(CH₃)=NH | H | 2HCl |

TABLE 1-continued
| Example | R₃ | R₂ | R₁ | Salt |
|---|---|---|---|---|
| 55 | CH₃ | 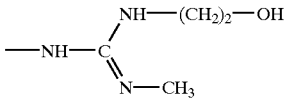 | H | 2HCl |
| 56 | CH₃ | 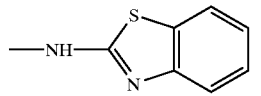 | H | HCl |
| 57 | CH₃ | 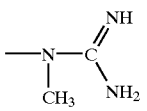 | H | 2HCl |
| 58 | CH₃ | 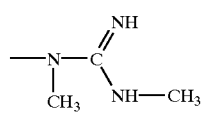 | H | 2HCl |
| 59 | CH₃ | 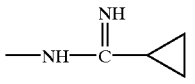 | H | 2HCl |
| 60 | CH₃ | 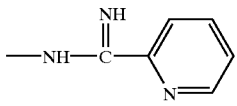 | H | 2HCl |
| 61 | CH₃ | 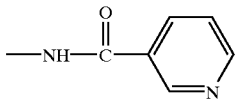 | H | HCl |
| 62 | CH₃ | 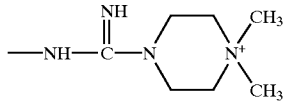 | H | Cl⁻ 2HCl |
| 63 | CH₃ | 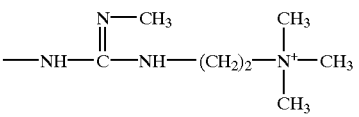 | H | Cl⁻ 2HCl |
| 64 | CH₃ | 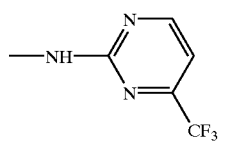 | H | HCl |
| 65 | CH₃ | 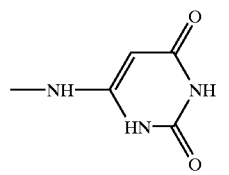 | H | HCl |
| 66 | CH₃ | 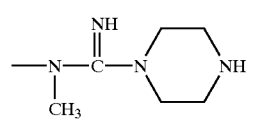 | H | 3HCl |

TABLE 1-continued
| Example | R₃ | R₂ | R₁ | Salt |
|---|---|---|---|---|
| 67 | CH₃ | 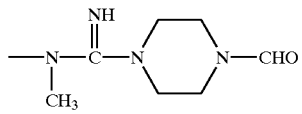 | H | 2HCl |
| 68 | CH₃ | 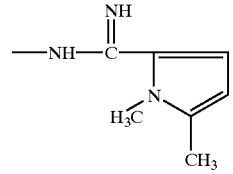 | H | 2HCl |
| 69 | CH₂F | 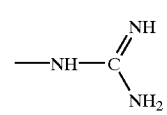 | H | 2HCl |
| 70 | H | 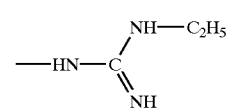 | H | 2HCl |
| 71 | H | 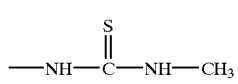 | H | HCl |
| 72 | H | 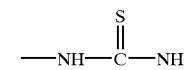 | H | HCl |
| 73 | H | 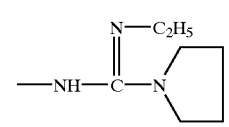 | H | 2HCl |
| 74 | H | 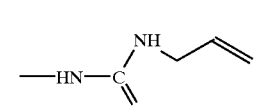 | H | 2HCl |
| 75 | H | 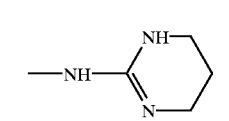 | H | 2HCl |
| 76 | H | 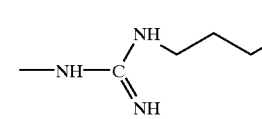 | H | 2HCl |
| 77 | H | OCH₃ | H | HCl |
| 78 | H | 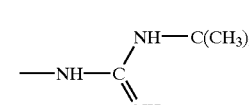 | H | 2HCl |
| 79 | H | 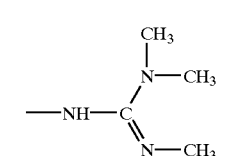 | H | 2HCl |

TABLE 1-continued

| Example | R$_3$ | R$_2$ | R$_1$ | Salt |
|---------|-------|-------|-------|------|
| 80 | H | —HN—C(=NH)—NH—CH$_2$—CF$_3$ | H | 2HCl |
| 81 | H | —NH—C(=NH)—N(morpholino) | H | 2HCl |
| 82 | H | —NH—C(=NH)—NH—cyclopropyl | H | 2HCl |
| 83 | H | —NH—C(=NH)—NH—OH | H | 2HCl |
| 84 | H | —NH—C(=NH)—N(CH$_3$)$_2$ | H | 2HCl |
| 85 | H | —NH—C(=NH)—NH—CH$_2$-(2-pyridyl) | H | 2HCl |
| 86 | H | —NH—C(=NH)—NH—CH$_2$-(3-pyridyl) | H | 2HCl |
| 87 | H | —NH—C(=NH)—NH—CH$_2$-(4-pyridyl) | H | 2HCl |
| 88 | H | 1-methylhydantoin-3-yl | H | HCl |
| 89 | H | —NH—C(=S)—NH—phenyl | H | HCl |
| 90 | R | —NH-(2-pyridyl) | H | 2HCl |
| 91 | H | 4-amino-5-thioxo-1,2,4-triazol-3-yl | H | HCl |

TABLE 1-continued

| Example | R₃ | R₂ | R₁ | Salt |
|---|---|---|---|---|
| 92 | —C(CH₃)₂—COOH | —NH—C(=NH)—NH—CH₃ | H | 2HCl |
| 93 | H | —NH—C(=N—CH₃)—NH—OH | H | 2HCl |
| 94 | H | —NH—C(=N—CH₃)—NH—(CH₂)₂—OH | H | 2HCl |
| 95 | H | —NH-(3-yl of 6-methyl-5-oxo-4-amino-4,5-dihydro-1,2,4-triazine) | H | 2HCl |
| 96 | H | —NH—C(=NH)—N(piperazin-1-yl) | H | 3HCl |
| 97 | H | —N=C(1,3-dimethylimidazolidin-2-ylidene) | H | 2HCl |
| 98 | H | —N(CH₃)—C(=NH)—NH₂ | H | 2HCl |
| 99 | H | —NH—C(CH₃)=NH | H | 2HCl |
| 100 | H | —NH—CH=NH | H | 2HCl |
| 101 | CH₃ | —NH—CH=NH | H | 2HCl |
| 102 | —C(CH₃)₂—COOH | —NH—C(=NH)—NH₂ | H | 2HCl |
| 103 | —C(CH₃)₂—COOH | —NH—C(=NH)—NH—OH | H | 2HCl |
| 104 | —C(CH₃)₂—COOH | —NH—C(=NH)—NH—CH₂—(pyridin-2-yl) | H | 2HCl |

TABLE 1-continued

| Example | R₃ | R₂ | R₁ | Salt |
|---|---|---|---|---|
| 105 | —C(CH₃)₂—COOH | —NH—C(=NH)—NH-cyclopropyl | H | 2HCl |
| 106 | —C(CH₃)₂—COOH | —NH—C(=N—CH₃)—NH—CH₃ | H | 2HCl |
| 107 | —C(CH₃)₂—COOH | —NH—C(=NH)—N(pyrrolidinyl) | H | 2HCl |
| 108 | CH₃ | —NH—C(=NH)—S—CH₃ | H | 2HCl |
| 109 | CH₂COOH | —NH—C(=NH)—NH-cyclopropyl | H | 2HCl |
| 110 | CH₂COOH | —NH—C(=N—CH₃)—NH—CH₃ | H | 2HCl |
| 111 | CH₂COOH | —NH—C(=NH)—N(pyrrolidinyl) | H | 2HCl |
| 112 | H | —NH—C(=NH)—(2-pyridyl) | H | 2HCl |
| 113 | H | —NH—C(=NH)-cyclopropyl | H | 2HCl |
| 114 | H | —NH—C(=NH)—N(piperidinyl) | H | 2HCl |
| 115 | H | —NH—C(=NH)—N(piperazinyl-N'-CHO) | H | 2HCl |
| 116 | H | —NH—C(=N—CH₃)—NH—(CH₂)₂—N(CH₃)₂ | H | 2HCl |
| 117 | H | —NH—C(=N—CH₃)—NH—(CH₂)₂—N⁺(CH₃)₃ | H | Cl—2HCl |

TABLE 1-continued

| Example | R₃ | R₂ | R₁ | Salt |
|---|---|---|---|---|
| 118 | H | —NH—C(=NH)—(3,4-dihydroxyphenyl) | H | 2HCl |
| 119 | H | —NH—C(=NH)—(1-methyl-5-methyl-pyrrol-2-yl) | H | 2HCl |
| 120 | H | —NH—C(=O)—(pyridin-4-yl) | H | 2HCl |
| 121 | H | —NH—C(=NH)—N(piperazine-4,4-dimethyl N⁺) | H | Cl—2HCl |
| 122 | H | —NH—C(=NH)—N(4-methylpiperazin-1-yl) | H | 3HCl |
| 123 | H | —N(CH₃)—C(=NH)—NH—CH₃ | H | 2HCl |
| 124 | H | —NH—C(=NH)—NH—(CH₂)₂—N(CH₃)₂ | H | 2HCl |
| 125 | H | —N(CH₃)—C(=NH)—NH—(CH₂)₂—N(CH₃)₂ | H | 3HCl |
| 126 | H | —NH—C(=NH)—NH—N=CH—(3,4-dihydroxyphenyl) | H | 3HCl |
| 127 | H | —NH—C(=NH)—NH—NH₂ | H | 3HCl |
| 128 | H | —N(CH₃)—C(=NH)—N(piperazin-1-yl) | H | 3HCl |
| 129 | CH₃ | —NH—C(=S)—NH—cyclopropyl | H | HCl |

TABLE 1-continued

| Example | R₃ | R₂ | R₁ | Salt |
|---|---|---|---|---|
| 130 | CH₃ | —NH—C(=S)—NH—(CH₂)₃—CH₃ | H | HCl |
| 131 | CH₃ | —NH—C(S—CH₃)=N—<cyclopropyl> | H | 2HCl |
| 132 | CH₃ | —NH—C(S—CH₃)=N—(CH₂)₃—CH₃ | H | 2HCl |
| 133 | CH₃ | —NH—C(=S)—NH—(CH₂)₂—SO₃H | H | — |
| 134 | H | —NH—C(=S)—NH—<cyclopropyl> | H | HCl |
| 135 | H | —NH—C(=S)—NH—(CH₂)₃—CH₃ | H | HCl |
| 136 | CH₃ | —NH—C(=S)—N(piperazinyl)—CH₃ | H | 2HCl |
| 137 | CH₃ | —N(CH₃)—C(=S)—NH₂ | H | HCl |
| 138 | CH₃ | —NH—COC(CH₃)₃ | H | HCl |
| 139 | CH₂F | —NH—C(=NH)—N(piperazinyl)NH | H | 3HCl |

EXAMPLE 140

Dihydrochloride of 7-[2-(2-aminothiazol-4-yl)-(Z)-2-pentenoylamino]-3-[[(aminoimino-methyl)hydrazono]methyl]-3-cephem-4-carboxylic acid 1 g of N-(1,4,5a,6-tetrahydro-3-hydroxy-1,7-dioxo-3H,7H-azeto[2,1-b]furo[3,4-d][1,3]-thiazin-6-yl)-2-[2-(tert.-butoxycarbonylamino)thiazol4-yl]-(Z)-2-pentenoic acid amide is dissolved in a mixture of 30 ml of methanol and 30 ml of acetonitrile and 0.3 g of the hydrogencarbonate of aminoguanidine are added. A pH of 2.0 is adjusted by addition of methanolic HCl. Stirring is continued at room temperature. Within ca. 30 minutes a light coloured precipitate forms, which is filtered off after ca. 3 hours, washed with acetonitrile and ether and dried. The dihydrochloride of 7-[2-(2-aminothiazol-4-yl)-(Z)-2-pentenoylamino]-3-{[(aminoimino-methyl)hydrazono]-methyl}-3-cephem-4-carboxylic acid is obtained in the form of a light yellow powder.

EXAMPLE 141

Trifluoroacetate of 7-[(2-Amino-4-thiazolyl)-(Z)-(methoxyimino)acetyl]amino-3-(hydrazonomethyl)-3-cephem-4-carboxylic acid A suspension of 3 g of 7-[(2-amino-4-thiazolyl)-(Z)-(methoxyimino)acetyl]amino-3-[[2-(1,1-dimethylethoxy)-2-oxoethoxy]hydrazonomethyl]-3-cephem-4-carboxylic acid in 75 ml of methylenchloride is treated at ca. 0° with 0.6 ml of anisol. 10 ml of trifluoro acetic acid are added dropwise under stirring. The solution obtained is stirred for ca. further 3 hours at 0°. The reaction mixture is poured into 600 ml of ether. The trifluoroacetate of 7-[(2-Amino-4-thiazolyl)-(Z)-(methoxyimino)acetyl]amino-3-(hydrazono)-3-cephem-4-carboxylic acid precipitates, is filtered off and dried.

EXAMPLE 142

Hydrobromide of 7-[(2-amino-4-thiazolyl)-(Z)-(methoxyimino)acetyl]amino-3-[(4-methylthiazol-2-yl)hydrazonomethyl]-3-cephem-4-carboxylic acid 1 g of 7-[(2-amino-4-thiazolyl)-(Z)-(methoxyimino)acetyl]amino-3-[(aminothioxomethyl)-hydrazonomethyl]-3-cephem-4-carboxylic acid is suspended in 30 ml of acetonitrile and stirred after addition of 2.5 ml of N,O-bistrimethylsilylacetamide for ca. 20 minutes. The clear solution obtained is treated with 0.6 g of bromoacetone and stirred overnight. 1 ml of water are added. The precipitate is filtered off and dried. The hydrobromide of 7-[(2-amino-4-thiazolyl)-(Z)-(methoxyimino)acetyl]amino-3-[(4- methylthiazol-2-yl)hydrazonomethyl]-3-cephem-4-carboxylic acid is obtained as a yellow solid.

EXAMPLE 143

Hydrobromide of 7-[(2-amino-4-thiazolyl)-(Z)-(methoxyimino)acetyl]amino-3-[(4-methylthiazol-2-yl)methylhydrazonomethyl]-3-cephem-4-carboxylic acid 1 g of 7-[(2-amino-4-thiazolyl)-(Z)-(methoxyimino) acetyl]amino-3-[(aminothioxomethyl)-methylhydrazonomethyl]-3-cephem-4-carboxylic acid is reacted in analogous manner as described in Example 142 with N,O-bistrimethylsilylacetamide and with bromoacetone. The hydrobromide of 7-[(2-amino-4-thiazolyl)-(Z)-(methoxyimino)acetyl]amino-3-[(4-methylthiazol-2-yl) methylhydrazonomethyl]-3-cephem-4-carboxylic acid is obtained as a yellow solid.

EXAMPLE 144

Dihydrate of 6R-trans(Z)-7-[(2-Amino-4-thiazolyl) (methoxyimino)-acetyl]amino-3[[(imino (methylamino)methyl)hydrazono]methyl]-3-cephem-4-carboxylic acid 1.1 g of the dihydrochloride obtained according to Example 8 are dissolved in 25 ml of water, treated with 0.5 g of active charcoal and stirred for ca. 5 minutes. The almost colourless filtrate is poured into 5 ml of water under stirring. A pH of about 7 is kept by addition of 2.5% aqueous ammonia. The precipitate obtained is filtered off and dried. The dihydrate of 6R-trans(Z)-7-[(2-Amino-4-thiazolyl) (methoxyimino)-acetyl]amino-3[[(imino(methylamino) methyl)hydrazono]-methyl]-3-cephem-4-carboxylic acid is obtained as a yellowish powder.

EXAMPLE 145

6R-trans(Z)-7-[(2-amino-4-thiazolyl) (methoxyimino)acetyl]amino-3-[[(imino (methylamino)methyl)hydrazono]methyl]-3-cephem-4-carboxylic acid 1-(isopropoxycarbonyloxy)ethyl ester 5.5 g of the dihydrate obtained according to Example 144 are dissolved in 55 ml of dimethylacetamide under addition of 1.43 ml tetramethylguanidine. This solution is cooled to 0°, treated with a solution of 4.4 g of 1-iodoethyl-isopropylcarbonate in 30 ml of toluene and stirred for ca. 90 minutes at 0°. The reaction mixture is poured into 1 liter of diethylether. The precipitate obtained is filtered off and stirred twice each with 500 ml of acetonitrile. The acetonitrile phases are combined, filtered and evaporated to a volume of ca. 10 ml. The oily residue is treated with 400 ml of water. A precipitate forms which is filtered off and dried. The precipitate is stirred with 700 ml of ethyl acetate. After evaporation of the ethyl acetate yellow coloured 6R-trans (Z)-7-[(2-amino-4-thiazolyl)-(methoxyimino)acetyl]amino-3-[[(imino(methylamino)methyl)hydrazono]methyl]-3-cephem-4-carboxylic acid 1-(isopropoxycarbonyloxy)ethyl ester is obtained in the form of a diastereomeric mixture in the ratio of ca. 1:1.

EXAMPLE 146

6R-trans(Z)-7-[((Acetoxyimino)-2-amino-4-thiazolyl)acetyl]amino-3-[[(aminoiminomethyl) hydrazono]methyl]-3-cephem-4-carboxylic acid 1-(isopropoxycarbonyloxy)ethyl ester 0.72 g of the hydrogen carbonate of aminoguanidine are dissolved in 5.2 ml of 2 N HCl. This solution is added to a solution of 2 g of 6R-trans(Z)-7-[((acetoxyimino)-2-amino-4-thiazolyl)acetyl]amino-3-formyl-3-cephem-4-carboxylic acid 1-(isopropoxycarbonyloxy)ethyl ester in 14 ml of acetonitrile containing 1.3 ml of water. The reaction mixture is stirred for ca. 45 minutes at room temperature and poured into 100 ml of acetonitrile. The precipitate formed is filtered off and dissolved in 100 ml of water. The pH of the solution obtained is adjusted to 7 by addition of 0.5 N aqueous sodium hydrogen carbonate. A yellow suspension is obtained which is extracted twice with a mixture of 200 ml of ethyl acetate and 40 ml of acetonitrile. The organic phases are combined, dried over NaSO$_4$ and evaporated. 6R-trans (Z)-7-[((acet-oxyimino)-2-amino-4-thiazolyl)acetyl]amino-3-[[(aminoiminomethyl)hydrazono]-methyl]-3-cephem-4-carboxylic acid 1-(isopropoxycarbonyloxy)ethyl ester is obtained in the form of a yellow diastereomeric mixture in the ratio of ca. 1:1.

EXAMPLE 147

Ditosylate of 6R-trans(Z)-7-[(2-amino-4-thiazolyl) (hydroxyimino)acetyl]amino-3-[[(aminoiminomethyl)hydrazono]methyl]-3-cephem-4-carboxylic acid(isopropoxycarbonyloxy)ethyl ester A solution of 0.6 g of a compound obtained according to Example 146 in a mixture of 50 ml of acetonitrile and 20 ml of isopropanol is treated with 0.66 g of the monohydrate of toluene-4-sulfonic acid and stirred overnight at 25°. The reaction mixture is poured into 150 ml of tert.butyl-methylether. The precipitate obtained is filtered off, washed with tert.butyl-methylether and dried. The ditosylate of 6R-trans(Z)-7-[(2-amino-4-thiazolyl)(hydroxyimino)acetyl] amino-3-[[(aminoiminomethyl)hydrazono]methyl]-3-cephem-4-carboxylic acid(isopropoxycarbonyloxy)ethyl ester is obtained in the form of a light coloured diastereomeric mixture in the ratio of ca. 1:1.

EXAMPLE 148

Dihydrochloride of 7-[[(2-amino-4 thiazolyl)-(Z)-[(carboxymethoxy)imino]actyl]amino]-3-[[(aminoiminomethyl)hydrazono]methyl]-3-cephem-4-carboxylic acid (Compound of Example 5)

a) Dihydrochloride of 7-Amino-3-[[(aminoiminomethyl)hydrazono]methy]-3-cephem-4-carboxylic acid To 1.0 g of 7-amino-3-formyl-3-cephem-4-carboxylic acid in a mixture of 50 ml of acetonitrile and 5 ml of 2N HCl are added dropwise 0.6 g of the hydrogen carbonate of aminoguanidine, dissolved in 2.2 ml of 2N HCl. The dihydrochloride of 7-amino-3-[[(aminoiminomethyl)hydrazono] methyl]-3-cephem-4-carboxylic acid precipitates, is filtered off, washed with acetonitrile and dried.

b) Hydrochloride of 7-[[(2-amino-4-thiazolyl)-(Z)-[[2-(1,1-dimethylethoxy)-2-oxoetoxy]imino]acetyl] amino]-3-[[(aminoiminomethyl)hydrazono]methyl]-3-cephem-4-carboxylic acid 4 g of the dihydrochloride of 7-amino-3-[[(aminoiminomethyl)hydrazono]methyl]-3-cephem-4-carboxylic acid are dissolved in 80 ml of methanol. The solution is cooled to 0° and treated with a solution of 7 g of (2-amino-4-thiazolyl)-(Z)-[2-(1,1-dimethylethoxy)-2-oxoethoxy]imino]thioacetic acid S-benzothiazol ester in 50 ml of methylene chloride. The reaction mixture is stirred for about 2.5 hours at 20°. About a third of the solvent is evaporated off and 120 ml of ether are added to the residue. The hydrochloride of 7-[[(2-amino-4-thiazolyl)-(Z)-[[2-(1,1-dimethylethoxy)-2-oxoetoxy]imino]-acetyl]amino]-3-[[(aminoiminomethyl)hydrazono]methyl]-3-cephem-4-carboxylic acid precipitates, is filtered off, washed with ether and dried.

c) Dihydrochloride of 7-[[(2-amino-4-thiazolyl)-(Z)-[(carboxymethoxy)imino]actyl]amino]-3-[[(aminoiminomethyl)hydrazono]-3-cephem-4-carboxylic acid 3.5 g of the hydrochloride of 7-[[(2-amino-4-thiazolyl)-(Z)-[[2-(1,1-dimethylethoxy)-2-oxoetoxy]imino]acetyl]amino]-3-[[(aminoiminomethyl)hydrazono]methyl]-3-cephem-4-carboxylic acid are dissolved in 20 ml of trifluoroacetic acid at 0°. The solution is stirred for ca. 15 minutes at 0° and for ca. 1 hour at 20°. The reaction mixture is treated with 40 ml of ether. A precipitate forms, is filtered off, washed with ether, dried, dissolved in 15 ml of 2N HCl and stirred for ca. 1 hour at 20°. A light brownish precipitate of the dihydrochloride of 7-[[(2-amino-4 thiazolyl)-(Z)-[(carboxy-methoxy)imino]actyl]-amino]-3-[[(aminoiminomethyl)hydrazono]methyl]-3-cephem-4-carboxylic acid is obtained, filtered off and dried.

The compounds of Examples 1 to 146 may be obtained as described in Example 147 using the appropriate starting material.

Compounds used as starting material may be prepared as follows:

Example A)

Trifluoroacetate of N-(1,4,5a,6-tetrahydro-3-hydroxy-1,7-dioxo-3H,7H-azeto[2,1-b]furo[3,4-d][1,3]-thiazin-6-yl)-2-(2-aminothiazol-4-yl)-(Z)-2-methoxyiminoacetic acid amide a) Hydrochloride of 6-amino-1,4,5a,6-tetrahydro-3-hydroxy-1,7-dioxo-3H,7H-aceto[2,1-b]furo[3,4-d][1,3]thiazin(hydroxylactone of the hydrochloride of 7-amino-3-formyl-3-cephem-4-carboxylic acid)

13.8 g of the hydrochloride of 7-amino-3-[(Z/E)-prop-1-en-1-yl]-3-cephem-4-carboxylic acid are dissolved in 200 ml of methanol. The solution is cooled to −50° and 8 l of $O_2$ containing ca. 2 percent v/v ozone are introduced per minute under stirring at this temperature. After ca. 20 minutes the hydrochloride of 6-amino-1,4,5a,6-tetrahydro-3-hydroxy-1,7-dioxo-3H,7H-aceto[2,1-b]furo[3,4-d][1,3]thiazin being practically quantitatively formed and ozonolysis is terminated as determined by HPLC. 8 l of $N_2$ are bubbled through the reaction mixture within ca. 2 minutes. The slight cloudy solution is poured into 1400 ml of tert.butyl-methyl ether. The precipitate is filtered off under $N_2$, washed with a little of tert.butyl-methyl ether and acetonitrile and dried. The hydrochloride of 6-amino-1,4,5a,6-tetrahydro-3-hydroxy-1,7-dioxo-3H,7H-aceto[2,1-b]furo[3,4-d][1,3]thiazin is obtained in the form of a white powder (HPLC content of more than 95%).

b) (6R-trans)-7-Amino-3-formyl-8-oxo-5-thia-1-azabicyclo[4.2.0]oct-2-en-2-carboxylic acid(7-amino-3-formyl-3-cephem-4-carboxylic acid)

2.64 g of the hydrochloride of 6-amino-1,4,5a,6-tetrahydro-3-hydroxy-1,7-dioxo-3H,7H-aceto[2,1-b]furo[3,4-d][1,3]thiazin are dissolved in 50 ml of methanol. To this solution a solution of 0.78 g of pyridin in 10 ml of methanol is added dropwise under ice cooling and stirring. The precipitate obtained is filtered off moisture free under nitrogen, washed with a little methanol and dried. (6R-trans)-7-Amino-3-formyl-8-oxo-5-thia-1-azabicyclo[4.2.0]oct-2-en-2-carboxylic acid is obtained in the form of a light brownish powder.

IR (KBr): 1799 $cm^{-1}$ (β-lactam), 1672 $cm^{-1}$ (CHO), 1606 and 1542 $cm^{-1}$ (carboxylate)

UV-Spectrum: $\lambda_{max}$ in $H_2O$=302 nm.

c) N-(1,4,5a,6-Tetrahydro-3-hydroxy-1,7-dioxo-3H,7H-azeto[2,1-b]furo[3,4-d[]1,3-thiazin-6-yl)-2-(2-tritylaminothiazol-4yl)-(Z)-2-methoxyiminoacetic acid amide 10 g of 7-amino-3-formyl-3-cephem-4-carboxylic acid in 200 ml of acetonitrile methylenchloride (1:1) are treated with 37.4 ml of N,O-bis(trimethylsilyl)acetamide at room temperature within ca. 5 minutes. After ca. 30 minutes the reaction mixture is cooled to −10° and 21 g of 2-(2-tritylaminothiazol-4-yl)-(Z)-2-methoxyiminoacetic acid chloride are added in 3 portions. The temperature raises to −5°. After ca. 45 minutes the reaction mixture is treated with 4 ml of water. The temperature raises to 20°. The reaction mixture is stirred for ca. 10 minutes and filtered. 15 g of active charcoal are added to this filtrate and stirring is continued for ca. 10 minutes. After filtration the solvent of the filtrate obtained is evaporated. The evaporation residue is treated with tert.butyl-methyl ether. A crystalline, almost colourless precipitate is obtained, filtered off and dried. Crystalline N-(1,4,5a,6-Tetrahydro-3-hydroxy-1,7-dioxo-3H,7H-azeto[2,1-b]furo[3,4-d][1,3]thiazin-6-yl)-2-(2-tritylaminothiazol-4-yl)-2-methoxyiminoacetic acid amide is obtained in form of a diastereomeric mixture in the ratio of ca. 1:1.

d) Trifluoroacetate of N-(1,4,5a,6-tetrahydro-3-hydroxy-1,7-dioxo-3H,7H-azeto[2,1-b]furo[3,4-d][1,3]thiazin-6-yl)-2-(2-aminothiazol-4-yl)-(Z)-2-methoxyiminoacetic acid amide 5 g of N-(1,4,5a,6-tetrahydro-3-hydroxy-1,7-dioxo-3H,7H-azeto[2,1-b]furo[3,4-d][1,3]-thiazin-6-yl)-2-(2-aminothiazol-4-yl)-2-methoxyiminoacetic acid amide are introduced into 20 ml of trifluoro acetic acid at 0°. The temperature raises to 10°. The reaction mixture is stirred for ca. 30 minutes at 0° and added dropwise into 200 ml of diethylether. The mixture obtained is stirred for ca. 5 minutes and filtered. A crystalline, diastereomeric mixture of the trifluoroacetate of N-(1,4,5a,6-tetrahydro-3-hydroxy-1,7-dioxo-3H,7H-azeto[2,1-b]furo[3,4-d][1,3]thiazin-6-yl)-2-(2-aminothiazol-4-yl)-2-methoxyiminoacetic acid amide in the ratio of ca. 1:1 is obtained.

Example B)

Trifluoroacetate of N-(1,4,5a,6-tetrahydro-3-hydroxy-1,7-dioxo-3H,7H-azeto[2,1-b]furo[3,4-d][1,3]-thiazin-6 yl)-(Z)-2-(2-aminothiazol-4-yl)-2-(hydroxyimino)acetic acid amide is obtained in form of a light yellow powder analogously as described in Example A) c) to d) but using in step c) 2-(2-tritylaminothiazol-4-yl)-(Z)-2-hydroxyimino acetic acid chloride instead of 2-(2-tritylaminothiazol-4-yl)-(Z)-2-methoxyimino-acetic acid chloride.

Example C)

Hydrochloride of N-(1,4,5a,6-tetrahydro-3-hydroxy-1,7-dioxo-3H,7H-azeto[2,1-b]furo[3,4-d][1,3]-thiazin-6-yl)-2-(5-amino-1,2,4-thiadiazol-3-yl)-(Z)-2-(fluoromethoxyimino)acetic acid amide A suspension of 3.73 g of 7-amino-3-formyl-3-cephem-4-carboxylic acid in a mixture of 80 ml of methylenchloride and 30 ml of acetonitrile is stirred at 0° with 16 ml of N,O-bis(trimethylsilylacetamide). Within ca.15 minutes a clear solution is obtained to which 3.9 g of (5-amino-1,2,4-thiadiazol-3-yl)-(Z)-2-fluormethoxyiminoacetic acid chloride, obtainable for example as described in Example 1 of EP-0 590 681, are added. The reaction mixture is stirred for ca. 1 hour at 0°. 500 ml of acetonitrile containing 10 g of water are added and the mixture is filtered to remove insolubles. The filtrate is evaporated. The residue is treated with 500 ml of acetonitrile, the mixture is filtered and the filtrate is evaporated. The solid obtained is treated with tert.butyl-methyl ether and dried. The hydrochloride of N-(1,4,5a,6-Tetrahydro-3-hydroxy-1,7-dioxo-3H,7H-azeto[2,1-b]furo[3,4-d][1,3]-thiazin-6-yl)-2-(5-amino-1,2,4-thiadiazol-3-yl)-(Z)-2-(fluoro-methoxyimino)acetic acid amide is obtained in the form of a light brownish powder.

Example D)

Hydrochloride of N-(1,4,5a,6-tetrahydro-3-hydroxy-1,7-dioxo-3H,7H-azeto[2,1-b]furo[3,4-d][1,3]-thiazin-6-yl)-2-(2-aminothiazol-4-yl)-(Z)-2-(acetoxyimino)acetic acid amide 40 g of 7-amino-3-formyl-3-cephem-4-carboxylic acid are suspended in 1500 ml of acetonitrile and cooled to 0°. Within ca. 20 minutes 170 ml of N,O-bis(trimethylsilyl)acetamide are added under stirring. Within ca.15 minutes at 0° a clear solution is obtained, which is cooled to −10° and to which 48 g of (2-aminothiazol-4-yl)-(Z)-(acetoxyimino)acetic acid chloride are added in portions in such a way that the temperature of the reaction mixture does not exceed −8°. Stirring is continued for ca. 60 minutes at −10° and 168 ml of water are added. Stirring is continued for ca. further 20 minutes at 0° and for ca. 2 hours at room temperature. A crystalline precipitate forms, is filtered off, washed with ca. 350 ml of acetonitrile and ca. 100 ml of ether and dried. The hydrochloride of N-(1,4,5a,6-tetra-hydro-3-hydroxy-1,7-dioxo-3H,7H-azeto[2,1-b]furo-[3,4-d][1,3]-thiazin-6-yl)-2-(2-aminothiazol-4-yl-(Z)-2-(acetoxyimino)acetic acid is obtained in form of a diastereomeric mixture in the ratio of ca. 1:1.

Example E)

Hydrochloride of N-(1,4,5a,6-tetrahydro-3-hydroxy-1,7-dioxo-3H,7H-azeto[2,1-b]furo[3,4-d][1,3]-thiazin-6-yl)-2-(2-aminothiazol-4-yl)-(Z)-2-(hydroxyimino)acetic acid amide 10 g of the hydrochloride of N-(1,4,5a,6-tetrahydro-3-hydroxy-1,7-dioxo-3H,7H-azeto[2,1-b]furo[3,4-d][1,3] thiazin-6-yl)-2-(2-aminothiazol-4-yl)-(Z)-2-(acetoxyimino)acetic acid amide are suspended in 160 ml of acetonitrile and treated with 53 ml of water and 11 ml of 8 N HCl. The reaction mixture is stirred for ca. 14 hours at room temperature. A clear solution is obtained which is diluted with water-free acetonitrile to obtain the 3-fold volume. The solvent is evaporated off to obtain a volume of ca. 10 ml, which is treated with ca. 200 ml of acetonitrile. A precipitate forms which is treated with ether, filtered off and dried. The hydrochloride of N-(1,4,5a,6-tetrahydro-3-hydroxy-1,7-dioxo-3H,7H-azeto[2,1-b]furo[3,4-d][1,3]-thiazin-6-yl)-2-aminothiazol-4-yl)-(Z)-2-(hydroxyimino)acetic acid amide is obtained in yellowish coloured form.

Example F)

Trifluoracetate of N-(1,4,5a,6-tetrahydro-3-hydroxy-1,7-dioxo-3H,7H-azeto[2,1-b]furo[3,4-d][1,3-]-thiazin-6-yl)-2-(2-aminothiazol-4-yl)-(Z)-2-[(-carboxy-1-methylethoxy)imino]acetic acid amide is obtained in form of a light brownish powder analogously as described in Example A) a) to c) but using 2-(2-tritylaminothiazol-4-yl)-(Z)-2-[(1-carboxy-1-methylethoxy)-iminoacetic acid chloride instead of 2-(2-tritylaminothiazol-4-yl)-(Z)-2-methoxyimino-acetic acid chloride.

Example G)

N-(1,4,5a,6-Tetrahydro-3-hydroxy-1,7-dioxo-3H,7H-azeto[2,1-b]furo[3,4-d][1,3]-thiazin-6-yl)-2-[2-(tert.-butoxycarbonylamino)thiazol-4-yl]-(Z)-2-pentenoic acid amide is obtained in form of a light brownish powder analogously as described in Example A) c) to d) but using 2-(2-(tert.butoxycarbonylamino)thiazol4-yl)-(Z)-2-pentenoic acid chloride instead of 2-(2-tritylaminothiazol-4-yl)-(Z)-2-methoxyimino-acetic acid chloride.

Example H)

Dihydrochloride of 1-(hydrazinoiminomethyl)piperazine a) Hydroiodide of 4-formyl-1-imino(methylthio)methyl]piperazine 25.5 g of 4-formyl-1-piperazinecarbothioamide are suspended in 80 ml of methanol, treated with 22 g of methyliodide and refluxed. Within ca.10 minutes a clear solution is obtained. The mixture is cooled to room temperature. The solvent is evaporated. Crystalline hydroiodide of 4-formyl-1-[imino(methylthio)methyl]piperazine is obtained.

b) Hydrochloride of 4-formyl-1-(hydrazinoiminomethyl)piperazine 48.1 g of the hydroiodide of 4-formyl-1-[imino(methylthio)methyl]piperazine are dissolved in 100 ml of water, run through a column filled with 800 ml of a strong basic ion exchanger in chloride form and eluated with 850 ml of water. The solvent is evaporated to obtain a volume of ca. 100 ml which is treated with 7.35 g of hydrazinehydrate. The reaction mixture is stirred for ca. 1 hour at room temperature and the solvent is evaporated off. The oily hydrochloride of 4-formyl-1-(hydrazinoiminomethyl)piperazine crystallizes on drying.

c) Dihydrochloride of 1-(hydrazinoiminomethyl)piperazine 11 g of the hydrochloride of 4-formyl-1-(hydrazinoiminomethyl)piperazine are dissolved in 400 ml of methanol and treated with 50 of $HCl_{conc.}$. The reaction mixture is stirred for ca. 14 hours at room temperature. A white precipitate forms, is filtered off, washed with methanol and ether, dried and recrystallized with water/ethanol. The dihydrochloride of 1-(hydrazinoiminomethyl)-piperazine is obtained in crystalline, colourless form.

Analogous in the manner as described in Example H) compounds of formula IV of TABLE 2 may be obtained:

TABLE 2

| Ex. | R₂ | Salt | Process |
|---|---|---|---|
| I) | pyrrolidine-N-C(=N-C₂H₅)-NH-NH₂ | HCl | H) a) to c) |
| J) | morpholine-N-C(=N-CH₃)-NH-NH₂ | HCl | H) a) to c) |
| K) | (CH₃)₃C-NH-C(=NH)-NH-NH₂ | HCl | H) a) to c) |
| L) | CH₃-N(piperazine)N-C(=NH)-NH-NH₂ | 2HCl | H) a) to c) |
| M) | (CH₃)₃-N⁺-(CH₂)₂-NH-C(=N-CH₃)-NH-NH₂ | 2HCL | H) a) to c) |
| N) | OHC-N(piperazine)N-C(=N-CH₃)-NH-NH₂ | HCl | H) a) to b) |
| O) | HN(piperazine)N-C(=N-CH₃)-NH-NH₂ | 3HCl | H) c) |

Example P)

1-Amino-3-(2-hydroxyethyl)-4-methylguanidine 12.7 g of 2-methylamino-2-oxazoline ar dissolved in 50 ml of water, treated with 3 g of hydrazinehydrate and stirred for ca. 17 hours at room temperature. The solvent is evaporated and 1-amino-3-(2-hydroxyethyl)-4-methylguanidine is obtained as oily residue crystallizing upon cooling.

Example Q)

Hydrochloride of 1,1-dimethyl-4-(hydrazinoiminomethyl)piperaziniumchloride a) Hydroiodide of 1,1-dimethyl-4-[imino(methylthio)methyl]piperaziniumiodide 3.2 g of 4-methyl-1-piperazinecarbothioaride are suspended in 100 ml of methanol. 6.2 g of methyliodide are added and the mixture is refluxed for ca. 2 hours and cooled to 20° ab. The hydroiodide of 1,1-dimethyl-4-[imino(methylthio)methyl]piperaziniumiodide precipitates, is filtered off and dried.

b) Hydrochloride of 1,1-dimethyl-4-(hydrazinoiminomethyl)piperaziniumchloride 6.57 g of the hydroiodide of 1,1-dimethyl-4-[imino(methylthio)methyl]piperaziniumiodide are dissolved in 70 ml of water, run through a column filled with 150 ml of a strong basic ion exchanger in chloride form and eluated with 250 ml of water. Water is evaporated off the eluate to obtain to a volume of ca. 50 ml, which is treated with 0.9 ml of hydrazinehydrate and stirred overnight. The solvent is evaporated off and the residue obtained is treated with n-hexane. The hydrochloride of 1,1-dimethyl-4-(hydrazinoiminomethyl)piperaziniumchloride is obtained.

Example R)

Trihydrochloride of 1-[hydrazino(methylimino)methyl]piperazine a) Hydrochloride of S-methyl-2-methylisothiosemicarbazide A solution of 239.8 g of the hydroiodide of S-Methyl-2-methylisothiosemicarbazide in 100 ml of water is run through a column filled with 1500 ml of a strong basic ion exchanger in chloride form and eluated with water. The eluate is lyophilized and the lyophilizalion residue is treated with ether. The precipitate is filtered off and dried. The hydrochloride of S-methyl-2-methylisothiosemicarbazide is obtained as a white solid.

Melting point: 116° b) Hydrochloride of 4-formyl-1-[hydrazino(methylimino)methyl]piperazine

A mixture of 20 g of freshly distilled formylpiperazine and 27.3 g of the hydrochloride of S-methyl-2-methylisothiosemicarbazide in 250 ml of ethanol is refluxed overnight and the solvent is evaporated. The oily residue is dissolved in 70 ml of hot isopropanol and the solution is slowly cooled to 20°. A precipitate forms and the mixture is allowed to stand for ca. 2 hours at 40. The hydrochloride of 4-formyl-1-[hydrazino(methylimino)methyl]piperazine is filtered off and recrystallized from isopropanol.

c) Trihydrochloride of 1-[hydrazino(methylimino)methyl]piperazine 10 g of the hydrochloride of 1-formyl-4-[hydrazino(methylimino)methyl]piperazine are dissolved in 250 ml of methanol. 50 ml of $HCl_{conc.}$ are added, the mixture obtained is stirred overnight and the solvent is evaporated. A solid residue is obtained which is dried over solid KOH. The trihydrochloride of 1-[hydrazino(methylimino)methyl]piperazine is obtained in form of a white product.

In analogous manner as described in Example R) but reacting the hydrochloride of S-methyl-isothiosemicarbazide or the hydrochloride of S-methyl-2-methylisothiosemicarbazide or the hydrochloride of S-methyl-4-methylisothiosemicarbazide with a corresponding amine compounds of formula IV of TABLE 3 may be obtained.

TABLE 3

| Ex. | R₂ | Salt |
|---|---|---|
| S) | CF₃CH₂-NH-C(=NH)-NH-NH₂ | HCl |

TABLE 3-continued

| Ex. | R₂ | Salt |
|---|---|---|
| T) | 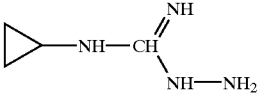 | HCl |
| U) | 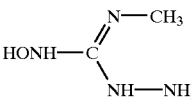 | HCl |
| V) | 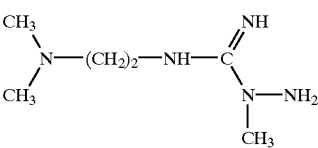 | 2HCl |

Example W)

Hydrochloride of 1-Amino-3-(3,4-dihydroxybenzylidenamino)guanidine 1 g of the hydrochloride of diaminoguanidine are dissolved in 10 ml of 4 N HCl and diluted with 20 ml of methanol. This solution is treated quickly with a solution of 1 g of 3,4-dihydroxybenzaldehyde in 40 ml of methanol. The reaction mixture is stirred for some minutes at room temperature and the solvent is evaporated off. The residue is suspended in 50 ml of acetonitrile. The precipitate formed is filtered off and dried. The hydrochloride of 1-amino-3-(3,4-dihydroxybenzylidenamino)guanidine is obtained.

Example X)

Hydroiodide of S-Methyl-4-cyclopropylthiosemicarbazide 295 mg of 4-cyclopropylthiosemicarbazide are dissolved in 5 ml of dry methanol and treated with 154 ml of methyliodide. The mixture is stirred at 400 under nitrogen for ca. 5 hours, cooled and treated with diethylether. A colourless precipitate of the hydroiodide of S-Methyl-4-cyclopropylthiosemicarbazide is formed, filtered off, washed with diethylether and dried.

Example Y)

Hydroiodide of S-methyl-4-n-butylthiosemicarbazide 147 mg of 4-n-butylthiosericarbazide in 2.5 ml of dry methanol are treated with 149 mg of methyliodide. The mixture is stirred under nitrogen for ca. 5 hours, cooled and treated with diethylether. A colourless precipitate of the hydroiodide of S-methyl-4-n-butylthiosericarbazide is formed, filtered off, washed with diethylether and dried.

Example Z)

1-Methyl-5-mercapto-1,2,4-triazol-3-carboxylic acid hydrazide 0.48 g of 1-methyl-5-mercapto-1,2,4-triazol-3-carboxylic acid methyl ester are dissolved in 10 ml of methanol, treated with 450 µl of hydrazinehydrate and stirred for ca. 2 hours at 20°. A precipitate of 1-methyl-5-mercapto-1,2,4-triazol-3-carboxylic acid hydrazide is formed, filtered off, washed with methanol and dried.

IR (KBr): 1669 cm⁻¹, 1608 cm⁻¹, 1517 cm⁻¹

$^{13}$C-NMR (300 MHz, DMSO-$d_6$): 35.4 (NCH₃); 143.3, 154.3 and 166.7

Example AA)

Hydroiodide of 1,5-dimethyl-2-(hydrazinoiminomethyl)pyrrol a) 1,5-Dimethylpyrrol-2-carbothioamide 5 g of 2-cyano-1,5-dimethylpyrrol are dissolved in 40 ml of ethanol and treated with 10 ml of triethylamine. 50 ml of an ethanolic H₂S solution (3.8 g/100 ml) are added and the mixture is heated for ca. 15 hours in an autoclave at 70°. The reaction mixture is cooled and the solvent is evaporated off to obtain ca. a quarter of its volume. 1,5-dimethylpyrrol-2-carbothioamide crystallizes upon cooling at 0° in the form of a light yellow precipitate.

b) Hydroiodide of 1,5-dimethyl-2-[imino(methylthio)methyl]pyrrol 1 g of 1,5-dimethylpyrrol-2-carbothioamide are dissolved in 20 ml of methanol and treated with 1.7 g of methyliodide. The reaction mixture is stirred for about 5 hours at room temperature. The solvent is evaporated until crystallization starts. The residue is cooled to ca. 0°. The crystalline hydroiodide of 1,5-dimethyl-2-[imino(methylthio)methyl]pyrrol is filtered off, washed with methanol and dried.

c) Hydroiodide of 1,5-dimethyl-2-(hydrazinoiminomethyl)pyrrol 1.3 g of the hydroiodide of 1,5-dimethyl-2-[imino(methylthio)methyl]pyrrol are dissolved in 20 ml of methanol. 0.28 g of hydrazinehydrate are added. The reaction mixture is stirred for ca. 3 hours, the solvent is evaporated off and the residue is recrystallized from acetonitrile/ether. The hydroiodide of 1,5-dimethyl-2-(hydrazinoiminomethyl)pyrrol is obtained.

Example AB)

Hydroiodide of 3,4-dihydroxy-2-(hydrazinoimino methyl)benzene is obtained in analogous manner as described in Example AA), but using 3,4-dihydroxy-thiobenzamide instead of 1,5-dimethylpyrrol-2-carbothioamide.

Example AC)

7-Amino-3-[[(carboxymethoxy)imino]methyl]-3-cephem-4-carboxylic acid

A solution of 1.86 g of the hydrochloride of aminooxy-acetic acid in 20 ml of water is treated under stirring at 0° with 3.16 g of the hydrochloride of 6-amino-1,4,5a,6-tetrahydro-3-hydroxy-1,7-dioxo-3H,7H-azeto[2,1-b]furo[3,4-d][1,3]thiazin. The mixture is stirred for ca. 8 hours at 0°. 7-Amino-3-[[(carboxymethoxy)imino]methyl]-3-cephem-4-carboxylic acid precipitates in form of colourless crystals, which are filtered off, washed with 5 ml of cold water and 5 ml of acetone and dried.

Example AD)

7-Amino-3-[(methoxyimino)methyl]-3-cephem-4-carboxylic acid

A solution of 0.5 g of the hydrochloride of O-methylhydroxylamine in 10 ml of water is treated under stirring at 0° with 1.38 g of 7-amino-3-formyl-3-cephem-4-carboxylic acid and stirred for ca. 8 hours at 0°. 7-Amino-3-[(methoxyimino)methyl]-3-cephem-4-carboxylic acid precipitates in form of almost white crystals, which are filtered off, washed with 5 ml of cold water and 5 ml of acetone and dried.

Example AE)

7-Amino-3-[(hydroxyimino)methyl]-3-cephem-4-carboxylic acid a) A solution of 1.26 g of the hydrochloride of hydroxylamine in 7.5 ml of water is treated under stirring at 0° with 4.74 g of the hydrochloride of 6-amino-1,4,5a,6-tetrahydro-3-hydroxy-1,7-dioxo-3H,7H-azeto[2,1-b]furo[3,4-d][1,3]thiazin and stirred for ca. 8 hours at 0° under nitrogen. The pH of the reaction mixture is adjusted to 3.5 using solid sodium hydrogen carbonate. 7-Amino-3-[(hydroxyimino)methyl]-3-cephem-4-carboxylic acid precipitates in form of colourless crystals, which are filtered off, washed with ca. 5 ml of cold water and 5 ml of acetone and dried.

b) A suspension of 0.79 g of the hydrochloride of 6-amino-1,4,5a,6-tetrahydro-3-hydroxy-1,7-dioxo-3H,7H-azeto[2,1-b]furo[3,4-d][1,3]thiazin in 10 ml of dichloromethane is treated under stirring at 4° with 2.67 g of N,O-bis-(trimethylsilyl)acetamide. A clear solution is obtained within 10 minutes. 0.21 g of the hydrochloride of hydroxylamine are added. The reaction mixture is stirred for ca. 2 hours under nitrogen at 4° and the solvent is evaporated off. The residue is treated with 10 ml of isopropylalkohol, precooled to 1°. 7-Amino-3-[(hydroxyimino)methyl]-3-cephem-4-carboxylic acid precipitates in form of almost colourless crystals which are filtered off, washed with 5 ml of acetone and dried.

Analoguously as described in Examples AC) to AE) the compounds of Table 4 of formula VI may be obtained.

TABLE 4

| Bsp: | $R_1$ | $R_2$ | Salz |
|---|---|---|---|
| AF) | H | —NH—C(=NH)—NH$_2$ | 2HCl |
| AG) | H | —NH—CO—NH$_2$ | 2HCl |
| AH) | H | —NH—CS—NH$_2$ | 2HCl |
| AI) | H | —NH—C(=NH)—S—CH$_3$ | HCl |
| AJ) | H | —NH—C(=NH)—NH—CH$_3$ | 2HCl |
| AK) | H | —NH—C$_6$H$_5$ | H$_2$N—NH—C$_6$H$_5$ |

$^1$H-NMR-Spectra of the Compounds Obtained According to the Examples (Ex.)

Ex. Spectrum 1 (300 MHz, CD$_3$OD): 8.43 (s, 1H, CH=N); 6.96 (s, 1H, CH); 5.99 (d, J=4.9 Hz, 1H, CH); 5.22 (d, J=4.9 Hz, 1 H, CH); 4.04 (s, 3H, OCH$_3$); 3.99 and 3.56 (AB quartet, J=17.8 Hz, 2H, SCH$_2$).

2 (90 MHz, DMSO-d$_6$+D$_2$O): 3.6 and 4.3 (AB quartet, J=18 Hz, 2H, SCH$_2$); 5.3 (d, J=5.1 Hz, 1H, β-lactam-H); 5.95 (d, J=5.1 Hz, 1H, β-lactam-H); 6.95 (s, 1H, thiazolyl-H); 8.35 (s, 1H, CH=N).

3 (300 MHz, CD$_3$OD): 7.97 (s, 1H, CH=N); 6.84 (s, 1H, CH); 5.69 (d, J=4.9 Hz, 1H, CH); 5.13 (d, J=4.9 Hz, 1H, CH); 4.13 and 3.93 (AB quartet, J=16.8 Hz, 2H, SCH$_2$), 3.81 (s, 3H, OCH$_3$); 3.67 (s, 3H, OCH$_3$).

4 (300 MHz, CD$_3$OD): 8.36 (s. 1H, CH=N); 6.87 (s, 1H, CH); 5.88 (d, J=4.9 Hz, 1H, CH); 5.29 (d, J=4.9 Hz, 1H, CH); 4.00 (s, 3H, OCH$_3$); 3.95 and 3.60 (AB quartet, J=17.8 Hz, 2H, SCH$_2$).

5 (300 MHz, DMSO-d$_6$): 3.57 and 4.43 (AB quartet, J=18.2 Hz, 2H, S—CH$_2$); 4.71 (s, 2H, O—CH$_2$); 5.30 (d, J=5.0 Hz, 1H, β-lactam-H); 5.91 (dd, J=5.0 and 7.9 Hz, 1H, β-lactam-H); 7.02 (s, 1H, CH thiazol); 7.9 (broad 4H, NH); 8.29 (s, 1H, CH=N); 9.88 (d, J=7.9 Hz, 1H, NH); 12.25 (s, 1H, OH).

6 (300 MHz, CD$_3$OD): 8.10 (s, 1H, CH=N); 7.01 (s, 1H, CH); 5.84 (d, J=4.9 Hz, 1H, CH); 5.29 (d, J=4.9 Hz, 1 H, CH); 3.98 (s, 3H, OCH$_3$); 3.96 and 3.59 (AB quartet, J=16.8 Hz, 2H, SCH$_2$).

7 (300 MHz, CD$_3$OD): 8.26 (s, 1H, CH=N); 7.04 (s, 1H, CH); 5.90 (d, J=5.1 Hz, 1H, CH); 5.24 (d, J=5.1 Hz, 1 H, CH); 4.05 (s, 3H, OCH$_3$); 4.32 and 3.65 (AB quartet, J=17.8 Hz, 2H, SCH$_2$).

8 (300 MHz, CD$_3$OD): 8.46 (s, 1H, CH=N); 6.99 (s, 1H, CH); 5.95 (d, J=5.2 Hz, 1H, CH); 5.27 (d, J=5.2 Hz, 1 H, CH); 4.01 (s, 3H, OCH$_3$); 4.37 and 3.63 (AB quartet, J=18.1 Hz, 2H, SCH$_2$); 2.95 (s, 3H, N—NH$_3$).

9 (90 MHz, DMSO-d$_6$): 9.78 (d, J=8.0 Hz, 1H, CONH); 8.26 (s, 1H, CH=N); 6.91 (s, 1H, CH); 7.32 (dd, J=7.3 Hz, 2H, H$_m$); 7.05 (d, J=7.3 Hz, 2H, H$_o$); 6.78 (t, J=7.3 Hz, 1H, H$_p$); 5.76 (dd, J$_1$=4.8 Hz, J$_2$=8.0 Hz, 1H, CH); 5.25 (d, J=4.8 Hz, 1 H, CH); 3.91 (s, 3H, OCH$_3$); 4.16 and 3.76 (AB quartet, J=17.4 Hz, 2H, SCH$_2$).

10 (90 MHz, DMSO-d$_6$): 2.25 (s, 3H, CH$_3$CO); 3.65 and 4.55 (AB quartet, J=18 Hz, 2H, SCH$_2$); 5.4 (d, J=5 Hz, 1 H, β-lactam-H); 5.95 (dd, J=5 Hz and 8 Hz, 1H, β-lactam-H); 7.32 (s, 1H, thiazolyl-H); 8.4 (s, 1H, CH=N); 10.2 (d, J=8.0 Hz, 1H, NH).

11 (90 MHz, DMSO-d$_6$): 1.12 (t, J=7.1 Hz, 3H, CH$_3$); 3.29 (q, 2H, CH$_2$); 3.56 and 4.50 (AB quartet, J=18.1 Hz, 2H, SCH$_2$); 3.93 (s, 3H, N—O—CH$_3$); 5.30 (d, J=5 Hz, 1H, CH); 5.9 (q, J=6 Hz, and 8 Hz, 1H, CH); 6.90 (s, 1H, thiazolyl-H); 8.32 (s, 1H, CH=N); 9.86 (d, J=8.0 Hz, NH).

12 (90 MHz, DMSO-d$_6$): 1.85–2.15 (m, 4H); 3.25–3.7 (m, SH, —CH$_2$—N—NH$_2$— and 1H of SCH$_2$); 4.0 (s, 3H, N—O—CH$_3$); 4.5 (part of the AB quartet, J=18 Hz, 1H of SCH$_2$); 5.3 (d, J=5 Hz, 1H, CH); 5.9 (q, J=5 Hz and 8 Hz, 1H, CH); 7.0 (s, 1H, thiazolyl-H); 8.8 (s, 1H, CH=N); 10.1 (d, J=7.9 Hz, NH).

13 (90 MHz, DMSO-d$_6$): 2.9 (broad s, 6H, N—NH$_3$), 3); 3.6 and 4.5 (AB quartet, J=18 Hz, 2H, SCH$_2$); 3.9 (s, 3H, N—O—CH$_3$); 5.3 (d, J=5 Hz, 1H, CH)); (q, J=5 Hz and 8 Hz, 1H, CH); 6.95 (s, 1H, thiazolyl-H); 8.75 (s, 1H, CH=N); 9.95 (d, J=8 Hz, NH).

14 (90 MHz, DMSO-d$_6$): 3.65 (broad s, 4H, N—NH$_2$—CH$_2$—N); 3.5 and 4.4 (AB quartet, J=18 Hz, 2H, SCH$_2$); 3.9 (s, 3H, N—O—CH$_3$); 5.3 (d, J=5.0 Hz, 1H, CH); 5.85 (q, J=5 Hz and 8 Hz, 1H, CH); 6.9 (s, 1H, thiazolyl-H); 8.35 (s, 1H, CH=N); 9.9 (d, J=8 Hz, NH).

15 (90 MHz, DMSO-d$_6$): 1.16 (t, J=7.1 Hz, 3H, CH$_3$); 1.8–2 (m, 4H); 3.32 (q, 2H, CH$_2$); 3.45–3.65 (m, 5H, —CH$_2$—N—NH$_2$— and 1H of SCH); 3.91 (s, 3H, N—O—

$CH_3$); 4.1 (part of the AB quartet, J=18 Hz, 1H of $SCH_2$); 5.27 (d, J=5 Hz, 1H, CH); 5.9 (q, J=5 Hz and 8 Hz, 1H, CH); 6.86 (s, 1H, thiazolyl-H); 8.56 (s, 1H, CH=N); 9.82 (d, J=8 Hz, NH).

16 (90 MHz, DMSO-$d_6$): 2.86 (broad s, 3H, N—$NH_3$); 3.5 and 4.5 (AB quartet, J=18 Hz, 2H, $SCH_2$); 5.3 (d, J=6 Hz, 1H, CH); 5.9 (q, J=5 Hz and 8 Hz, 1H, CH); 6.85 (s, 1H, thiazolyl-H); 8.4 (s, 1H, CH=N); 9.8 (d, J=8 Hz, NH).

17 (90 MHz, DMSO-$d_6$): 1.85–2.15 (m, 4H); 3.25–3.8 (m, 5H, —$CH_2$—N—$NH_2$— and 1H of $SCH_2$); 4.5 (part of the AB quartet, J=18 Hz, 1H of $SCH_2$); 5.3 (d, J=5 Hz, 1H, CH); 5.85 (q, J=5 Hz and 8 Hz, 1H, CH); 6.85 (s, 1H, thiazolyl-H); 8.7 (s, 1H, CH=N); 9.8 (d, J=7.9 Hz, NH).

18 (90 MHz, DMSO-$_6$): 2.86 (broad s, 6H, N—$NH_3$, 3); 3.55 and 4.47 (AB quartet, J=18.9 Hz, 2H, $SCH_2$); 5.31 (d, J=5.1 Hz, 1H, CH); 5.91 (q, J=5.1 Hz and 7.9 Hz, 1H, CH); 6.8 (s, 1H, thiazolyl-H); 8.58 (s, 1H, CH=N); 9.72 (d, J=7.9 Hz, NH).

19 (90 MHz, DMSO-$d_6$): 3.7 (broad s, 4H, N—$NH_2$—$CH_2$—N); 3.55 and 4.35 (AB quartet, J=18.1 Hz, 2H, $SCH_2$); 5.31 (d, J=5.0 Hz, 1H, CH); 5.9 (q, J=5.1 Hz and 8 Hz, 1H, CH); 6.8 (s, 1H, thiazolyl-H); 8.38 (s, 1H, CH=N); 9.73 (d, J=8.0 Hz, NH).

20 (300 MHz, $CD_3OD$): 8.34 (s, 1H, CH=N); 7.06 (s, 1H, CH); 5.93 (d, J=4.9 Hz, 1H, CH); 5.32 (d, J=4.9 Hz, 1 H, CH); 4.09 (s, 3H, $OCH_3$); 4.33 and 3.64 (AB quartet, J=18.2 Hz, 2H, $SCH_2$).

21 (90 MHz, DMSO-$d_6$): 3.65 and 4.7 (AB quartet, J=18 Hz, 2H, $SCH_2$); 3.95 (s, 3 H, O—$CH_3$); 4.2 (part of the AB quartet, J=18 Hz, 1H of $SCH_2$); 5.3 (d, J=5 Hz, 1 H, β-lactam-H); 5.85 (dd, J=5 Hz and 8 Hz, β-lactam-H); 7.0 (s, 1 H, thiazolyl-H); 7 to 7.7 (m, 5 H, aromatic H); 8.45 (s, 1 H, CH=N);0.9 (d, J=8 Hz, NH).

22 (90 MHz, DMSO-$d_6$):3.55 and 4.6 (AB quartet, J=18 Hz, 2H, $SCH_2$); 3.93 (s, 3 H, O—$CH_3$); 4.2 (part of the AB quartet, J=18 Hz, 1H of $SCH_2$); 5.3 (d, J=5 Hz, 1 H, β-lactam-H); 5.85 (dd, J=5 Hz and 8 Hz, β-lactam-H); 7.0 (s, 1 H, thiazolyl-H); 7 to 7.7 (m, 5 H, aromatic-H); 8.3 (s, 1 H, CH=N); 9.9 (d, J=8 Hz, NH).

23 (90 MHz, DMSO-$d_6$): 3.05 (d, J=4 Hz, 3 H, NHC$\underline{H}_3$); 3.55 and 4.5 (AB quartet, J=18 Hz, 2H, $SCH_2$); 3.93 (s, 3 H, O—$CH_3$); 4.2 (part of the AB quartet, J=18 Hz, 1H of $SCH_2$); 5.25 (d, J=5 Hz, 1 H, β-lactam-H); 5.8 (dd, J=5 Hz and 8 Hz, β-lactam-H); 6.95 (s, 1 H, thiazolyl-H); 8.25 (s, 1 H, CH=N);8.4 (d, J=4 Hz, N$\underline{H}$CH_3);9.85 (d, J=8 Hz, NH).

24 (90 MHz, DMSO-$d_6$): 2.85 (s, 3H, $NCH_3$); 3.1 to 3.7 (m, 9 H, 8 piperazinyl-H's and 1H of $SCH_2$); 3.95(s, 3 H, $OCH_3$); 4.1 (part of the AB quartet, J=18 Hz, 1H of $SCH_2$); 3.95 (s, 3 H,O—$CH_3$); 5.3 (d, J=5 Hz, 1 H, β-lactam-H); 5.85 (dd, J=5 Hz and 8 Hz, β-lactam-H);6.95 (s, 1 H, thiazolyl-H); 7.95 (s, 1 H, CH=N); 9.9 (d, J=8 Hz, NH).

25 (90 MHz, DMSO-$d_6$): 3.6 and 4.55 (AB quartet, J=18 Hz, 2H, $SCH_2$); 3.9 to 4.1 (m, 5 H, —$OCH_3$ and —N—N$\underline{H}_2$—CH=$CH_2$); 5.1 to 5.5 (m, 3 H, β-lactam-H and —N—$NH_2$—CH=C$\underline{H}_2$); 5.7 to 6.1 (m,2H, β-lactam-H and N—$CH_2$—C$\underline{H}$=$CH_2$);6.95 (s, 1 H, thiazolyl-H);8.3 (s, 1 H, CH=N); 9.95 (d, J=8 Hz, NH).

26 (90 MHz, DMSO-$d_6$): 1.7 to 2 (m, 2 H, —$CH_2$—C$\underline{H}_2$—$CH_3$); 3.1 to 3.5 (m, 4 H); 3.55 and 4.5(AB quartet, J=18 Hz, 2H, $SCH_2$); 3.95 (s, 3 H, O—$CH_3$); 5.3 (d, J=5 Hz, 1 H, β-lactam-H); 5.85 (dd, J=5 Hz and 8 Hz, β-lactam-H); 6.95 (s, 1 H, thiazolyl-H); 8.3 (s, 1 H, CH=N); 9.9 (d, J=8 Hz, NH).

27 (90 MHz, DMSO-$d_6$): 0.8 to 1.1 and 1.1 to 1.7 (m, 7 H, —$CH_2$—$CH_2$—$CH_3$); 3.15 to 3.45 (m, 2 H, —NHC$\underline{H}_2$—); 3.6 and 4.55 (AB quartet, J=18 Hz, 2H, $SCH_2$); 3.95 (s, 3 H, O—$CH_3$); 5.3 (d, J=5 Hz, 1 H, β-lactam-H); 5.85 (dd, J=5 Hz and 8 Hz, β-lactam-H); 6.95 (s, 1 H, thiazolyl-H); 8.4 (s, 1 H, CH=N); 9.95 (d, J=8 Hz, NH).

28 (90 MHz, DMSO-$d_6$): 3.05 (d, J=4 Hz, 3 H, $NHCH_3$); 3.65 (s, 3 H, $NCH_3$); 3.55 and 4.6 (AB quartet, J=18 Hz, 2H, $SCH_2$); 3.93 (s, 3 H, O—$CH_3$); 4.2 (part of the AB quartet, J=18 Hz, 1H of $SCH_2$); 5.3 (d, J=5 Hz, 1 H, β-lactam-H); 5.85 (dd, J=5 Hz and 8 Hz, β-lactam-H); 7.0 (s, 1 H, thiazolyl-H); 8.6 (s, 1 H, CH=N); 9.4 (d, J=8 Hz, NH).

29 300 MHz, DMSO-$d_6$): 2.93 (d, J=4.6 Hz, 3 H, $NCH_3$); 3.4 to 3.6 (m, 5H); 3.6 to 3.8 (m, 4H); 3.93 (s, 3 H, O—$CH_3$); 4.2 (part of the AB quartet, J=18 Hz, 1H of $SCH_2$); 5.3 (d, J=5 Hz, 1 H, β-lactam-H); 5.85 (dd, J=5 Hz and 8 Hz, β-lactam-H); 6.93 (s, 1 H, thiazolyl-H); 8.6 (s, 1 H, CH=N); 9.92 (d, J=8 Hz, NH).

30 (90 MHz, DMSO-$d_6$):1.3 (s, 9 H, —$C(CH_3)_3$); 3.55 and 4.55 (AB quartet, J=18 Hz, 2H, $SCH_2$); 5.3 (d, J=5 Hz, 1 H, β-lactam-H); 5.85 (dd, J=5 Hz and 8 Hz, β-lactam-H); 6.95 (s, 1 H, thiazolyl-H); 8.25 (s, 1 H, CH=N); 9.95 (d, J=8 Hz, NH).

31 (90 MHz, DMSO-$d_6$): 2.9 (s, 3 H, $NCH_3$); 3.0 (s, 6 H, $N(CH_3)_2$); 3.6 and 4.2 (AB quartet, J=18 Hz, 2H, $SCH_2$); 3.95 (s, 3 H, O—$CH_3$); 5.3 (d, J=5 Hz, 1 H, β-lactam-H); 5.85 (dd, J=5 Hz and 8 Hz, β-lactam-H); 7.0 (s, 1 H, thiazolyl-H); 8.55 (s, 1 H, CH=N); 9.95 (d, J=8 Hz, NH).

32 (90 MHz, DMSO-$d_6$): 2.85 (s, 2 H); 3.55 and 4.6 (AB quartet, J=18 Hz, 2H, $SCH_2$); 3.95 (s, 3 H, O—$CH_3$); 5.3 (d, J=5 Hz, 1 H, β-lactam-H); 5.85 (dd, J=5 Hz and 8 Hz, β-lactam-H); 6.95 (s, 1 H, thiazolyl-H); 8.65 (s, 1 H, CH=N); 9.9 (d, J=8 Hz, NH).

33 (90 MHz, DMSO-$d_6$): 3.4 to 3.8 (m, 9 H, morpholino H's and 1H of $SCH_2$); 3.95 (s, 3 H, O—$CH_3$); 4.6 (part of the AB quartet, J=18 Hz, 1H of $SCH_2$); 5.3 (d, J=5 Hz, 1 H, β-lactam-H); 5.85 (dd, J=5 Hz and 8 Hz, β-lactam-H); 6.95 (s, 1 H, thiazolyl-H); 8.7 (s, 1 H, CH=N); 9.9 (d, J=8 Hz, NH).

34 (300 MHz, DMSO-$d_6$): 3.32 (s, 9H,—$N^+(CH_3)_3$); 0.4 to 1 (m, 4 H, —$CH_2$—$CH_2$—); 2.5 to 2.8 (m, 1 H); 3.65 and 4.17 (AB quartet, J=18.1 Hz, 2H, $SCH_2$); 3.94 (s, 3 H, O—$CH_3$); 4.8 (q, J=17 Hz, 2H); 5.3 (d, J=5 Hz, 1 H, β-lactam-H); 5.85 (dd, J=5 Hz and 8 Hz, β-lactam-H); 6.94 (s, 1 H, thiazolyl-H); 8.26 (s, 1 H, CH=N); 9.93 (d, J=8 Hz, NH).

35 (90 MHz, DMSO-$d_6$): 0.4 to 1 (m, 4 H, —$CH_2$—$CH_2$—); 2.5 to 2.8 (m, 1 H), 3.55 and 4.6 (AB quartet, J=18 Hz, 2H, $SCH_2$); 3.95 (s, 3 H, O—$CH_3$); 5.3 (d, J=5 Hz, 1 H, β-lactam-H); 5.85 (dd, J=5 Hz and 8 Hz, β-lactam-H); 6.9 (s, 1 H, thiazolyl-H); 8.35 (s, 1 H, CH=N); 9.85 (d, J=8 Hz, NH).

36 (90 MHz, DMSO-$d_6$): 3.6 and 4.55 (AB quartet, J=18 Hz, 2H, $SCH_2$); 3.95 s, 3 H, O—$CH_3$); 5.3 (d, J=5 Hz, 1 H, β-lactam-H); 5.85 (dd, J=5 Hz and 8 Hz, β-lactam-H); 6.9 (s, 1 H, thiazolyl-H); 8.5 (s, 1 H, CH=N); 9.85 (d, J=8 Hz, NH); 10.4 (broad singulet, 1 H, —NH—O$\underline{H}$).

37 (90 MHz, DMSO-$d_6$): 3.1 (s, 3 H, N—$CH_3$); 3.55 and 4.6 (AB quartet, J=18 Hz, 2H, $SCH_2$); 3.9 (s, 3 H, O—$CH_3$); 5.3 (d, J=5 Hz, 1 H, β-lactam-H); 5.85 (dd, J=5 Hz and 8 Hz, β-lactam-H); 6.9 (s, 1 H, thiazolyl-H); 8.7 (s, 1 H, CH=N); 9.85 (d, J=8 Hz, NH).

38 (300 MHz, DMSO-$d_6$): 3.56 and 4.54 (AB quartet, J=18.1 Hz, 2H, $SCH_2$); 3.91 (s, 3 H, O—$CH_3$); 4.87 (d, J=6.5 Hz, 2 H); 5.3 (d, J=5 Hz, 1 H, β-lactam-H); 5.89 (dd, J=5 Hz and 8 Hz, β-lactam-H); 6.88 (s, 1 H, thiazolyl-H); 7.6 (m, 2 H, pyridinyl-H); 8.15 (m, 1 H, pyridinyl-H); 8.39 (s, 1 H, CH=N); 8.86 (m, 1 H, pyridinyl-H); 9.83 (d, J=8 Hz, NH).

39 (300 MHz, DMSO-$d_6$): 3.57 and 4.52 (AB quartet, J=18.1 Hz, 2H, SCH$_2$); 3.91 (s, 3 H, O—CH$_3$); 4.87 (d, J=6 Hz, 2 H); 5.3 (d, J=5 Hz, 1 H, β-lactam-H); 5.89 (dd, J=5 Hz and 8 Hz, β-lactam-H); 6.88 (s, 1 H, thiazolyl-H); 8.15 (m, 1 H, pyridinyl-H); 8.38 (s, 1 H, CH=N); 8.45 (m, 1 H, pyridinyl-H); 8.8 (m, 1 H, pyridinyl-H); 8.85 (s, 1 H, pyridinyl-H); 9.91 (d, J=8 Hz, NH).

40 (300 MHz, DMSO-$d_6$): 3.58 and 4.57 (AB quartet, J=18.3 Hz, 2H, SCH$_2$); 3.9 (s, 3 H, O—CH$_3$); 5.06 (broad singulet, 2 H); 5.3 (d, J=5 Hz, 1 H, β-lactam-H); 5.88 (dd, J=5 Hz and 8 Hz, β-lactam-H); 6.94 (s, 1 H, thiazolyl-H); 8.02 (d, J=6.6 Hz, 2 H, pyridinyl-H); 8.4 (s, 1 H, CH=N); 8.92 (d, J=6.6 Hz, 2 H, pyridinyl-H); 9.91 (d, J=8 Hz, NH).

41 (90 MHz, DMSO-$d_6$): 3.65 and 4.35 (AB quartet, J=18 Hz, 2H, SCH$_2$); 3.9 (s, 3 H, O—CH$_3$); 4.2 (d, J=7 Hz, 2H); 5.2 (d, J=5 Hz, 1 H, β-lactam-H); 5.75 (dd, J=5 Hz and 8 Hz, β-lactam-H); 6.95 (s, 1 H, thiazolyl-H); 7.85 (s, 1 H, CH=N); 9.8 (d, J=8 Hz, NH).

42 (90 MHz, DMSO-$d_6$): 2.95 (broad duplet, 3 H, N—CH$_3$); 3.0 to 3.3 (m, 4 H, —CH$_2$—N—CH$_2$); 3.4 to 3.8 (m, 5 H, —CH$_2$—NH$^+$—CH$_2$— and 1H of SCH$_2$); 3.85 (s, 3 H, O—CH$_3$); 4.1 (part of the AB quartet, J=18 Hz, 1H of SCH$_2$); 5.25 (d, J=5 Hz, 1 H, β-lactam-H); 5.85 (dd, J=5 Hz and 8 Hz, β-lactam-H); 6.8 (s, 1 H, thiazolyl-H); 8.65 (s, 1 H, CH=N); 9.75 (d, J=8 Hz, NH).

43 (90 MHz, DMSO-$d_6$): 3.7 and 4.85 (AB quartet, J=18 Hz, 2H, SCH$_2$); 3.95 (s, 3 H, O—CH$_3$); 5.35 (d, J=5 Hz, 1 H, β-lactam-H); 5.95 (dd, J=5 Hz and 8 Hz, β-lactam-H); 7.0 (s, 1 H, thiazolyl-H); 7.2 (t, J=6 Hz, 1 H, pyridinyl-H); 7.4 (d, J=8 Hz, 1 H, pyridinyl-H); 8.15 (t, J=6 Hz, 2 H, pyridinyl-H); 8.55 (s, 1 H, CH=N); 9.95 (d, J=8 Hz, NH).

44 (90 MHz, DMSO-$d_6$): 3.6 and 4.05 (AB quartet, J=18 Hz, 2H, SCH$_2$); 3.95 (s, 3 H, O—CH$_3$); 5.25 (d, J=5 Hz, 1 H, β-lactam-H); 5.75 (dd, J=5 Hz and 8 Hz, β-lactam-H); 6.9 (s, 1 H, thiazolyl-H); 8.5 (s, 1 H, CH=N); 9.85 (d, J=8 Hz, NH).

45 (300 MHz, DMSO-$d_6$): 1.4 to 1.7 (m, 6 H); 3.4 to 3.7 (m, 5 H, —CH$_2$—N—CH$_2$— and 1H of SCH$_2$); 3.92 (s, 3 H, O—CH$_3$); 4.55 (part of the AB quartet, J=18 Hz, 1H of SCH$_2$); 5.29 (d, J=5 Hz, 1 H, β-lactam-H); 5.89 (dd, J=5 Hz and 7.8 Hz, β-lactam-H); 6.89 (s, 1 H, thiazolyl-H); 8.6 (s, 1 H, CH=N); 9.84 (d, J=7.8 Hz, NH).

46 (90 MHz, DMSO-$d_6$): 3.1 to 3.4 (m, 4 H, —CH$_2$—NH$^+$—CH$_2$—); 3.65 and 4.65 (AB quartet, J=18 Hz, 2H, SCH$_2$); 3.85 (s, 3 H, O—CH$_3$); 4 to 4.3 (m, 4 H, —CH$_2$—N—CH$_2$—); 4.65 (part of the AB quartet, J=18 Hz, 1H of SCH$_2$); 5.2 (d, J=5 Hz, 1 H, β-lactam-H); 5.8 (dd, J=5 Hz and 8 Hz, β-lactam-H); 6.75 (s, 1 H, thiazolyl-H); 8.5 (s, 1 H, CH=N); 9.7 (d, J=8 Hz, NH).

47 (300 MHz, DMSO-$d_6$): 2.85 (broad singulet, 3 H, N—CH$_3$); 3.54 and 4.52 (AB quartet, J=18.1 Hz, 2H, SCH$_2$); 3.93 (s, 3 H, O—CH$_3$); 5.3 (d, J=5 Hz, 1 H, β-lactam-H); 5.89 (dd, J=5 Hz and 7.9 Hz, β-lactam-H); 6.91 (s, 1 H, thiazolyl-H); 8.62 (s, 1 H, CH=N); 9.88 (d, J=7.9 Hz, NH); 12.0 (s, 1 H, OH).

48 (90 MHz, DMSO-$d_6$): 3.2 (s, 6 H, NCH$_3$); 3.7 (s, 4 H, —N—(CH$_2$)$_2$—N—); 3.65 and 4.0 (AB quartet, J=17.8 Hz, 2H, SCH$_2$); 3.95 (s, 3 H, O—CH$_3$); 5.3 (d, J=5 Hz, 1 H, β-lactam-H); 5.85 (dd, J=5 Hz and 8 Hz, β-lactam-H); 6.95 (s, 1 H, thiazolyl-H); 8.8 (s, 1 H, CH=N); 9.9 (d, J=8 Hz, NH).

49 (300 MHz, DMSO-$d_6$): 3.7 and 4.13 (AB quartet, J=17.8 Hz, 2H, SCH$_2$); 3.9 (s, 3 H, O—CH$_3$); 5.31 (d, J=5 Hz, 1 H, β-lactam-H); 5.89 (dd, J=5 Hz, β-lactam-H); 6.92 (s, 1 H, thiazolyl-H); 8.13 (d, J=6 Hz, 2 H, pyridinyl-H); 8.7 (s, 1 H, CH=N); 8.93 (m, 3 H, pyridinyl-H); 9.88 (d, J=8 Hz, NH).

50 (300 MHz, DMSO-$d_6$): 2.94 (d, J=4.7 Hz, 3 H, N—CH$_3$); 3.29 (broad s, 6 H, N$^+$(CH$_3$)$_2$); 3.3 to 3.7 (m, 9H, piperazinyl-H's and 1H of SCH$_2$); 3.93 (s, 3 H, O—CH$_3$); 4.2 (part of the AB quartet, J=18 Hz, 1H of SCH$_2$); 5.28 (d, J=5 Hz, 1 H, β-lactam-H); 5.89 (dd, J=5 Hz and 7.6 Hz, β-lactam-H); 6.9 (s, 1 H, thiazolyl-H); 8.1 (s, 1 H, formyl-H); 8.6 (s, 1 H, CH=N); 9.9 (d, J=8 Hz, NH).

51 (300 MHz, DMSO-$d_6$): 3.7 and 4.2 (AB quartet, J=18 Hz, 2H, SCH$_2$); 3.93 (s, 3 H, O—CH$_3$); 5.35 (d, J=5 Hz, 1 H, β-lactam-H); 5.85 (dd, J=5 Hz and 8 Hz, β-lactam-H); 6.0 (AB quartet, J=9 Hz, 2H); 6.93 (s, 1 H, thiazolyl-H); 8.2 (t, J=7 Hz, 2 H), 8.7 (t, J=7 Hz, 1 H) and 9.1 (d, J=6 Hz, 2H), pyridinium-H; 8.32 (s, 1 H, CH=N); 9.95 (d, J=8 Hz, NH).

52 (90 MHz, DMSO-$d_6$): 3.7 (s, 3 H, N—CH$_3$); 3.65 and 4.1 (AB quartet, J=18 Hz, 2H, SCH$_2$); 3.95 (s, 3 H, O—CH$_3$); 5.35 (d, J=5 Hz, 1 H, β-lactam-H); 5.85 (dd, J=5 Hz and 8 Hz, β-lactam-H); 7.0 (s, 1 H, thiazolyl-H); 8.75 (s, 1 H, CH=N); 9.9 (d, J=8 Hz, NH).

53 (90 MHz, DMSO-$d_6$): 2.25 (s, 3 H, triazinyl-CH$_3$); 3.5 and 4.65 (AB quartet, J=18 Hz, 2H, SCH$_2$); 4.0 (s, 3 H, O—CH$_3$); 5.35 (d, J=5 Hz, 1 H, β-lactam-H); 5.85 (dd, J=5 Hz and 8 Hz, β-lactam-H); 6.95 (s, 1 H, thiazolyl-H); 8.85 (s, 1 H, CH=N); 9.95 (d, J=8 Hz, NH).

54 (90 MHz, DMSO-$d_6$): 2.3 (s, 3 H, CH$_3$); 1.8 to 2.1 (m, 1 H); 3.6 and 4.55 (AB quartet, J=18 Hz, 2H, SCH$_2$); 3.95 (s, 3 H, O—CH$_3$); 5.35 (d, J=5 Hz, 1 H, β-lactam-H); 5.9 (dd, J=5 Hz and 8 Hz, β-lactam-H); 6.95 (s, 1 H, thiazolyl-H); 8.65 (s, 1 H, CH=N); 9.9 (d, J=8 Hz, NH).

55 (90 MHz, DMSO-$d_6$): 2.8 (broad duplet, 3H, N—CH$_3$); 3.2 to 3.7 (m, 5 H, N—CH$_2$—CH$_2$—O and 1H of SCH$_2$); 3.95 (s, 3 H, O—CH$_3$); 4.5 (part of the AB quartet, J=18 Hz, 1H of SCH$_2$); 5.3 (d, J=5 Hz, 1 H, β-lactam-H); 5.85 (dd, J=5 Hz and 8 Hz, β-lactam-H); 6.95 (s, 1 H, thiazolyl-H); 8.65 (s, 1 H, CH=N); 9.9 (d, J=8 Hz, NH).

56 (90 MHz, DMSO-$d_6$): 3.7 and 4.15 (AB quartet, J=18 Hz, 2H, SCH$_2$); 4.0 (s, 3 H, O—CH$_3$); 5.35 (d, J=5 Hz, 1 H, β-lactam-H); 5.85 (dd, J=5 Hz and 8 Hz, β-lactam-H); 7.0 (s, 1 H, thiazolyl-H); 7 to 7.8 (m, 4 H, aromatic-H); 8.45 (s, 1 H, CH=N); 9.95 (d, J=8 Hz, NH).

57 (90 MHz, DMSO-$d_6$): 3.35 broad singulet, 3 H, NCH$_3$); 3.55 and 4.55 (AB quartet, J=18 Hz, 2H, SCH$_2$); 3.95 (s, 3 H, O—CH$_3$); 5.3 (d, J=5 Hz, 1 H, β-lactam-H); 5.85 (dd, J=5 Hz and 8 Hz, β-lactam-H); 6.95 (s, 1 H, thiazolyl-H); 8.15 (s, 1 H, CH=N); 9.85 (d, J=8 Hz, NH).

58 (90 MHz, DMSO-$d_6$): 2.95 (broad duplet, 3 H, NCH$_3$); 3.35 (broad singulet, 3 H, NCH$_3$); 3.65 and 4.65 (AB quartet, J=18 Hz, 2H, SCH$_2$); 3.95 (s, 3 H, O—CH$_3$); 5.3 (d, J=5 Hz, 1 H, β-lactam-H); 5.85 (dd, J=5 Hz and 8 Hz, β-lactam-H); 6.95 (s, 1 H, thiazolyl-H); 8.1 (s, 1 H, CH=N); 9.85 (d, J=8 Hz, NH).

59 (90 MHz, DMSO-$d_6$): 1 to 1.5 (m, 4 H, —CH$_2$—CH$_2$—); 1.8 to 2.1 (m, 1 H); 3.55 and 4.55 (AB quartet, J=18 Hz, 2H, SCH$_2$); 3.95 (s, 3 H, O—CH$_3$); 5.3 (d, J=5 Hz, 1 H, β-lactam-H); 5.85 (dd, J=5 Hz and 8 Hz, β-lactam-H); 6.9 (s, 1 H, thiazolyl-H); 8.65 (s, 1 H, CH=N); 9.9 (d, J=8 Hz, NH).

60 (90 MHz, DMSO-$d_6$): 3.7 and 4.8 (AB quartet, J=18 Hz, 2H, SCH$_2$); 4.0 (s, 3 H, O—CH$_3$); 5.35 (d, J=5 Hz, 1 H, β-lactam-H); 5.95 (dd, J=5 Hz and 8 Hz, β-lactam-H); 7.0 (s, 1 H, thiazolyl-H); 7.85 (dd, J=4 Hz and 6 Hz, pyridinyl-H); 8.2 (dt, J=2 and 8 Hz, pyridinyl-H); 8.5 (d, J=6 Hz, pyridinyl-H); 8.9 (d, J=4 Hz, pyridinyl-H); 8.95 (s, 1 H, CH=N); 9.95 (d, J=8 Hz, NH).

61 (90 MHz, DMSO-$d_6$): 3.6 and 4.15 (AB quartet, J=18 Hz, 2H, SCH$_2$); 3.85 (s, 3 H, O—CH$_3$); 5.25 (d, J=5 Hz, 1 H, β-lactam-H); 5.85 (dd, J=5 Hz and 8 Hz, β-lactam-H); 6.75 (s, 1 H, thiazolyl-H); 7.5 (dd, J=5 Hz and 8 Hz, pyridinyl-H); 8.25 (broad duplet, J=8 Hz, pyridinyl-H); 8.65 (broad triplet, J=6 Hz, pyridinyl-H); 9.05 (s, 1 H, CH═N); 9.7 (d, J=8 Hz, NH).

62 (300 MHz, DMSO-$d_6$): 3.13 (broad duplet, 3 H, N—CH$_3$); 3.29 (broad s, 6 H, N$^+$(CH$_3$)$_2$); 3.4 to 3.75 (m, 5 H, —CH$_2$—N$^+$—CH$_2$— and 1H of SCH$_2$); 3.85 (s, 3 H, O—CH$_3$); 4 to 4.3 (m, 4 H, —CH$_2$—N—CH$_2$—); 4.65 (part of the AB quartet, J=18 Hz, 1H of SCH$_2$); 5.27 (d, J=5 Hz, 1 H, β-lactam-H); 5.85 (dd, J=5 Hz and 7.6 Hz, β-lactam-H); 6.78 (s, 1 H, thiazolyl-H); 8.75 (s, 1 H, CH═N); 9.75 (d, J=7.6 Hz, NH).

63 (90 MHz, DMSO-$d_6$+TFA): 3.0 (broad duplet, 3 H, N—CH$_3$); 3.2 (s, 9 H, N$^+$(CH$_3$)$_3$); 3.5 to 3.8 (m, 5 H, N—CH$_2$—CH$_2$—N$^+$ and 1H of SCH$_2$); 3.90 (s, 3 H, O—CH$_3$); 4.65 (part of the AB quartet, J=18 Hz, 1H of SCH$_2$); 5.3 (d, J=5 Hz, 1 H, β-lactam-H); 5.85 (dd, J=5 Hz and 8 Hz, β-lactam-H); 6.8 (s, 1 H, thiazolyl-H); 8.75 (s, 1 H, CH═N); 9.75 (d, J=8 Hz, NH).

64 (90 MHz, DMSO-$d_6$): 3.65 and 4.15 (AB quartet, J=18 Hz, 2H, SCH$_2$); 4.0 (s, 3 H, O—CH$_3$); 5.25 (d, J=5 Hz, 1 H, β-lactam-H); 5.8 (dd, J=5 Hz and 8 Hz, β-lactam-H); 7.0 (s, 1 H, thiazolyl-H); 7.2 (d, J=5 Hz, 1 H, pyrimidinyl-H); 8.45 (s, 1 H, CH═N); 8.8 (d, J=5 Hz, 1 H, pyrimidinyl-H); 9.9 (d, J=8 Hz, NH).

65 (90 MHz, DMSO-$d_6$+TFA): 4.0 (s, 3 H, O—CH$_3$); 3.6 and 4.65 (AB quartet, J=18 Hz, 2H, SCH$_2$); 5.25 (d, J=5 Hz, 1 H, β-lactam-H); 5.85 (dd, J=5 Hz and 8 Hz, β-lactam-H); 7.0 (s, 1 H, thiazolyl-H); 8.3 (s, 1 H, CH═N); 9.85 (d, J=8 Hz, NH).

66 (90 MHz, DMSO-$d_6$): 3.2 (broad singulet, 3 H, N—CH$_3$); 3.0 to 3.4 (m, 4 H, —CH$_2$—N—CH$_2$); 3.4 to 3.8 (m, 5 H, —CH$_2$—NH$^+$—CH$_2$— and 1H of SCH$_2$); 3.95 (s, 3 H, O—CH$_3$); 4.3 (part of the AB quartet, J=18 Hz, 1H of SCH$_2$); 5.35 (d, J=5 Hz, 1 H, β-lactam-H); 5.85 (dd, J=5 Hz and 8 Hz, β-lactam-H); 7.0 (s, 1 H, thiazolyl-H); 8.15 (s, 1 H, CH═N); 9.9 (d, J=8 Hz, NH).

67 (90 MHz, DMSO-$d_6$): 3.3 (s, 3 H, N—CH$_3$); 3.3 (broad s, 6 H, N$^+$(CH$_3$)$_2$); 3.3 to 3.7 (m, 9H, piperazinyl-H's and 1H of SCH$_2$); 3.85 (s, 3 H, O—CH$_3$); 4.25 (part of the AB quartet, J=18 Hz, 1H of SCH$_2$); 5.25 (d, J=5 Hz, 1 H, β-lactam-H); 5.8 (dd, J=5 Hz and 8 Hz, β-lactam-H); 6.8 (s, 1 H, thiazolyl-H); 8.1 (s, 1 H, formyl-H); 8.15 (s, 1 H, CH═N); 9.75 (d, J=8 Hz, NH).

68 (90 MHz, DMSO-$d_6$): 2.25 (s, 3 H); 3.65 (s, 3 H, N—CH$_3$); 3.7 and 4.6 (AB quartet, J=18 Hz, 2H, SCH$_2$); 3.9 (s, 3 H, O—CH$_3$); 5.3 (d, J=5 Hz, 1 H, β-lactam-H); 5.85 (dd, J=5 Hz and 8 Hz, β-lactam-H); 6.05 (d, J=4 Hz, pyrrol-H); 6.85 (d, J=4 Hz, pyrrol-H); 6.9 (s, 1 H thiazolyl-H); 8.75 (s, 1 H, CH═N); 9.9 (d, J=8 Hz, NH).

69 (90 MHz, DMSO-$d_6$): 3.5 and 4.45 (AB quartet, J=20 Hz, 2H, SCH$_2$); 5.25 (d, J=5 Hz, 1 H, β-lactam-H); 5.75 (d, J=55 Hz, 2H, —CH$_2$F); 5.85 (dd, J=5 Hz and 8 Hz, β-lactam-H); 8.25 (s, 1 H, CH═N);9.85 (d, J=8 Hz, NH).

70 (300 MHz, DMSO-$d_6$): 1.13 (t, J=7.1 Hz, 3H, CH$_3$); 3.31 (qd, J=7.1 and ca. 6 Hz, 2H, CH$_2$); 3.55 and 4.47 (AB quartet, J=18.1 Hz, 2H, S—CH$_2$); 5.29 (d, J=5.0 Hz, 1H, β-lactam-H); 5.89 (dd, J=5.0 and 7.9 Hz, 1H, β-lactam-H); 6.78 (s, 1H, CH thiazol); 8.01 (broad, 2H, NH); 8.19 (broad t 1H, NH); 8.32 (s, 1H, CH═N); 9.70 (d, J=7.9 Hz, 1H, NH); 12.03 (s, 1H, OH).

71 (300 MHz, DMSO-$d_6$): 2.98 (d, J=4.6 Hz, 3H, N—CH$_3$); 3.56 and 4.46 (AB quartet, J=18.1 Hz, 2H, S—CH$_2$); 5.28 (d, J=4.9 Hz, 1H, β-lactam-H); 5.87 (dd, J=4.9 and 7.9 Hz, 1H, β-lactam-H); 6.83 (s, 1H, CH thiazol); 8.22 (s, 1H, CH═N); 8.48 (q broad J=4.6 Hz, 1H, NH); 9.75 (d, J=7.9 Hz, 1H, NH); 11.63 (s, 1H, OH); 12.28 (s, 1H, OH).

72 (300 MHz, DMSO-$d_6$): 3.53 and 4.47 (AB quartet, J=18.1 Hz, 2H, S—CH$_2$); 5.26 (d, J=5.0 Hz, 1H, β-lactam-H); 5.88 (dd, J=4.9 and 7.9 Hz, 1H, β-lactam-H); 6.84 (s, 1H, CH thiazol); 8.00 (s, 1H, NH); 8.23 (s, 1H, CH═N); 8.28 (s, 1H, NH); 9.76 (d, J=7.9 Hz, 1H, NH); 11.56 (s, 1H, OH); 12.31 (s, 1H, OH).

73 (300 MHz, DMSO-$d_6$): 1.16 (t, J=7.1 Hz, 3H, CH$_3$); 1.90 (m broad, 4H, CH$_2$); 3.39 (qd, J=7.1 and ca. 6 Hz, 2H, CH$_2$); 3.56 (m broad, 4H, CH$_2$); 3.63 and 4.07 (AB quartet, J=18.0 Hz, 2H, S—CH$_2$); 5.28 (d, J=5.0 Hz, 1H, β-lactam-H); 5.88 (dd, J=5.0 and 7.8 Hz, 1H, β-lactam-H); 6.81 (s, 1H, CH thiazol); 7.97 (t broad, J=ca. 6 Hz 1H, NH); 8.60 (s, 1H, CH═N); 9.76 (d, J=7.8 Hz, 1H, NH); 11.70 (s, 1H, OH); 12.26 (s, 1H, OH).

74 (300 MHz, DMSO-$d_6$): 3.57 and 4.48 (AB quartet, J=18.1 Hz, 2H, S—CH$_2$); 3.97 (broad, 2H, N—CH$_2$—C═C); 5.1–5.3 (m, 2H, C═CH$_2$); 5.30 (d, J=5.1 Hz, 1H, β-lactam-H); 5.8–5.9 (m, 1H, C—CH═C); 5.89 (dd, J=4.9 and 8.2 Hz, 1H, β-lactam-H); 6.83 (s, 1H, CH thiazol); 8.10 (s, 2H, NH); 8.34 (s, 1H, CH═N); 8.41 (s, 1H, NH); 9.77 (d, J=8.0 Hz, 1H, NH); 12.26 (s, 1H, OH); 12.38 (s, 1H, OH).

75 (300 MHz, DMSO-$d_6$): 1.89 (m broad 2H, CH$_2$); 3.33 (s broad, 4H, N—CH$_2$); 3.54 and 4.42 (AB quartet, J=18.1 Hz, 2H, S—CH$_2$); 5.29 (d, J=5.0 Hz, 1H, β-lactam-H); 5.89 (dd, J=5.0 and 8.0 Hz, 1H, β-lactam-H); 6.76 (s, 1H, CH thiazol); 8.29 (s, 1H, CH═N); 8.38 (s, 2H, NH); 9.66 (d, J=8.0 Hz, 1H, NH); 11.90 (s, 1H, OH); 12.03 (s, 1H, OH).

76 (300 MHz, DMSO-$d_6$): 0.89 (t, 3H, C—CH$_3$); 1.2–1.4 (m, 2H, C—CH$_2$—C); 1.4–1.6 (m, 2H, C—CH$_2$—C); 3.2–3.4 (m, 2H, N—CH$_2$—C); 3.56 and 4.47 (AB quartet, J=18.1 Hz, 2H, S—CH$_2$); 5.30 (d, J=5.0 Hz, 1H, β-lactam-H); 5.89 (dd, J=5.0 and 7.9 Hz, 1H, β-lactam-H); 6.83 (s, 1H, CH thiazol); 8.04 (s, 2H, NH); 8.24 (s, 1H, CH═N); 8.32 (s, 1H, NH); 9.76 (d, J=7.9 Hz, 1H, NH); 12.13 (s, 1H, OH); 12.36 (s, 1H, OH).

77 (300 MHz, DMSO-$d_6$): 3.66 and 3.92 (AB quartet, J=17.9 Hz, 2H, S—CH$_2$); 3.86 (s, 3H, O—CH$_3$); 5.27 (d, J=5.0 Hz, 1H, β-lactam-H); 5.88 (dd, J=5.0 and 7.8 Hz, 1H, β-lactam-H); 6.84 (s, 1H, CH thiazol); 8.22 (s, 1H, CH═N); 9.78 (d, J=7.8 Hz, 1H, NH); 12.34 (s, 1H, OH).

78 (300 MHz, DMSO-$d_6$): 1.39 (s, 9H, C—CH$_3$); 3.56 and 4.47 (AB quartet, J=18.0 Hz, 2H, S—CH$_2$); 5.29 (d, J=5.0 Hz, 1H, β-lactam-H); 5.89 (dd, J=5.0 and 7.9 Hz, 1H, β-lactam-H); 6.81 (s, 1H, CH thiazol); 7.90 (s broad 2H, NH); 7.99 (s broad 1H, NH); 8.25 (s, 1H, CH═N); 9.68 (d, J=7.9 Hz, 1H, NH); 12.03 (s, 1H, OH); 12.16 (s, 1H, OH).

79 (300 MHz, DMSO-$d_6$): 2.92 (d, J=4.8 Hz, 3H, N—CH$_3$); 3.03 (s, 6H, N—CH$_3$); 3.61 and 4.17 (AB quartet, J=18.0 Hz, 2H, S—CH$_2$); 5.29 (d, J=5.0 Hz, 1H, β-lactam-H); 5.88 (dd, J=5.0 and 7.8 Hz, 1H, β-lactam-H); 6.81 (s, 1H, CH thiazol); 8.20 (q broad J=4.8 Hz, 1H, NH); 8.55 (s, 1H, CH═N); 9.76 (d, J=7.5 Hz, 1H, NH); 11.83 (s, 1H, OH); 12.28 (s, 1H, OH).

80 (300 MHz, DMSO-$d_6$): 2.75 (s, 2H, N—CH$_2$); 3.55 and 4.54 (AB quartet, J=18.1 Hz, 2H, S—CH$_2$); 5.32 (d, J=5.1 Hz, 1H, β-lactam-H); 5.93 (dd, J=5.1 and 7.9 Hz, 1H, β-lactam-H); 6.79 (s, 1H, CH thiazol); 8.59 (s, 1H, CH═N); 9.73 (d, J=8.0 Hz, 1H, NH); 12.13 (s, 1H, OH).

81 (300 MHz, DMSO-$d_6$): 3.55 and 4.54 (AB quartet, J=18.1 Hz, 2H, S—CH$_2$); 3.5–3.6 (m, 4H, CH$_2$); 3.6–3.7 (m, 4H, CH$_2$); 5.30 (d, J=5.1 Hz, 1H, β-lactam-H); 5.89 (dd, J=5.0 and 7.9 Hz, 1H, β-lactam-H); 6.84 (s, 1H, CH thiazol); 8.35 (broad, 2H, NH); 8.65 (s, 1H, CH=N); 9.80 (d, J=7.9 Hz, 1H, NH); 12.27 (s, 1H, OH); 12.51 (s, 1H, OH).

82 (300 MHz, DMSO-d$_6$): 0.64 (m, 2H, cyclopr. CH$_2$); 0.83 (m, 2H, cyclopr. CH$_2$); 2.62 (m, 1H, cyclopr. CH); 3.53 and 4.49 (AB quartet, J=18.1 Hz, 2H, S—CH$_2$); 5.29 (d, J=5.0 Hz, 1H, β-lactam-H); 5.89 (dd, J=5.0 and 8.0 Hz, 1H, β-lactam-H); 6.79 (s, 1H, CH thiazol); 8.09 (s, 2H, NH); 8.35 (s, 1H, CH=N); 8.59 (s, 1H, NH); 9.70 (d, J=8.0 Hz, 1H, NH); 12.08 (s, 1H, OH); 12.13 (s, 1H, OH).

83 (300 MHz, DMSO-d$_6$): 3.54 and 4.48 (AB quartet, J=18.1 Hz, 2H, S—CH$_2$); 5.29 (d, J=5.0 Hz, 1H, β-lactam-H); 5.89 (dd, J=4.9 and 7.8 Hz, 1H, β-lactam-H); 6.83 (s, 1H, CH thiazol); 8.15 (s, 2H, NH); 8.39 (s, 1H, CH=N); 9.79 (d, J=7.9 Hz, 1H, NH); 11.21 (s, 1H, OH); 12.15 (s, 1H, OH); 12.44 (s, 1H, OH).

84 (300 MHz, DMSO-d$_6$): 3.09 (s, 6H, N—CH$_3$); 3.55 and 4.55 (AB quartet, J=18.1 Hz, 2H, S—CH$_2$); 5.30 (d, J=5.0 Hz, 1H, β-lactam-H); 5.89 (dd, J=5.0 and 7.8 Hz, 1H, β-lactam-H); 6.84 (s, 1H, CH thiazol); 8.07 (s, 2H, NH); 8.65 (s, 1H, CH=N); 9.81 (d, J=7.9 Hz, 1H, NH); 11.86 (s, 1H, OH); 12.53 (s, 1H, OH).

85 (300 MHz, DMSO-d$_6$): 3.58 and 4.50 (AB quartet, J=18.0 Hz, 2H, S—CH$_2$); 4.90 (d, J=6.4 Hz, 2H, N—CH$_2$); 5.31 (d, J=5.1 Hz, 1H, β-lactam-H); 5.90 (dd, J=5.2 and 7.8 Hz, 1H, β-lactam-H); 6.84 (s, 1H, CH thiazol); 7.6–7.8 (m, 2H, CH aromatic); 8.1–8.3 (m, 1H, CH aromatic); 8.35 (s broad, 1H, NH); 8.39 (s, 1H, CH=N); 8.7–8.8 (m, 2H, CH aromatic); 9.3 (broad, 1H, NH); 9.78 (d, J=7.8 Hz, 1H, NH); 12.42 (s, 1H, OH); 12.49 (s, 1H, OH).

86 (300 MHz, DMSO-d$_6$): 3.57 and 4.52 (AB quartet, J=18.0 Hz, 2H, S—CH$_2$); 4.85 (d, J=6.6 Hz, 2H, N—CH$_2$); 5.30 (d, J=5.0 Hz, 1H, β-lactam-H); 5.90 (dd, J=5.0 and 7.8 Hz, 1H, β-lactam-H); 6.82 (s, 1H, CH thiazol); 7.9–8.1 (m, 1H, CH aromatic); 8.38 (s, 1H, CH=N); 8.4–8.6 (m, 1H, CH aromatic); 8.8–8.9 (m, 1H, CH aromatic); 8.9–9.0 (m, 1H, CH aromatic); 8.7–8.8 (m, 2H, CH aromatic); 9.77 (d, J=7.9 Hz, 1H, NH); 12.32 (s, 1H, OH); 12.45 (s, 1H, OH).

87 (300 MHz, DMSO-d$_6$): 3.57 and 4.52 (AB quartet, J=18.1 Hz, 2H, S—CH$_2$); 4.98 (d, J=6.2 Hz, 2H, N—CH$_2$); 5.30 (d, J=5.0 Hz, 1H, β-lactam-H); 5.90 (dd, J=5.0 and 7.9 Hz, 1H, β-lactam-H); 6.81 (s, 1H, CH thiazol); 7.9–8.0 (m, 2H, CH aromatic); 8.40 (s, 1H, CH=N); 8.8–9.0 (m, 1H, CH aromatic); 9.00 (s broad 1H, NH); 9.76 (d, J=7.9 Hz, 1H, NH); 12.30 (s, 1H, OH); 12.56 (s, 1H, OH).

88 (300 MHz, DMSO-d$_6$): 3.68 and 4.05 (AB quartet, J=17.9 Hz, 2H, S—CH$_2$); 4.19 and 4.38 (AB quartet, J=16.4 Hz, 2H, N—CH$_2$—C=O); 5.30 (d, J=5.0 Hz, 1H, β-lactam-H); 5.87 (dd, J=5.0 and 7.7 Hz, 1H, β-lactam-H); 6.87 (s, 1H, CH thiazol); 7.86 (s, 1H, CH=N); 9.82 (d, J=7.7 Hz, 1H, NH); 11.35 (s, 1H, OH); 12.45 (s, 1H, OH).

89 (300 MHz, DMSO-d$_6$): 3.58 and 4.64 (AB quartet, J=18.1 Hz, 2H, S—CH$_2$); 5.29 (d, J=4.9 Hz, 1H, β-lactam-H); 5.89 (dd, J=4.9 and 7.9 Hz, 1H, β-lactam-H); 6.84 (s, 1H, CH thiazol); 7.1–7.6 (m, CH aromatic); 8.33 (s, 1H, CH=N); 9.78 (d, J=7.9 Hz, 1H, NH); 10.03 (s, 1H, NH); 11.86 (s, 1H, OH); 12.35 (s, 1H, OH).

90 (300 MHz, DMSO-d$_6$): 3.66 and 4.70 (AB quartet, J=18.1 Hz, 2H, S—CH$_2$); 5.34 (d, J=5.0 Hz, 1H, β-lactam-H); 5.92 (dd, J=5.0 and 7.9 Hz, 1H, β-lactam-H); 6.84 (s, 1H, CH thiazol); 7.0–7.2 (m, 1H, CH aromatic); 7.2–7.3 (m, 1H, CH aromatic); 8.0–8.2 (m, 2H, CH aromatic); 8.49 (s, 1H, CH=N); 9.79 (d, J=8.0 Hz, 1H, NH); 12.32 (s, 1H, OH); 13.41 (s, 1H, OH).

91 (300 MHz, DMSO-d$_6$): 3.65 and 4.03 (AB quartet, J=17.8 Hz, 2H, S—CH$_2$); 5.27 (d, J=4.9 Hz, 1H, β-lactam-H); 5.83 (dd, J=4.9 and 7.7 Hz, 1H, β-lactam-H); 6.88 (s, 1H, CH thiazol); 8.52 (s, 1H, CH=N); 9.77 (d, J=7.7 Hz, 1H, NH); 11.08 (s, 1H, OH); 12.35 (s, 1H, OH).

92 (300 MHz, DMSO-d$_6$): 1.51 (s, 3H, C—CH$_3$); 1.54 (s, 3H, C—CH$_3$); 2.86 (d, J=4.9 Hz, 3H, N—CH$_3$); 3.55 and 4.50 (AB quartet, J=18.2 Hz, 2H, S—CH$_2$); 5.32 (d, J=5.1 Hz, 1H, β-lactam-H); 5.96 (dd, J=5.0 and 8.2 Hz, 1H, β-lactam-H); 6.95 (s, 1H, CH thiazol); 8.03 (s broad 2H, NH); 8.18 (s broad 1H, NH); 8.32 (s, 1H, CH=N); 9.74 (d, J=7.9 Hz, 1H, NH); 12.19 (s, 1H, OH).

93 (300 MHz, DMSO-d$_6$): 2.9 (broad, 3H, N—CH$_3$); 3.54 and 4.50 (AB quartet, J=18.1 Hz, 2H, S—CH$_2$); 5.30 (d, J=5.1 Hz, 1H, β-lactam-H); 5.89 (dd, J=5.0 and 7.8 Hz, 1H, β-lactam-H); 6.83 (s, 1H, CH thiazol); 8.62 (s, 1H, CH=N); 9.79 (d, J=7.9 Hz, 1H, NH); 11.98 (s, 1H, OH); 12.42 (s, 1H, OH).

94 (300 MHz, DMSO-d$_6$): 3.39 (m broad 2H, CH$_2$); 3.54 (m broad 2H, CH$_2$); 2.89 (d, J=4.6 Hz, 3H, N—CH$_3$); 3.55 and 4.49 (AB quartet, J=18.0 Hz, 2H, S—CH$_2$); 5.30 (d, J=5.0 Hz, 1H, β-lactam-H); 5.90 (dd, J=5.0 and 7.9 Hz, 1H, β-lactam-H); 6.79 (s, 1H, CH thiazol); 8.61 (s, 1H, CH=N); 9.71 (d, J=7.9 Hz, 1H, NH); 11.73 (s, 1H, OH); 12.10 (s, 1H, OH).

95 (300 MHz, DMSO-d$_6$): 2.26 (s, 3H, CH$_3$); 3.57 and 4.70 (AB quartet, J=18.0 Hz, 2H, S—CH$_2$); 5.33 (d, J=5.0 Hz, 1H, β-lactam-H); 5.93 (dd, J=5.0 and 7.9 Hz, 1H, β-lactam-H); 6.83 (s, 1H, CH thiazol); 8.77 (s, 1H, CH=N); 9.80 (d, J=7.9 Hz, 1H, NH); 12.40 (s, 1H, OH).

96 (300 MHz, DMSO-d$_6$): 3.22 (m broad 4H, N—CH$_2$); 3.55 and 4.52 (AB quartet, J=18.1 Hz, 2H, S—CH$_2$); 3.85 (m broad 4H, N—CH$_2$); 5.30 (d, J=5.0 Hz, 1H, β-lactam-H); 5.90 (dd, J=5.0 and 7.9 Hz, 1H, β-lactam-H); 6.82 (s, 1H, CH thiazol); 8.5 (broad, 2H, NH); 8.65 (s, 1H, CH=N); 9.76 (d, J=7.9 Hz, 1H, NH); 9.82 (s, 2H, NH); 12.31 (s, 1H, OH); 12.47 (s, 1H, OH).

97 (300 MHz, DMSO-d$_6$): 3.14 (s, 6H, N—CH$_3$); 3.64 and 3.94 (AB quartet, J=17.9 Hz, 2H, S—CH$_2$); 3.68 (s 4H, N—CH$_2$); 5.28 (d, J=5.0 Hz, 1H, β-lactam-H); 5.89 (dd, J=5.0 and 7.7 Hz, 1H, β-lactam-H); 6.81 (s, 1H, CH thiazol); 8.64 (s, 1H, CH=N); 9.77 (d, J=7.7 Hz, 1H, NH); 12.29 (s, 1H, OH); 12.36 (s, 1H, OH).

98 (300 MHz, DMSO-d$_6$): 3.33 (s, 3H, N—CH$_3$); 3.54 and 4.55 (AB quartet, J=18.3 Hz, 2H, S—CH$_2$); 5.29 (d, J=5.0 Hz, 1H, β-lactam-H); 5.91 (dd, J=5.1 and 7.9 Hz, 1H, β-lactam-H); 6.76 (s, 1H, CH thiazol); 8.10 (s, 1H, CH=N); 8.2 (s, NH); 9.67 (d, J=7.8 Hz, 1H, NH); 11.92 (s, 1H, OH).

99 (300 MHz, DMSO-d$_6$): 2.80 (s, 3H, CH$_3$); 3.57 and 4.48 (AB quartet, J=18.1 Hz, 2H, S—CH$_2$); 5.34 (d, J=5.1 Hz, 1H, β-lactam-H); 5.94 (dd, J=5.1 and 7.9 Hz, 1H, β-lactam-H); 6.82 (s, 1H, CH thiazol); 8.55 (s, 1H, CH=N); 9.28 (s, 1H, NH); 9.80 (d, J=7.9 Hz, 1H, NH); 9.90 (s, 1H, NH); 12.39 (s, 1H, OH); 13.52 (s, 1H, OH).

100 (300 MHz, DMSO-d$_6$): 3.58 and 4.46 (AB quartet, J=18.1 Hz, 2H, S—CH$_2$); 5.34 (d, J=5.1 Hz, 1H, β-lactam-H); 5.94 (dd, J=5.1 and 7.9 Hz, 1H, β-lactam-H); 6.82 (s, 1H, CH thiazol); 8.28 (dd, J=6.7 and 14.8 Hz, 1H, N—CH=N); 8.58 (s, 1H, CH=N); 9.58 (d, J=14.8 Hz 1H, NH); 9.77 (d, J=8.0 Hz, 1H, NH); 9.9 (d, J=6.7 Hz 1H, NH); 12.29 (s, 1H, OH).

101 (300 MHz, DMSO-d$_6$): 3.57 and 4.48 (AB quartet, J=18.0 Hz, 2H, S—CH$_2$); 3.9 (s, 3H, O—CH$_3$); 5.33 (d, J=5.1 Hz, 1H, β-lactam-H); 5.92 (dd, J=5.1 and 8.0 Hz, 1H, β-lactam-H); 6.87 (s, 1H, CH thiazol); 8.27 (dd, J=6.9 and 14.6 Hz, 1H, N—CH=N); 8.60 (s, 1H, CH=N); 9.55 (d, J=14.4 Hz 1H, NH); 9.79 (d, J=8.0 Hz, 1H, NH); 9.91 (d, J=6.5 Hz 1H, NH).

102 (300 MHz, DMSO-$d_6$): 1.49 (s, 3H, C—CH$_3$); 1.50 (s, 3H, C—CH$_3$); 3.54 and 4.48 (AB quartet, J=18.1 Hz, 2H, S—CH$_2$); 5.31 (d, J=4.9 Hz, 1H, β-lactam-H); 5.97 (dd, J=4.9 and 8 Hz, 1H, β-lactam-H); 6.84 (s, 1H, CH thiazol); 8.29 (s, 1H, CH=N); 9.65 (d, J=8 Hz, 1H, NH); 12.06 (s, 1H, OH).

103 (300 MHz, DMSO-$d_6$): 1.51 (s, 3H, C—CH$_3$); 1.53 (s, 3H, C—CH$_3$); 3.52 and 4.52 (AB quartet, J=18.3 Hz, 2H, S—CH$_2$); 5.30 (d, J=5.0 Hz, 1H, β-lactam-H); 5.95 (dd, J=5.0 and 8.1 Hz, 1H, β-lactam-H); 6.94 (s, 1H, CH thiazol); 7.61 (s broad 2H, NH); 8.15 (s broad 2H, NH); 8.38 (s, 1H, CH=N); 9.74 (d, J=8.1 Hz, 1H, NH); 11.20 (s, 1H, OH); 12.16 (s, 1H, OH).

104 (300 MHz, DMSO-$d_6$): 1.49 (s, 3H, C—CH$_3$); 1.51 (s, 3H, C—CH$_3$); 3.56 and 4.52 (AB quartet, J=18.3 Hz, 2H, S—CH$_2$); 4.90 (d, J=6.3 Hz, 2H, CH$_2$); 5.32 (d, J=5.0 Hz, 1H, β-lactam-H); 5.97 (dd, J=5.0 and 8.1 Hz, 1H, β-lactam-H); 6.91 (s, 1H, CH thiazol); 7.6–7.8 (m 2H, CH aromatic); 8.2–8.3 (m 1H, CH aromatic); 8.38 (s, 1H, CH=N); 8.6–8.8 (m 1H, CH aromatic); 9.71 (d, J=8.2 Hz, 1H, NH); 12.48 (s, 1H, OH).

105 (300 MHz, DMSO-$d_6$): 0.64 (m broad 2H, CH$_2$); 0.84 (m broad 2H, CH$_2$); 1.50 (s, 3H, C—CH$_3$); 1.52 (s, 3H, C—CH$_3$); 2.61 (m broad 1H, N—CH); 3.53 and 4.53 (AB quartet, J=18.2 Hz, 2H, S—CH$_2$); 5.31 (d, J=5.0 Hz, 1H, β-lactam-H); 5.96 (dd, J=5.0 and 8.2 Hz, 1H, β-lactam-H); 6.90 (s, 1H, CH thiazol); 8.10 (s broad 2H, NH); 8.34 (s, 1H, CH=N); 8.60 (s broad 1H, NH); 9.70 (d, J=8.2 Hz, 1H, NH); 12.08 (s, 1H, OH).

106 (300 MHz, DMSO-$d_6$): 1.50 (s, 3H, C—CH$_3$); 1.52 (s, 3H, C—CH$_3$); 2.87 (broad 6H, N—CH$_3$); 3.54 and 4.51 (AB quartet, J=18.1 Hz, 2H, S—CH$_2$); 5.33 (d, J=5.0 Hz, 1H, β-lactam-H); 5.96 (dd, J=5.0 and 8.1 Hz, 1H, β-lactam-H); 6.91 (s, 1H, CH thiazol); 8.06 (s broad 1H, NH); 8.30 (s broad 1H, NH); 8.62 (s, 1H, CH=N); 9.71 (d, J=8.4 Hz, 1H, NH); 11.76 (s, 1H, OH).

107 (300 MHz, DMSO-$d_6$): 1.51 (s, 3H, C—CH$_3$); 1.53 (s, 3H, C—CH$_3$); 1.8–2.0 (m, 4H, C—CH$_2$); 1.8–2.0 (m, 4H, N—CH$_2$); 3.54 and 4.55 (AB quartet, J=18.1 Hz, 2H, S—CH$_2$); 5.31 (d, J=5.0 Hz, 1H, β-lactam-H); 5.95 (dd, J=5.0 and 8.3 Hz, 1H, β-lactam-H); 6.90 (s, 1H, CH thiazol); 7.70 (s broad NH); 7.93 (s broad NH); 8.63 (s, 1H, CH=N); 9.62 (d, J=8.2 Hz, 1H, NH); 9.75 (s, 1H, NH); 11.71 (s, 1H, OH).

108 (300 MHz, CD$_3$OD): 8.59 (s, 1H, CH=N); 6.94 (s, 1H, CH); 5.95 (d, J=5.0 Hz, 1H, CH); 5.29 (d, J=5.0 Hz, 1 H, CH); 4.02 (s, 3H, OCH$_3$); 4.34 and 3.61 (AB quartet, J=18.0 Hz, 2H, SCH$_2$); 2.73 (s, 3H, SCH$_3$).

109 (300 MHz, DMSO-$d_6$): 0.64 (m broad 2H, CH$_2$ cyclopr); 0.84 (m broad 2H, CH$_2$ cyclopr); 2.62 (m broad 1H, N—CH cyclopr); 3.54 and 4.51 (AB quartet, J=18.1 Hz, 2H, S—CH$_2$); 4.66 (s, 2H, O—CH$_2$); 5.30 (d, J=5.0 Hz, 1H, β-lactam-H); 5.93 (dd, J=5.0 and 8.1 Hz, 1H, β-lactam-H); 6.93 (s, 1H, CH thiazol); 8.09 (broad 2H, NH); 8.35 (s, 1H, CH=N); 8.58 (broad, 1H, NH); 9.77 (d, J=8.0 Hz, 1H, NH); 12.04 (s, 1H, OH).

110 (300 MHz, DMSO-$d_6$): 2.87 (s, 6H, N—CH$_3$); 3.56 and 4.50 (AB quartet, J=18.0 Hz, 2H, S—CH$_2$); 4.67 (s, 2H, O—CH$_2$); 5.32 (d, J=5.0 Hz, 1H, β-lactam-H); 5.92 (dd, J=5.0 and 8.1 Hz, 1H, β-lactam-H); 6.94 (s, 1H, CH thiazol); 8.1 (broad 1H, NH); 8.35 (broad 1H, NH); 8.63 (s, 1H, CH=N); 9.80 (d, J=8.1 Hz, 1H, NH); 11.77 (s, 1H, OH).

111 (300 MHz, DMSO-$d_6$): 1.93 (broad, 4H, C—CH$_2$); 3.47 (broad, 4H, N—CH$_2$); 3.55 and 4.54 (AB quartet, J=17.9 Hz, 2H, S—CH$_2$); 4.67 (s, 2H, O—CH$_2$); 5.30 (d, J=5.0 Hz, 1H, β-lactam-H); 5.92 (dd, J=5.0 and 7.9 Hz, 1H, β-lactam-H); 6.94 (s, 1H, CH thiazol); 7.96 (broad 2H, NH); 8.62 (s, 1H, CH=N); 9.79 (d, J=7.8 Hz, 1H, NH); 11.72 (s, 1H, OH).

112 (300 MHz, DMSO-$d_6$): 3.62 and 4.67 (AB quartet, J=18.1 Hz, 2H, S—CH$_2$); 5.37 (d, J=5.1 Hz, 1H, β-lactam-H); 5.96 (dd, J=5.1 and 7.9 Hz, 1H, β-lactam-H); 6.83 (s, 1H, CH thiazol); 7.7–7.9 (m, 1H, CH aromatic); 8.1–8.3 (m, 1H, CH aromatic); 8.4–8.6 (m, 1H, CH aromatic); 8.8–8.9 (m, 1H, CH aromatic); 8.97 (s, 1H, CH=N); 9.79 (d, J=7.9 Hz, 1H, NH); 9.85 (s, 1H, NH); 10.37 (s, 1H, NH); 12.31 (s, 1H, OH).

113 (300 MHz, DMSO-$d_6$): 1.1–1.3 (m, 2H, CH$_2$ cyclopr); 1.2–1.4 (m, 2H, CH$_2$ cyclopr); 1.9–2.0 (m, 1H, CH$_2$ cyclopr); 3.54 and 4.49 (AB quartet, J=18.1 Hz, 2H, S—CH$_2$); 5.32 (d, J=5.1 Hz, 1H, β-lactam-H); 5.93 (dd, J=5.1 and 8.0 Hz, 1H, β-lactam-H); 6.76 (s, 1H, CH thiazol); 8.59 (s, 1H, CH=N); 9.07 (s, 1H, NH); 9.23 (s, 1H, NH); 9.67 (d, J=8.0 Hz, 1H, NH); 11.92 (s, 1H, OH); 13.27 (s, 1H, OH).

114 (300 MHz, DMSO-$d_6$): 1.59 (broad, 6H, C—CH$_2$); 3.53 (broad 4H, N—CH$_2$); 3.6 and 4.52 (AB quartet, J=18.4 Hz, 2H, S—CH$_2$); 5.29 (d, J=5.0 Hz, 1H, β-lactam-H); 5.89 (dd, J=5.0 and 7.6 Hz, 1H, β-lactam-H); 6.82 (s, 1H, CH thiazol); 8.16 (s 2H, NH); 8.60 (s, 1H, CH=N); 9.75 (d, J=7.6 Hz, 1H, NH); 11.94 (s, 1H, OH); 12.30 (s, 1H, OH).

115 (300 MHz, DMSO-$d_6$): 3.5 and 4.53 (AB quartet, J=17.9 Hz, 2H, S—CH$_2$); 3.4–3.7 (m, 8H, N—CH$_2$); 5.31 (d, J=5.0 Hz, 1H, β-lactam-H); 5.90 (dd, J=5.0 and 7.9 Hz, 1H, β-lactam-H); 6.82 (s, 1H, CH thiazol); 8.08 (s, 1H, CH=O); 8.38 (broad 2H, NH); 8.62 (s, 1H, CH=N); 9.75 (d, J=7.9 Hz, 1H, NH); 12.18 (s, 1H, OH); 12.28 (s, 1H, OH).

116 (300 MHz, DMSO-$d_6$/D$_2$O): 2.81 (s, 6H, N—CH$_3$); 2.92 (s, 3H, C=N—CH$_3$); 3.54 and 4.58 (AB quartet, J=18.1 Hz, 2H, S—CH$_2$); 3.6 (broad, 2H, N—CH$_2$); 3.97 (broad, 2H, N—CH$_2$); 5.30 (d, J=4.8 Hz, 1H, β-lactam-H); 5.90 (d, J=4.8 Hz, 1H, β-lactam-H); 6.81 (s, 1H, CH thiazol); 8.55 (s, 1H, CH=N).

117 (300 MHz, DMSO-$d_6$/D$_2$O): 2.91 (s, 3H, C=N—CH$_3$); 3.19 (s, 9H, N—CH$_3$); 3.29 (broad, 2H, N—CH$_2$); 3.56 and 4.48 (AB quartet, J=18.1 Hz, 2H, S—CH$_2$); 3.82 (broad, 2H, N—CH$_2$); 5.31 (d, J=5.0 Hz, 1H, β-lactam-H); 5.90 (d, J=5.0 Hz, 1H, β-lactam-H); 6.84 (s, 1H, CH thiazol); 8.56 (s, 1H, CH=N).

118 (300 MHz, DMSO-$d_6$): 3.61 and 4.59 (AB quartet, J=18.0 Hz, 2H, S—CH$_2$); 5.35 (d, J=5.1 Hz, 1H, β-lactam-H); 5.59 (dd, J=5.1 and 7.9 Hz, 1H, β-lactam-H); 6.82 (s, 1H, CH thiazol); 6.9–7.1 (m, 1H, CH aromatic); 7.2–7.4 (m, 2H, CH aromatic); 8.74 (s, 1H, CH=N); 9.31 (s 1H, NH/OH); 9.76 (s 1H, NH/OH); 9.78 (d, J=7.9 Hz, 1H, NH); 12.25 (s, 1H, OH); 13.03 (s, 1H, OH).

119 (300 MHz, DMSO-$d_6$): 2.30 (s, 3H, C—CH$_3$); 3.59 and 4.57 (AB quartet, J=18.1 Hz, 2H, S—CH$_2$); 3.67 (s, 3H, N—CH$_3$); 5.34 (d, J=5.1 Hz, 1H, β-lactam-H); 5.94 (dd, J=5.1 and 8.0 Hz, 1H, β-lactam-H); 6.13 (d, J=3.9 Hz 1H, CH Pyrrol); 6.77 (s, 1H, CH thiazol); 6.86 (d, J=3.9 Hz 1H, CH Pyrrol); 8.66 (s, 1H, CH=N); 9.25 (s 1H, NH); 9.46 (s 1H, NH); 9.70 (d, J=8.0 Hz, 1H, NH); 11.96 (s, 1H, OH); 12.90 (s, 1H, OH).

120 (300 MHz, DMSO-$d_6$): 3.71 and 4.12 (AB quartet, J=17.9 Hz, 2H, S—CH$_2$); 5.32 (d, J=5.1 Hz, 1H, β-lactam-H); 5.91 (dd, J=5.0 and 7.9 Hz, 1H, β-lactam-H); 6.84 (s, 1H, CH thiazol); 7.9–8.0 (m, 2H, CH aromatic); 8.66 (s, 1H, CH=N); 8.8–8.9 (m, 2H, CH aromatic); 8.8 (broad 1H, NH); 9.76 (d, J=8.0 Hz, 1H, NH); 12.17 (s, 1H, OH); 12.37 (s, 1H, OH).

121 (300 MHz, DMSO-$d_6$): 3.22 (s, 6H, N—CH$_3$); 3.54 and 4.55 (AB quartet, J=18.5 Hz, 2H, S—CH$_2$); 3.6 (broad, 4H, N—CH$_2$); 4.0 (broad, 4H, N—CH$_2$); 5.30 (d, J=5.0 Hz, 1H, β-lactam-H); 5.91 (dd, J=5.0 and 7.9 Hz, 1H, β-lactam-H); 6.82 (s, 1H, CH thiazol); 8.73 (s, 1H, CH=N); 9.75 (d, J=7.6 Hz, 1H, NH); 12.30 (s, 1H, OH); 12.76 (s, 1H, OH).

122 (300 MHz, DMSO-$d_6$): 2.76 (s, 3H, N—CH$_3$); 3.1–3.3 (broad, 2H, N—CH$_2$); 3.4–3.6 (broad, 2H, N—CH$_2$); 3.5–3.7 (broad, 2H, N—CH$_2$); 3.55 and 4.53 (AB quartet, J=18.1 Hz, 2H, S—CH$_2$); 4.2–4.4 (broad, 2H, N—CH$_2$); 5.31 (d, J=5.0 Hz, 1H, β-lactam-H); 5.90 (dd, J=5.0 and 7.8 Hz, 1H, β-lactam-H); 6.82 (s, 1H, CH thiazol); 8.66 (s, 1H, CH=N); 9.77 (d, J=7.8 Hz, 1H, NH); 11.74 (s, 1H, NH); 12.36 (s, 1H, OH); 12.56 (s, 1H, OH).

123 (300 MHz, DMSO-$d_6$): 2.90 (d, J=4.7 Hz 3H, N—CH$_3$); 3.34 (s, 3H, N—CH$_3$); 3.55 and 4.59 (AB quartet, J=18.1 Hz, 2H, S—CH$_2$); 5.30 (d, J=5.0 Hz, 1H, β-lactam-H); 5.91 (dd, J=5.0 and 7.9 Hz, 1H, β-lactam-H); 6.81 (s, 1H, CH thiazol); 8.09 (s, 1H, CH=N); 8.25 (s, 2H, NH); 8.37 (s, 1H, NH); 9.72 (d, J=7.9 Hz, 1H, NH); 12.14 (s, 1H, OH).

124 (300 MHz, DMSO-$d_6$): 2.81 (d, J=4.3 Hz 6H, N—CH$_3$); 3.2–3.4 (m broad 2H, N—CH$_2$); 3.56 and 4.55 (AB quartet, J=18.0 Hz, 2H, S—CH$_2$); 3.7–3.9 (m broad 2H, N—CH$_2$); 5.30 (d, J=4.9 Hz, 1H, β-lactam-H); 5.9 (dd, J=4.9 and 7.9 Hz, 1H, β-lactam-H); 6.82 (s, 1H, CH thiazol); 8.3 (broad, NH); 8.38 (s, 1H, CH=N); 8.47 (broad, NH); 9.76 (d, J=7.9 Hz, 1H, NH); 10.84 (s, 1H, NH); 12.31 (s, 2H, OH).

125 (300 MHz, DMSO-$d_6$): 2.82 (d, J=4.5 Hz 6H, N—CH$_3$); 3.2–3.3 (m broad 2H, N—CH$_2$); 3.40 (s, 3H, N—CH$_3$); 3.56 and 4.73 (AB quartet, J=18.3 Hz, 2H, S—CH$_2$); 3.8–3.9 (m broad 2H, N—CH$_2$); 5.29 (d, J=5.0 Hz, 1H, β-lactam-H); 5.91 (dd, J=5.0 and 7.8 Hz, 1H, β-lactam-H); 6.82 (s, 1H, CH thiazol); 8.11 (s, 1H, CH=N); 8.68 (s, 2H, NH); 8.74 (m broad 1H, NH); 9.77 (d, J=7.9 Hz, 1H, NH); 10.91 (s, 1H, OH); 12.32 (s, 1H, OH).

126 (300 MHz, DMSO-$d_6$): 3.60 and 4.56 (AB quartet, J=18.1 Hz, 2H, S—CH$_2$); 5.32 (d, J=5.0 Hz, 1H, β-lactam-H); 5.92 (dd, J=5.0 and 7.9 Hz, 1H, β-lactam-H); 6.83 (s, 1H, CH thiazol); 6.8–6.9 (m, 1H, CH aromatic); 7.1–7.2 (m, 1H, CH aromatic); 7.3–7.4 (m, 1H, CH aromatic); 8.23 (s, 1H, CH=N); 8.37 (2H, NH/OH); 8.51 (s, 1H, CH=N); 9.78 (d, J=7.9 Hz, 1H, NH); 12.27 (s, 1H, OH).

127 (300 MHz, DMSO-$d_6$): 3.53 and 4.49 (AB quartet, J=18.1 Hz, 2H, S—CH$_2$); 5.29 (d, J=5.0 Hz, 1H, β-lactam-H); 5.89 (dd, J=5.0 and 7.9 Hz, 1H, β-lactam-H); 6.79 (s, 1H, CH thiazol); 7.93 (broad, 2H, NH); 8.37 (broad, 1H, CH=N); 9.73 (d, J=7.8 Hz, 1H, NH); 12.15 (s, 1H, OH).

128 (300 MHz, DMSO-$d_6$): 3.25 (broad, 4H, N—CH$_2$); 3.31 (s, 3H, N—CH$_2$); 3.62 and 4.27 (AB quartet, J=18.0 Hz, 2H, S—CH$_2$); 3.74 (broad, 4H, N—CH$_2$); 5.30 (d, J=5.0 Hz, 1H, β-lactam-H); 5.89 (dd, J=4.9 and 7.9 Hz, 1H, β-lactam-H); 6.79 (s, 1H, CH thiazol); 8.11 (s, 1H, CH=N); 9.03 (broad, 1H, NH); 9.31 (broad, 1H, NH); 9.67 (d, J=7.9 Hz, 1H, NH); 9.87 (s, 2H, NH); 12.07 (s, 1H, OH).

129 (300 MHz, DMSO-$d_6$): 0.70 (m; 4H, —CH$_2$—CH$_2$—); 3.05 (m, 1H); 3.51 and 4.49 (AB quartet, J=18 Hz, 2H, SCH$_2$); 4.38 (s, 3H, O—CH$_3$); 5.24 (d, J=4.9 Hz,1H, β-lactam-H); 5.84 (dd, J=7.9 Hz and 4.9 Hz, 1H, β-lactam-H); 6.86 (s, 1H, thiazolyl-H); 8.19 (d, J=3.9 Hz, 1H); 8.21(s, 1H, CH=N); 9.72 (d, J=8.0 Hz, 1H, NH);11.58 (s, 1H).

130 (300 MHz, CD$_3$CN+D$_2$O): 1.26 (t, J=7 Hz, 3H); 1.68 (sextet, J=7 Hz, 2H); 1.93 (quintet, J=7 Hz, 2H); 3.93 (t, J=7.1 Hz, 2H); 3.95 (s, 3H, O—CH$_3$); 3.98 and 4.57 (AB quartet, J=18 Hz, 2H, SCH$_2$); 5.59 (d, J=4.9 Hz, 1H, β-lactam-H); 6.18 (d, J=4.9 Hz, 1H, β-lactam-H); 7.40 (s, 1H, thiazolyl-H); 8.63 (s, 1H, CH=N).

131 (300 MHz, D$_2$O): 0.74 (m, 2H); 0.88 (m, 2H); 2.58 and 2.38 (two singulets, 3H, SCH$_3$); 2.68 (m, 1H); 3.45 and 3.94 (AB-system, broad, 2H, SCH$_2$); 3.95 (s, 3H, O—CH$_3$); 5.23 (d, J=4.7 Hz, 1H, β-lactam-H); 5.75 (d, J=4.7 Hz, 1H, β-lactam-H); 7.03 (s, 1H, thiazolyl-H); 8.36 (s, broad, 1H, CH=N).

132 (300 MHz, D$_2$O): 0.82 (t, J=7.3 Hz, 3H); 1.29 (sextet, J=7 Hz, 2H); 1.56 (quintet, J=7 Hz, 2H); 2.61 and 2.46 (two singulets, 3H, SCH$_3$); 3.46 (t, J=7.1 Hz, 2H); 3.55 and 4.01 (AB quartet, J=18 Hz, 2H, SCH$_2$); 3.98 (s, 3H, O—CH$_3$); 5.25 (d, J=4.9 Hz, 1H, β-lactam-H); 5.78 (d, J=4.9 Hz, 1H, β-lactam-H); 7.05 (s, 1H, thiazolyl-H); 8.39 (s, 1H, CH=N).

133 (300 MHz, DMSO-$d_6$): 2.68 (m, 2H); 3.73 (m, 2H); 3.57 and 4.23 (AB quartet, J=18 Hz, 2H, SCH$_2$); 3.96 (s, 3H, O—CH$_3$); 5.29 (d, J=4.9 Hz, 1H, β-lactam-H); 8.48 (dd, J=8 Hz and J=4.9 Hz, 1H, β-lactam-H); 6.91 (s, 1H, thiazolyl-H); 8.24 (s, 1H, CH=N); 9.20 (s, 1H); 9.90 (d, J=8.0 Hz, 1H NH).

134 (300 MHz, DMSO-$d_6$+D$_2$O): 0.68 (m, 2H); 0.84 (m, 2H), 2.91 (m, 1H); 3.62 and 4.22 (AB quartet, J=18 Hz, 2H, SCH$_2$); 5.28 (d, J=4.9 Hz, 1H, β-lactam-H); 5.85 (d, J=4.8 Hz, 1H, β-lactam-H); 7.06 (s, 1H, thiazolyl-H); 8.23 (s, 1H, CH=N).

135 (300 MHz, DMSO-$d_6$): 0.89 (t, J=7 Hz, 3H); 1.29 (sextet, J=7 Hz, 2H); 1.54 (quintet, J=7 Hz, 2H); 3.51 and 4.47 (AB quartet, J=18 Hz, 2H, SCH$_2$); 3.52 (m, 2H); 5.24 (d, J=4.8 Hz, 1H, β-lactam-H); 5.85 (dd, J=7.9 Hz and 4.8 Hz, 1H, β-lactam-H); 6.69 (s, 1H, thiazolyl-H); 8.21 (s, 1H, CH=N); 8.47 (m, 1H); 9.55 (d, J=7.9 Hz, 1H, NH); 11.44 (s, 1H); 11.54 (s, 1H).

136 (300 MHz, DMSO-$d_6$): 2.77 (s,3H, NCH$_3$); 3.0–3.2 (m, 4H); 3.35–3.6 (m, 4H); 3.63 and 4.03 (AB quartet, J=18 Hz, 2H, SCH$_2$); 3.95 (s, 3H, OCH$_3$); 5.26 (d, J=4.9 Hz, 1H, β-lactam-H); 5.84 (dd, J=7.9 Hz and J=4.9 Hz, 1H, β-lactam-H); 6.85 (s, 1H, thiazolyl-H); 8.40 (s, 1H, CH=N); 9.69 (d, J=8.0 Hz, 1H, NH); 11.67 (s, 1H).

137 (300 MHz, DMSO-$d_6$): 3.59 and 4.54 (AB quartet, J=18.2 Hz, 2H, SCH$_2$); 3.66 (d, J=4 Hz, 3 H, NHC$\underline{H}_3$); 3.95 (s, 3 H, O—CH$_3$); 5.26 (d, J=5 Hz, 1 H, β-lactam-H); 5.85 (dd, J=5 Hz and 8 Hz, β-lactam-H); 6.95 (s, 1 H, thiazolyl-H); 7.96 (s, 1 H, CH=N); 8.4 (d, J=4 Hz, N$\underline{H}$CH$_3$); 9.84 (d, J=8 Hz, NH).

138 (300 MHz, DMSO-$d_6$): 1.43 (s, 9H, —OC(CH$_3$)$_3$); 3.62 and 4.02 (AB quartet, J=17.8 Hz, 2H, SCH$_2$); 5.25 (d, J=4.9 Hz, 1H, β-lactam-H); 5.83 (dd, J=4.9 and 8.0 Hz, 1H, β-lactam-H); 6.93 (s, 1H, thiazolyl-H); 8.20 (s, 1H, CH=N); 9.69 (d, J=8.0 Hz, 1H, NH).

139 (300 MHz, DMSO-$d_6$): 3.21 (broad singulet, 4 H); 3.89 (broad singulet, 4 H); 3.50 and 4.53 (AB quartet, J=18.1 Hz, 2H, SCH$_2$); 5.27 (d, J=5 Hz, 1 H, β-lactam-H); 5.77 (d, J=58 Hz, 2H, —CH$_2$F); 5.90 (dd, J=5 Hz and 8.2 Hz, β-lactam-H); 8.66 (s, 1 H, CH=N); 9.85 (d, J=8.2 Hz, NH).

140 (300 MHZ, DMSO-$d_6$): 1.02 (t, J=7.4 Hz, 3H, C—CH$_3$); 2.32 (qd, J=7.4 and 7.5 Hz, 2H, C=C—CH$_2$—C); 3.52 and 4.15 (AB, J=17.7 Hz, 2H, S—CH$_2$); 5.17 (d, J=5.2 Hz, 1H, β-lactam-H); 5.73 (dd, J=5.2 and 8.8 Hz, 1H, β-lactam-H); 6.48 (s, 1H, CH thiazol); 6.61 (t, J=7.5 Hz, 1H, C=CH—C); 8.93 (s, 1H, CH=N); 9.14 (d, J=8.8 Hz, 1H, NH).

141 (90 MHz, DMSO-$d_6$): 2.3 (s, 3 H, CH$_3$); 1.8 to 2.1 (m, 1 H); 3.95 (s, 2H, SCH$_2$); 3.9 (s, 3 H, O—CH$_3$); 5.35 (d, J=5 Hz, 1 H, β-lactam-H); 5.9 (dd, J=5 Hz and 8 Hz, β-lactam-H); 6.95 (s, 1 H, thiazolyl-H); 8.65 (s, 1 H, CH=N); 9.9 (d, J=8 Hz, NH).

142 (90 MHz, DMSO-d$_6$): 2.3 (s, 3 H, thiazolyl-CH$_3$); 4.0 (s, 3 H, O—CH$_3$); 3.75 and 4.3 (AB quartet, J=18 Hz, 2H, SCH$_2$); 5.4 (d, J=5 Hz, 1 H, β-lactam-H); 5.95 (dd, J=5 Hz and 8 Hz, β-lactam-H); 6.7 (s, 1 H, thiazolyl-H); 7.05 (s, 1 H, thiazolyl-H); 8.55 (s, 1 H, CH═N); 9.95 (d, J=8 Hz, NH).

143 (90 MHz, DMSO-d$_6$): 2.25 (s, 3 H, thiazolyl-CH$_3$); 3.60 (s, 3 H, N—CH$_3$); 3.7 and 4.15 (AB quartet, J=18 Hz, 2H, SCH$_2$); 3.95 (s, 3 H, O—CH$_3$); 5.35 (d, J=5 Hz, 1 H, β-lactam-H); 5.85 (dd, J=5 Hz and 8 Hz, β-lactam-H); 6.7 (s, 1 H, thiazolyl-H); 7.02 (s, 1 H, thiazolyl-H); 8.15 (s, 1 H, CH═N); 9.95 (d, J=8 Hz, NH).

144 (300 MHz, DMSO-d$_6$): 2.83 (d, 3H, NCH$_3$); 3.55 and 4.23 (AB quartet, J=19.8 Hz, 2H, SCH$_2$); 3.84 (s, 3H, ═N—OCH$_3$); 5.21 (d, J=5.5 Hz, 1H, β-lactam-H); 5.70 (dd, J=5.5 Hz and 9 Hz, β-lactam-H); 6.77 (s, 1H, thiazolyl-H); 9.28 (s, 1 H, CH═N); 9.63 (d, J=9 Hz, 1H, NH).

145 (300 MHz, DMSO-d$_6$):

Diastereomer A: 1.25 (d, J=6 Hz, 3H); 1.24 (d, J=6 Hz, 3H); 1.53 (d, J=5.4 Hz, 3H, —O(CH$_3$)CH—O—); 2.9 (d, J=4.9 Hz, 3H, NCH$_3$); 3.62 and 4.61 (AB quartet, J=18.3 Hz, 2H, SCH$_2$); 3.94 (s, 3H, ═N—OCH$_3$); 4.75 to 4.84 (m, 1 H, —O—CH(CH$_3$)$_2$); 5.34 (d, J=5 Hz, 1H, β-lactam-H); 5.94 (dd, J=5 Hz and 7.8 Hz, β-lactam-H); 6.9 (q, J=5.3 Hz, 1 H, —O(CH$_3$)CH—O—); 6.92 (s, 1 H, thiazolyl-H); 8.3 (s, 1 H, CH═N); 9.96 (d, J=7.8 Hz, 1H, NH).

Diastereomer B: 1.24 (d, J=6 Hz, 3H); 1.22 (d, J=6 Hz, 3H); 1.51 (d, J=5.5 Hz, 3H, —O(CH$_3$)CH—O—); 2.9 (d, J=4.9 Hz, 3H, NCH$_3$); 3.60 and 4.65 (AB quartet, J=18.3 Hz, 2H, SCH$_2$); 3.93 (s, 3H, ═N—OCH$_3$); 4.75 to 4.84 (m, 1 H, —O—CH(CH$_3$)$_2$); 5.30 (d, J=5 Hz, 1H, β-lactam-H); 6.04 (dd, J=5 Hz and 7.6 Hz, β-lactam-H); 6.8 (q, J=5.3, 1 H,—O(CH$_3$)CH—O—); 6.92 (s, 1 H, thiazolyl-H); 8.14 (s, 1 H, CH═N); 9.95 (d, J=7.6 Hz, 1H, NH).

146 (300 MHz, DMSO-d$_6$):

Diastereomer A: 1.25 (d, J=6 Hz, 6H); 1.50 (d, J=5.4 Hz, 3H, —O(CH$_3$)CH—O—); 2.18 (s, 3H, CH$_3$CO); 3.76 and 4.48 (AB quartet, J=17.9 Hz, 2H, SCH$_2$); 4.7 to 4.9 (m, 1 H, —O—CH(CH$_3$)$_2$); 5.31(d, J=4.8 Hz, 1H, β-lactam-H); 5.88 (dd, J=4.8 Hz and 7.6 Hz, β-lactam-H); 6.87 (q, J=5.3 Hz, 1 H, —O(CH$_3$)CH—O—); 7.1 (s, 1 H, thiazolyl-H); 8.28 (s, 1 H, CH═N); 9.93 (d, J=7.6 Hz, 1H, NH).

Diastereomer B: 1.23 (d, J=6 Hz, 6H); 1.49 (d, J=5.4 Hz, 3H, —O(CH$_3$)CH—O—); 2.17 (s, 3H, CH$_3$CO); 3.70 and 4.38 (AB quartet, J=18 Hz, 2H, SCH$_2$); 4.7 to 4.9 (m, 1 H, —O—CH(CH$_3$)$_2$); 5.28 (d, J=4.8 Hz, 1H, β-lactam-H); 5.83 (dd, J=4.8 Hz and 7.6 Hz, β-lactam-H); 6.80 (q, J=5.2, 1 H,—O(CH$_3$)CH—O—); 7.1 (s, 1 H, thiazolyl-H); 8.18 (s, 1 H, CH═O); 9.91 (d, J=7.6 Hz, 1H, NH).

147 (300 MHz, DMSO-d$_6$)

Diastereomer A: 1.26 (d, J=6.2 Hz, 6H); 1.53 (d, J=5 Hz, 3H, —O(CH$_3$)CH—O—); 2.29 (s, 6H, 2 aryl-CH$_3$); 3.60 and 4.54 (AB quartet, J=18.5 Hz, 2H, SCH$_2$); 4.75 to 4.84 (m, 1 H, —O—CH(CH$_3$)$_2$); 5.34 (d, J=5 Hz, 1H, β-lactam-H); 5.97 (dd, J=5 Hz and 7.7 Hz, β-lactam-H); 6.91 (q, J=5.3 Hz, 1 H, —O(CH$_3$)CH—O—); 6.92 (s, 1 H, thiazolyl-H); 7.12 and 7.49 (AB quartet, J=8 Hz, 2×4 aromatic-H); 8.34 (s, 1 H, CH═N); 9.69 (d, J=7.7 Hz, 1H, NH).

Diastereomer B: 1.24 (d, J=6.2 Hz, 6H); 1.52 (d, J=5.5 Hz, 3H, —O(CH$_3$)CH—O—); 2.29 (3. 6 H, 2 Aryl-CH$_3$); 3.59 and 4.51 (AB quartet, J=18.4 Hz, 2H, SCH$_2$); 4.75 to 4.84 (m, 1 H, —O—CH(CH$_3$)$_2$); 5.31 (d, J=5 Hz, 1H, β-lactam-H); 5.93 (dd, J=5 Hz and 7.7 Hz, β-lactam-H); 6.83 (q, J=5.3, 1 H,—O(CH$_3$)CH—O—); 6.84 (s, 1 H, thiazolyl-H); 7.12 and 7.49 (AB quartet, J=8 Hz, 2×4 aromatic-H); 8.24 (s, 1 H, CH═N); 9.69 (d, J=7.7 Hz, 1H, NH).

A) a) (D$_2$O+DCl): 3.62 (AB quartet, J=16 Hz, 2H, S—CH$_2$); 5.10 (2d, J=5 Hz, 2H, β-lactam-H); 6.20 (s, broad, 1H, O—CH—O).

A) c) (DMSO-d$_6$): 3.55 and 3.73 (AB quartet, J=18 Hz) resp. 3.70 (s), (2H, S—CH$_2$); 3.87 (s, 3H, N—O—CH$_3$), 5.11 (d, J=5 Hz, β-lactam-H); 5.87 (m, 1H, β-lactam-H); 6.20 resp. 6.26 (s, 1H, O—CH—O); 6.77 resp. 6.78 (s, 1H, thiazolyl-H);7.27–7.35 (m, 15H, Ar—); 9.6 (s, broad, 1H, NH-thiazolyl); 9.72 resp. 9.74 (d, J=8 Hz, 1H, NH).

A) d) (DMSO-d$_6$): 3.58 and 3.76 (AB quartet, J=18 Hz) resp. 3.72 (s), (2H, S—CH$_2$); 3.88 (s, 3H, N—O—CH$_3$), 5.15 (d, J=5 Hz, β-lactam-H); 5.94 (dd, J=8 Hz and 5 Hz, 1H, β-lactam-H); 6.21 resp. 6.28 (s, 1H, O—CH—O); 6.81 resp. 6.82 (s, 1H, thiazolyl-H); 9.77 resp. 9.78 (d, J=8 Hz, 1H, NH).

B) c) (CDCl$_3$): 3.2–3,5 (m, 2H, S—CH$_2$); 5.05 (d, J=5 Hz, β-lactam-H); 6.0 (dd, J=5 and 8 Hz, 1H, β-lactam-H); 6.4 (s, 1H, O—CH—O); 7–7.4 (m, 30H, Ar—H).

B) d) (DMSO-d$_6$): 3.72 (m, 2H, S—CH$_2$); 5.15 (d, J=5 Hz, β-lactam-H); 5.95 (dd,J=8 Hz and 5 Hz, 1H, β-lactam-H); 6.3 (broad s, 1H, O—CH—O); 6.8 (s, 1H, thiazolyl-H); 9.75 (d,J=8 Hz, 1H, NH).

C) (300 MHz, DMSO-d$_6$): 3.55 and 3.77 (AB quartet, J=18 Hz) resp. 3.71 (s), (2H, S—CH$_2$); 5.14 (d, J=5 Hz, β-lactam-H); 5.97 (m, 1H, β-lactam-H); 5,79 (d, J=55 Hz, 2H, —CH$_2$F); 6.20 resp. 6.27 (s, 1H, O—CH—O); 9.81 resp. 9.84 (d, J=8 Hz, 1H, NH).

D) (300 MHz, DMSO-d$_6$): 2.20 resp. 2.21 (s, 3H, O═C—CH$_3$); 3.63 and 3.80 (AB quartet, J=18 Hz) resp. 3.76 (s) (2H, S—CH$_2$); 5.20 (d, J=5 Hz, 1H, β-lactam-H); 6.00 (dd, J=8 Hz and 5 Hz, 1H, β-lactam-H); 6.23 resp. 6.29 (s, 1H, O—CH—O); 7.16 resp. 7.17 (s, 1H, CH thiazol); 10.04 resp. 10.05 (d, J=8 Hz, 1H, NH).

E) (300 MHz, DMSO-d$_6$): 3.58 and 3.79 (AB quartet, J=18.2 Hz) resp. 3.75 (s) (2H, S—CH$_2$); 5.17 (d, J=5 Hz, 1H, β-lactam-H); 5.94 (dd, J=8 Hz and 5 Hz, 1H, β-lactam-H); 6.21 resp. 6.28 (s, 1H, O—CH—O); 6.85 resp. 6.86 (s, 1H, CH thiazol); 9.74 (d, J=8 Hz, 1H, NH); 12.38 (s, 1H, OH).

F) c) (300 MHz, DMSO-d$_6$): 1.4 (2s, 6H, C—(CH$_3$)$_2$); 1.5 (s, 9H, C—(CH$_3$)$_3$);3.6 and 3.7 (AB quartet, J=18 Hz) resp. 3.7 (s) (2H, S—CH$_2$); 5.2 (d, J=5 Hz, 1H, β-lactam-H); 5.9 (dd, J=8 Hz and 5 Hz, 1H, β-lactam-H); 6.2 resp. 6.3 (s, 1H, O—CH—O); 6.8 (s, 1H, CH thiazol); 7.2–7.5 (m, 15H, CH aromatic); 9.6 (d, J=8 Hz, 1H, NH).

F) d) (300 MHz DMSO-d$_6$): 1.48 resp. 1.50 (s, 6H, C—(CH$_3$)$_2$); 3.60 and 3.77 (AB quartet, J=18 Hz) resp. 3.74 (s) (2H, S—CH$_2$); 5.19 (d, J=5.2 Hz, 1H, 6-lactam-H); 6.01 (dd, J=8.5 Hz and 5.2 Hz, 1H, β-lactam-H); 6.23 resp. 6.29 (s, 1H, O—CH—O); 6.87 resp. 6.88 (s, 1H, CH thiazol); 9.67 (d, J=8.5 Hz, 1H, NH).

G) (300 MHz, DMSO-d$_6$): 1.00 (t, J=7.5 Hz, 3H, C—CH$_3$); 1.47 (s, 9H,O—C(—CH$_3$)$_3$); 2.27 (qd, J=7.5 Hz, 2H, C═C—CH$_2$—C); 3.57 and 3.74 (AB quartet, J=18.3 Hz) resp. 3.73 (s) (2H, S—CH$_2$); 5.11 (d, J=5.1 Hz, 1H, β-lactam-H); 5.88 (dd, J=8.5 Hz and 5.1 Hz, 1H, β-lactam-H); 6.22 resp. 6.26 (s, 1H, O—CH—O); 6.56 (t, J=7.5 Hz, 1H, C═CH—C); 7.05 (s, 1H, CH thiazol); 8.80 resp. 8.81 (d, J=8.4 Hz, 1H, NH).

H) a) (300 MHz, DMSO-d$_6$): 2.7 (s, 3H, S—CH$_3$); 3.5–3.6 (m, 4H, N—CH$_2$); 3.7–3.8 (m, 2H, N—CH$_2$); 3.8–3.9 (m, 2H, N—CH$_2$); 8.1 (s, 1H, CH═O); 9.6 (broad, 2H, NH).

H) b) (300 MHz, DMSO-d$_6$): 3.42 (s, 4H, N—CH$_2$); 3.4–3.6 (m, 4H, N—CH$_2$); 4.8 (broad, 2H, NH); 7.9 (broad, 2H, NH); 8.1 (s, 1H, CH═O); 9.5 (broad, 1H, NH).

H) c) (300 MHz, DMSO-d₆): 3.1–3.2 (s, 4H, N—CH₂); 3.7–3.8 (m, 4H, N—CH₂); 4.8 (broad, 2H, NH); 8.0 (broad, 2H, NH); 9.6 (broad, 1H, NH); 10.0 (broad, 2H, NH).

I) (90 MHz, D₂O): 1.2 ppm (t, 3H); 1.9–2.1 ppm (m, 4H); 3.3–3.7 ppm (m, 6H).

J) (90 MHz, DMSO-d₆): 2.9 ppm (d, J=5 Hz, 3H, NCH₃), 3.4–3.8 ppm (m, 8H), 7.55 ppm (broad quartet, 1 H, NH).

K) (90 MHz, D₂O): 1.3 ppm (s, 9H).

L) (90 MHz, DMSO-d₆+D₂O): 2.8 ppm (s, 3H, NCH₃); 3.4–3.65 ppm (m, 4H); 4.0–4.4 ppm (m, 4H).

M) (300 MHz, DMSO-d₆): 2.74 (s, 3H, C=N—CH₃); 3.15 (s, 9H, N(CH₃)₃); 3.49 (m broad, 2H, N—CH₂); 3.64 (m broad, 2H, N—CH₂); 4.8 (broad, 2H, NH); 7.8 (broad, 3H, NH).

N) (90 MHz, DMSO-d₆): 2.85 ppm (s, 3H, NCH₃); 3.2–3.65 ppm (m, 8H); 8.1 ppm (s, 1H, CH=O).

O) (90 MHz, DMSO-d₆+D₂O): 2.85 ppm (s, 3H, NCH₃); 3.2–3.5 ppm (m, 4H); 3.5–3.9 ppm (m, 4H).

P) (300 MHz, D₂O): 2.84 (s, 3H, N—CH₃); 3.3–3.4 (m, 2H, N—CH₂); 3.7–3.8 (m, 2H, N—CH₂).

Q) a) (90 MHz, DMSO-d₆): 2.65 ppm (s, 3H, S—CH₃); 3.35 ppm (s, 6H, NCH₃)₂); 3.65–4.0 ppm (m, 4H); 4.0–4.3 ppm (m, 4H), 9.45 ppm (broad singulet, 1H, NH).

Q) b) (90 MHz, DMSO-d₆): 3.3 ppm (s, 6H, NCH₃)₂); 3.5–3.8 ppm (m, 4H); 3.8–4.2 ppm (m, 4H).

R) a) (90 MHz, DMSO-d₆): 2.55 ppm (s, 3H, SCH₃); 3.45 ppm (s, 3H, NCH₃).

R) b) (90 MHz, DMSO-d₆): 3.15 ppm (s, 3H, NCH₃); 3.2–3.28 ppm (m, 2H); 3.28–3.35 ppm (m, 2H); 3.4–3.55 ppm (m, 4H); 5.18 ppm (broad singulet, 2H); 8.05 (s, 1H, —CH=O); 8.1–8.3 (broad singulet, 2H).

R) c) (300 MHz, DMSO-d₆): 3.16 ppm (m, 3+4 H); 3.63 ppm (m, 4H); 6.7 ppm (broad singulet, 5H); 8.5 (broad singulet, 1H); 10.0 ppm (broad singulet, 2H).

S) (300 MHz, DMSO d₆): 2.55 (s, 2H, N—CH₂); 5.92 (s, 2H, NH).

T) (300 MHz, DMSO d₆): 0.5 (m, 2H, CH₂); 0.7–0.8 (m, 2H, CH₂); 2.4–2.5 (m, 1H, N—CH); 4.7 (broad, 2H, NH); 7.5 (broad, 2H, NH); 8.2 (broad, 1H, NH); 8.9 (broad, 1H, NH).

U) (300 MHz, DMSO d₆): 2.7 (s, 3H, N—CH₃); 4.7 (broad, 2H, NH); 7.7 (broad, 1H, NH); 9.2 (broad, 1H, NH/OH); 9.8 (broad, 1H, NH/OH).

V) (300 MHz, DMSO d₆): 2.79 (d, J=4.8 Hz 6H, N(CH₃)₂); 3.20 (s, 3H, N—CH₃); 3.2 (m, 2H, N—CH₂); 3.6 (m, 2H, N—CH₂); 4.7 (very broad, 2H, NH); 7.7 (broad, 2H, NH); 10.4 (broad, 1H, NH).

W) (300 MHz, D₂O): 6.75–6.85 (m, 1H, CH aromatic); 6.9–7.0 (m, 1H, CH aromatic); 7.1–7.15 (m, 1H, CH aromatic); 7.7 (s, 1H, CH=N).

X) (300 MHz, D₂O): 2.0 (m, 1H), 2.47, 2.35 (s, s, together 3H, —SCH₃); 0.84 (m, 2H); 0.69 (m, 2H).

Y) (300 MHz, D₂O): 3.36 (t, J=7 Hz, 2H); 2.51, 2.43 (s, s, together 3H, —SCH₃); 1.55 (quintet, J=7 Hz, 2H); 1.29 (sextet, J=7 Hz, 2H); 0.85 (t, J=7 Hz, 3H).

Z) (90 MHz, DMSO-d₆): 3.65 ppm (s, 3H, NCH₃).

AA) a) (300 MHz, DMSO d₆): 2.19 (s, 3H, C—CH₃); 3.84 (s, 3H, N—CH₃); 5.84 (d, J=3.8 Hz 1H, C=CH); 6.58 (d, J=3.8 Hz 1 Hz, C=CH); 8.76 (s, 1H, NH); 8.93 (s, 1H, NH).

AA) b) (300 MHz, DMSO d₆): 2.3 (s, 3H, C—CH₃); 2.75 (s, 3H, S—CH₃); 3.65 (s, 3H, N—CH₃); 6.2 (d, J=4 Hz 1H, C=CH); 7.1 (d, J=4 Hz 1 Hz, C=CH); 10.6 (s, broad 5H, NH).

AA) c) (300 MHz, DMSO d₆): 2.2 (s, 3H, C—CH₃); 3.1 (s, 3H, N—CH₃); 5.95 (d, J=4 Hz 1H, C=CH); 6.5 (d, J=4 Hz 1 Hz, C=CH); 7.2 (very broad 5H, NH).

AB) (300 MHz, DMSO d₆/D₂O): 6.75–6.85 (m, 1H, CH aromatic); 7.00–7.05 (m, 1H, CH aromatic); 7.05–7.10 (m, 1H, CH aromatic).

AC) (300 MHz, DMSO d₆/D₂O): 8.24 (s, 1H, CH=N); 5.20 (d, J=5.2 Hz, 1H, β-lactam-H); 4.07 (d, J=5.2 Hz, 1H, β-lactam-H); 3.89 and 3.61 (ABq, J=17.8 Hz, 2H, SCH₂).

AD) (300 MHz, DMSO d₆/CD₃CO₂D+CF₃COOD): 8.67 (s, 1H, CH=N); 5.38–5.40 (2d, 2H, 2β-lactam-H); 4.01 (s, 3H, CH₃—O); 3.98–4.00 (ABq, 2H, SCH₂).

AE) (300 MHz, DMSO-d₆): 8.14 (s, 1H, CH=N); 5.33 (d, J=5.6 Hz, 1H, CH); 4.80 (d, J=5.6 Hz, 1H, CH); 3.88 and 3.58 (ABq, J=17.8 Hz, 2H, SCH₂).

AF) (300 MHz, DMSO d₆): 7.96 (s, 1H, CH=N); 5.17 (d, J=5.2 Hz, 1H, CH); 5.02 (d, J=5.2 Hz, 1H, CH); 3.96 and 3.47 (ABq, J=17.7 Hz, 2H, SCH₂).

AG) (300 MHz, DMSO d₆): 8.35 (s, 1H, CH=N); 5.31 (d, J=5.1 Hz, 1H, CH); 5.14 (d, J=5.1 Hz, 1H, CH); 4.28 and 3.84 (ABq, J=17.9 Hz, SCH₂).

AH) (300 MHz, DMSO d₆): 8.41 (s, 1H, CH=N); 5.34 (d, J=5.1 Hz, 1H, CH); 5.18 (d, J=5.1 Hz, 1H, CH); 4.37 and 3.80 (ABq, J=17.9 Hz, SCH₂).

AI) (300 MHz, DMSO d₆): 8.61 (s, 1H, CH=N); 5.36 (d, J=5.1 Hz, 1H, CH); 5.18 (d, J=5.1 Hz, 1H, CH); 4.42 und 3.71 (ABq, J=18.0 Hz, SCH₂); 2.74 (s, 3H, SCH₃).

AJ) (300 MHz, DMSO d₆): 8.52 (s, 1H, CH=N); 5.36 (d, J=5.1 Hz, 1H, CH); 5.21 (d, J=5.1 Hz, 1H, CH); 4.46 and 3.79 (ABq, J=17.7 Hz, 2H, SCH₂); 2.95 (s, 3H, N—CH₃).

AK) (300 MHz, DMSO d₆): 8.51 (s, 1H, CH=N); 7.56–6.84 (m, 10H, 2Ph); 5.28 (d, J=4.8 Hz, 1H, CH); 5.00 (d, J=5.1 Hz, 1H, CH); 4.13 and 3.93 (ABq, J=16.8 Hz, 2H, SCH₂).

What is claimed is:

1. A compound of the formula

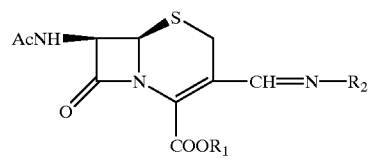

I in free form, in salt form, or in solvate form wherein

R₁ is hydrogen or selected from the group consisting of alkyl, arylalkyl, indanyl, phthalidyl, alkoxymethyl, $(C_{1-6})$alkanoyloxy$(C_{1-6})$alkyl, $(C_{1-6})$alkoxycarbonyloxy$(C_{1-6})$alkyl, glycyloxymethyl, phenylglycyloxymethyl, and (5-methyl-2-oxo-1,3-dioxolen-4-yl)methyl;

R₂ is a group of the formula

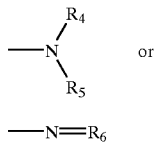

IIb or

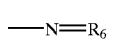

IIc wherein

R₄ is hydrogen, alkyl, alkenyl, cycloalkyl, aryl, $C_{(1-12)}$ acyl, or unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl;

$R_5$ is hydrogen, alkyl, alkenyl, cycloalkyl, aryl, unsaturated or saturated heterocyclyl having 5 or 6 ring members and 1 to 3 hetero atoms and being unsubstituted or substituted oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl, or is a group of the formula

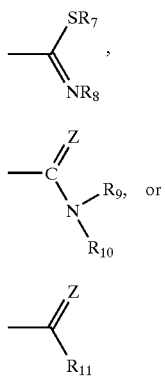

wherein
$R_7$ is alkyl or aryl;
$R_8$ is hydrogen, cycloalkyl, or alkyl;
$R_9$ is hydrogen or alkyl;
$R_{10}$ is hydrogen; unsubstituted alkyl; alkyl substituted by $CF_3$, OH, alkoxy, carboxyl, halogen, amino, monoalkylamino, dialkylamino, pyridyl, or —$SO_3H$; hydroxy; amino; phenyl; alkenyl; cycloalkyl; aryl; —N=CH-aryl wherein aryl is substituted or unsubstituted; or unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl; or $R_9$ and $R_{10}$ together with the nitrogen atom are unsaturated or saturated heterocyclyl having 5 or 6 ring members and 1 to 3 hetero atoms and being unsubstituted or substituted by $(C_{1-12})$acyl or $(C_{1-8})$alkyl;

Z is oxygen, sulphur, or N—$R_{13}$, wherein $R_{13}$ is hydrogen, alkyl, or cycloalkyl;

$R_{11}$ is hydrogen, substituted alkyl, unsubstituted alkyl, aryl, dihydroxyphenyl, cycloalkyl, or unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl; or $R_4$ and $R_5$ together with the nitrogen atom are unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl;

$R_6$ is unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl; and Ac is

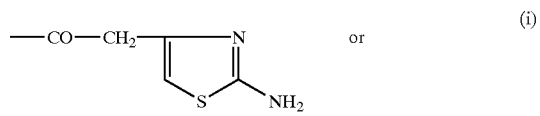

(ii) a group of the formula

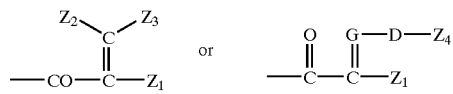

wherein
G is N or CH;
$Z_1$ is aryl, cycloalkyl, 1,4-cyclohexadienyl, or unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$ acyl, $CF_3$, CHO, alkyl, or cycloalkyl;
$Z_2$ is hydrogen, alkyl, or —$CH_2COOZ_5$, wherein $Z_5$ is hydrogen, alkyl, or cycloalkyl;

or, in the case that Ac is a group of the formula

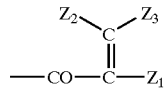

wherein
$Z_3$ is hydrogen and $Z_1$ is 2-amino-thiazol-4-yl or 5-amino-1,2,4-thiadiazol-3-yl,
$Z_2$ is hydrogen, $(C_{1-12})$acyl, carboxyl, or alkyl;
$Z_3$ is hydrogen or alkyl; and
$Z_4$ is hydrogen, lower alkyl, cycloalkyl, aralkyl, acyl, carboxyalkyl, or $Z_6CO$—, wherein $Z_6$ is hydrogen or lower alkyl;

or, in the case that Ac is a group of the formula

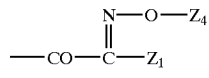

wherein
$Z_1$ is 2-amino-thiazol-4-yl or 5-amino-1,2,4-thiadiazol-3-yl;
$Z_4$ is hydrogen, $(C_{1-12})$acyl, carboxyl, or alkyl;

or, in the case that Ac is a group of the formula

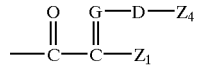

wherein
$Z_1$ is 2-amino-thiazol-4-yl or 5-amino-1,2,4-thiadiazol-3-yl, G is N or CH, and D is oxygen or $CH_2$, $Z_4$ is group of the formula

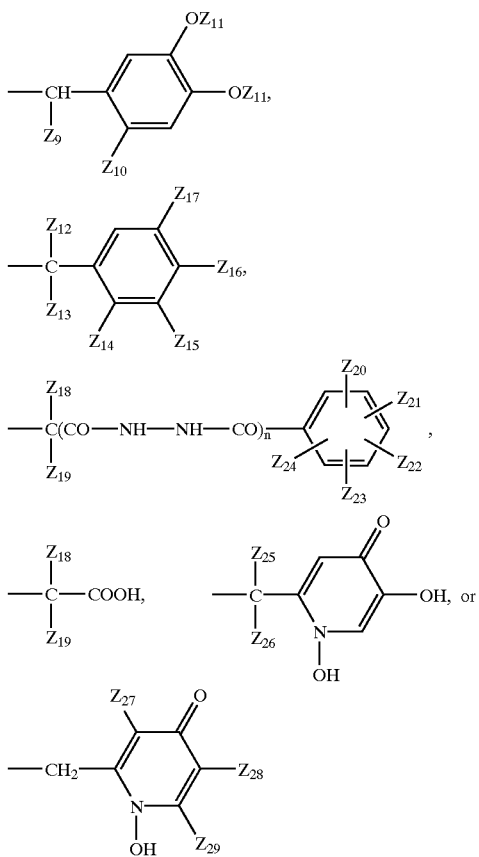

wherein
$Z_9$ and $Z_{10}$ independently of one another are hydrogen or carboxyl;
$Z_{11}$ is hydrogen or acetyl;
$Z_{12}$ is carboxyl;
$Z_{13}$ is hydrogen or methyl;
$Z_{14}$ is hydrogen, chloro, carboxyl, methyl, isopropyl, hydroxy, methoxy, or acetoxy;
$Z_{15}$ and $Z_{16}$ are independently of one another hydrogen, hydroxy, methoxy, ethoxy, 2-methoxyethoxymethoxy, acetoxy, chloroacetoxy, butanoyloxy, methansulfonyloxy, p-toluenesulfonyloxy, amino, acetylamino, benzyloxycarbonylamino, or methansulfonyl; or $Z_{15}$ and $Z_{16}$ are together ethylendioxy or carbonyldioxy;
$Z_{17}$ is hydrogen, hydroxy, acetoxy, methyl, methoxy, or chloroacetoxy;
with the proviso that not all of $Z_{14}$, $Z_{15}$, $Z_{16}$, and $Z_{17}$ are hydrogen;
$Z_{18}$ and $Z_{19}$ are independently of one another hydrogen or methyl;
$Z_{20}$, $Z_{21}$, $Z_{22}$, $Z_{23}$, and $Z_{24}$ are independently of one another hydrogen, halogen, or hydroxy;
$Z_{25}$ and $Z_{26}$ are independently of one another hydrogen, $(C_{1-5})$-alkyl, unsubstituted phenyl, or phenyl substituted by $(C_{1-8})$-alkyl, $(C_{1-8})$-alkoxy, $(C_{1-12})$-acyl, halogen, hydroxy, or amino;
$Z_{27}$ is unsubstituted lower alkyl or lower alkyl substituted by halogen, hydroxy, $SO_3H$, $CF_3$, pyridyl, $(C_{1-8})$-alkylamino, $(C_{1-8})$-alkoxy, or $(C_{1-12})$-acyl;
$Z_{28}$ and $Z_{29}$ are independently of one another hydrogen or hydroxy;

n is 0 or 1; and
D is oxygen or $CH_2$.

2. A compound of claim 1 of the formula

IA in free form, in salt form, or in solvate form, wherein
W is CH or N;
V is CH or N—O;
$R_1$ is hydrogen or selected from the group consisting of alkyl, arylalkyl, indanyl, phthalidyl, alkoxymethyl, $(C_{1-6})$alkanoyloxy$(C_{1-6})$alkyl, $(C_{1-6})$alkoxycarbonyloxy$(C_{1-6})$alkyl, glycyloxymethyl, phenylglycyloxymethyl, and (5-methyl-2-oxo-1,3-dioxolen-4-yl)methyl;
$R_2$ is a group of the formula IIb or IIc wherein
$R_4$ is hydrogen, phenyl, cycloalkyl, or lower alkyl;
$R_5$ is hydrogen, lower alkyl, unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl, or is a group of formula IId IIe or IIf wherein
$R_7$ is lower alkyl;
$R_8$ is hydrogen, cycloalkyl, or lower alkyl;
$R_9$ is hydrogen or lower alkyl;
$R_{10}$ is hydrogen; hydroxy; amino; phenyl; alkenyl; cycloalkyl; unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl; unsubstituted alkyl; alkyl substituted by $CF_3$, OH, alkoxy, carboxyl, halogen, amino, monoalkylamino, dialkylamino, pyridyl, or —$SO_3H$; or a group of the formula

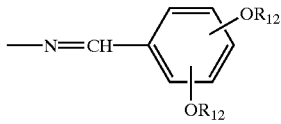

wherein
$R_{12}$ is hydrogen or lower alkyl;
Z is oxygen, sulphur, or N—$R_{13}$, wherein $R_{13}$ is hydrogen or lower alkyl; and
$R_{11}$ is hydrogen; dihydroxyphenyl; cycloalkyl; unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl; unsubstituted lower alkyl; or lower alkyl substituted by pyridyl, monoalkylamino, or dialkylamino; and
$R_4$ and $R_5$ independently of one another together with the nitrogen atom are unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl;
and/or $R_9$ and $R_{10}$ independently of one another together with the nitrogen atom are unsaturated or saturated heterocyclyl having 5 or 6 ring members and 1 to 3 hetero atoms and being unsubstituted or substituted by $(C_{1-12})$-acyl or $(C_{1-8})$-alkyl;
$R_6$ is unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$acyl, $CF_3$, CHO, alkyl, or cycloalkyl; and
$R_3$ is hydrogen, $C_{(1-12)}$acyl, carboxyl, unsubstituted alkyl, or alkyl substituted by halogen or carboxyl.

3. A compound of claim 2 of the formula

Is

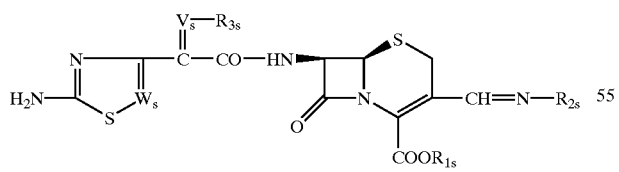

in free form, in salt form, or in solvate form, wherein
$R_{1s}$ is hydrogen or selected from the group consisting of alkyl, arylalkyl, indanyl, phthalidyl, alkoxymethyl, $(C_{1-6})$alkanoyloxy$(C_{1-6})$alkyl, $(C_{1-6})$alkoxycarbonyloxy$(C_{1-6})$alkyl, glycyloxymethyl, phenylglycyloxymethyl, and (5-methyl-2-oxo-1,3-dioxolen-4-yl)methyl;
$V_s$ is CH or N—O;
$W_s$ is CH or N;
$R_{3s}$ is hydrogen, $C_{(1-12)}$acyl, unsubstituted alkyl, or lower alkyl substituted by carboxyl and/or fluoro; and
$R_{2s}$ is a group of the formula IIbs

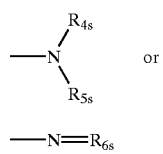

or

IIcs

—N=$R_{6s}$ wherein
$R_{4s}$ is hydrogen or lower alkyl; and
$R_{5s}$ is hydrogen, saturated or unsaturated, unsubstituted heterocyclyl having 5 or 6 ring members and 1 to 3 nitrogen hetero atoms, saturated or unsaturated one or several fold substituted heterocyclyl substituted by oxo, lower alkyl, amino, or $CF_3$, having 5 or 6 ring members and 1 to 3 nitrogen hetero atoms, benzothiazolyl, or a group of the formula IIds

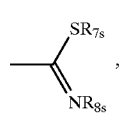

,

IIes

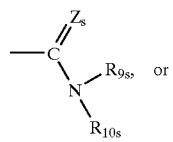 or

IIfs

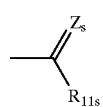

wherein
$Z_s$ is oxygen, sulphur, or $NR_{13}$, wherein $R_{13}$ is hydrogen, alkyl, or cycloalkyl;
$R_{7s}$ is lower alkyl;
$R_{8s}$ is hydrogen, cycloalkyl, or lower alkyl;
$R_{9s}$ is hydrogen or lower alkyl;
$R_{10s}$ is hydrogen, phenyl, allyl, cycloalkyl, unsubstituted alkyl, or alkyl substituted by —$CF_3$, dialkylamino, hydroxy, pyridyl, or —$SO_3H$; and
$R_{11s}$ is hydrogen, pyridyl, cycloalkyl, unsubstituted lower alkyl, lower alkyl substituted by pyridyl, saturated or unsaturated heterocyclyl having 5 or 6 ring members and 1 to 3 nitrogen hetero atoms, or one or several fold substituted heterocyclyl substituted by lower alkyl and/or =S, having 5 or 6 ring members and 1 to 3 nitrogen hetero atoms;
$R_{4s}$ and $R_{5s}$ together with the nitrogen atom are heterocyclyl selected from the group consisting of saturated, unsubstituted heterocyclyl having 5 or 6 ring members and 1 or 2 nitrogen hetero atoms, saturated, one or several fold substituted heterocyclyl substituted by oxo or lower alkyl, having 5 or 6 ring members and 1 or 2 nitrogen hetero atoms; and/or
$R_{9s}$ and $R_{10s}$ together with the nitrogen atom are saturated, unsubstituted heterocyclyl having 5 or 6 ring members and 1 or 2 nitrogen and/or oxygen hetero atoms, or unsaturated, one or several fold substituted heterocyclyl substituted by —CHO or lower alkyl, having 5 or 6 ring members and 1 or 2 nitrogen and/or oxygen hetero atoms.

4. A compound of claim 1 of the formula

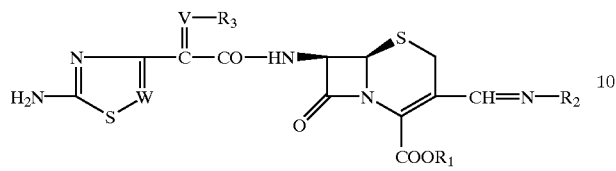

IA in free form, in salt form, or in solvate form, wherein

W is CH or N;

V is CH or N—O;

$R_1$ is hydrogen or selected from the group consisting of alkyl, arylalkyl, indanyl, phthalidyl, alkoxymethyl, $(C_{1-6})$alkanoyloxy$(C_{1-6})$alkyl, $(C_{1-6})$alkoxycarbonyloxy$(C_{1-6})$alkyl, glycyloxymethyl, phenylglycyloxymethyl, and (5-methyl-2-oxo-1,3-dioxolen-4-yl)methyl;

$R_2$ is a group of the formula

  (IIb)

wherein $R_5$ is a group of the formula

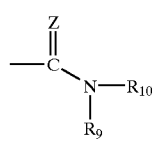

IIe wherein

Z is —N—$R_{13}$, wherein $R_{13}$ is hydrogen, alkyl, or cycloalkyl;

$R_9$ and $R_{10}$ together with the nitrogen atom are a piperazinyl; and $R_3$ is hydrogen, $(C_{1-12})$-acyl, carboxyl, unsubstituted alkyl, or alkyl substituted by halogen or carboxyl.

5. A compound of claim 1 which is

7-[[(2-amino-4-thiazolyl)-(Z)-(hydroxyimino)acetyl]amino]-3-[[(aminoiminomethyl)hydrazono]methyl]-3-cephem-4-carboxylic acid;

7-[[(2-amino-4-thiazolyl)-(Z)-(hydroxyimino)acetyl]-amino]-3-[[(piperazino-iminomethyl)hydrazono]methyl]-3-cephem-4-carboxylic acid; or 7-[[(5-amino-1,2,4-thiadiazol-3-yl)-(Z)-(fluormethoxyimino)acetyl]amino]-3-[[(piperazinoiminomethyl)hydrazono]methyl]-3-cephem-4-carboxylic acid, in free form, in salt form, or in solvate form.

6. A compound of claim 1 of the formula

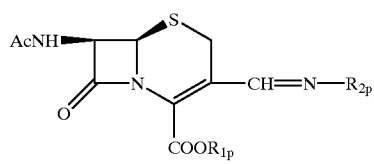

Ip wherein $R_{1p}$ is hydrogen or selected from the group consisting of alkyl, arylalkyl, indanyl, phthalidyl, alkoxymethyl, $(C_{1-6})$alkanoyloxy$(C_{1-6})$alkyl, $(C_{1-6})$alkoxycarbonyloxy$(C_{1-6})$alkyl, glycyloxymethyl, phenylglycyloxymethyl, and (5-methyl-2-oxo-1,3-dioxolen-4-yl)methyl;

$R_{2p}$ is a group of the formula

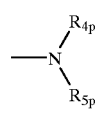

IIbp wherein $R_{4p}$ is hydrogen, phenyl, cycloalkyl, or lower alkyl; and $R_{5p}$ is hydrogen, cycloalkyl, lower alkyl, or a group of the formula

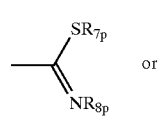

IIdp or

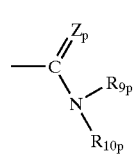

IIep wherein $R_{8p}$ is hydrogen, cycloalkyl, or lower alkyl;

$Z_p$ is oxygen, sulphur, or N—$R_{13}$, wherein $R_{13}$ is hydrogen, alkyl, or cycloalkyl;

$R_{9p}$ is hydrogen or lower alkyl;

$R_{7p}$ is methyl;

$R_{10p}$ is hydrogen, lower alkyl, or hydroxy; and $R_{4p}$ and $R_{5p}$ and/or $R_{9p}$ and $R_{10p}$ independently of one another together with the nitrogen atom are unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$ acyl, $CF_3$, CHO, alkyl, or cycloalkyl, in free form, in salt form, or in hydrate form.

7. A compound of claim 1 of the formula

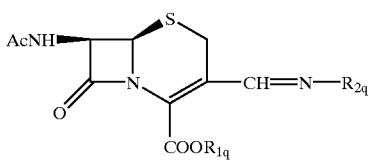

Iq wherein
$R_{1q}$ is hydrogen or selected from the group consisting of alkyl, arylalkyl, indanyl, phthalidyl, alkoxymethyl, $(C_{1-6})$alkanoyloxy$(C_{1-6})$alkyl, $(C_{1-6})$alkoxycarbonyloxy$(C_{1-6})$alkyl, glycyloxymethyl, phenylglycyloxymethyl, and (5-methyl-2-oxo-1,3-dioxolen-4-yl)methyl; and
$R_{2q}$ is a group of the formula

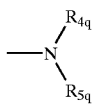

IIbq wherein
$R_{4q}$ is hydrogen, phenyl, cycloalkyl, or lower alkyl; and
$R_{5q}$ is hydrogen, cycloalkyl, lower alkyl, or a group of formula

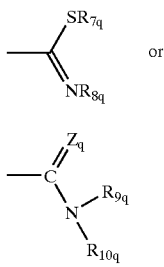

IIdq or

IIeq wherein
$R_{7q}$ is hydrogen, cycloalkyl, or lower alkyl;
$R_{8q}$ is hydrogen, cycloalkyl, or alkyl;
$Z_q$ is oxygen, sulphur, or N—$R_{13}$, wherein $R_{13}$ is hydrogen, alkyl, or cycloalkyl;
$R_{9q}$ is hydrogen or lower alkyl;
$R_{10q}$ is hydrogen, lower alkyl, or hydroxy; and
$R_{4q}$ and $R_{5q}$ and/or $R_{9q}$ and $R_{10q}$ independently of one another together with the nitrogen atom are unsaturated or saturated heterocyclyl having 5 or 6 ring members and 1 to 3 hetero atoms and being unsubstituted or substituted by oxo, alkoxy, hydroxy, =S, mercapto, alkylthio, imino, alkylamino, alkylimino, amino, halogen, $C_{(1-12)}$ acyl, $CF_3$, CHO, alkyl, or cycloalkyl,
in free form, in salt form, or in hydrate form.

8. A compound of claim 1 in free form.
9. A compound of claim 1 in salt form.
10. A compound of claim 9 in acid addition salt form.
11. A compound of claim 9 in metal salt form.
12. A compound of claim 1 in solvate form.
13. A pharmaceutical composition comprising a compound of claim 1 in pharmaceutically acceptable salt form or free form in association with at least one pharmaceutical carrier or diluent.

14. A method of treatment of bacterial diseases which comprises administering to a subject in need of such treatment an effective amount of a compound of claim 1.

15. The method of claim 14 characterized in that bacterial diseases are caused by bacteria selected from the group consisting of Pseudomonas, Enterobacter, Enterococcus, Moraxella, Haemophilus, Klebsiella, Streptococcus, Staphylococcus, Escherichia, and Proteus.

16. A process for the production of a compound of claim 1 which comprises either a) reacting a compound of the formula

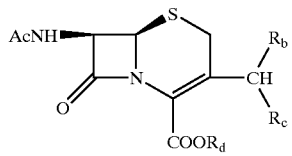

II wherein
1) $R_b$ is hydroxy and $R_c$ and $R_d$ together form a bond, or
2) $R_d$ is hydrogen, a cation, an ester forming group, or a silyl protecting group, and $R_b$ and $R_c$ together are oxo,
in free form or in the form of an acid addition salt with a group of the formula $$H_2N—R_2 \qquad (IV)$$

or b) reacting a compound of the formula

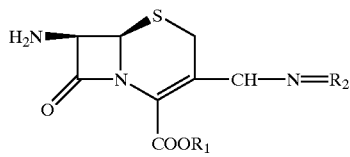

VI with a compound of the formula Ac-X' (VII) wherein X' is a leaving group.

17. A compound of the formula

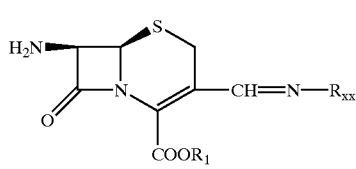

VIa wherein $R_1$ is hydrogen or selected from the group consisting of alkyl, arylalkyl, indanyl, phthalidyl, alkoxymethyl, $(C_{1-6})$alkanoyloxy$(C_{1-6})$alkyl, $(C_{1-6})$alkoxycarbonyloxy$(C_{1-6})$alkyl, glycyloxymethyl, phenylglycyloxymethyl, and (5-methyl-2-oxo-1,3-dioxolen-4-yl)methyl; and $R_{xx}$ is a group of the formula

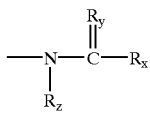

wherein
$R_x$ is a group of the formula

—NH—C(CH$_3$)$_3$, —NH—CH$_2$CF$_3$,

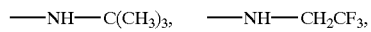

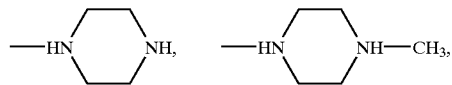

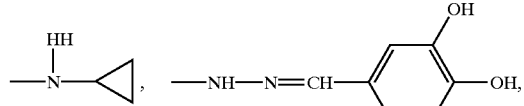

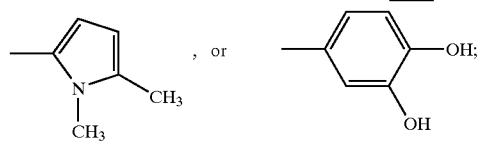

$R_y$ is NH; and
$R_z$ is hydrogen; or
$R_x$ is a group of the formula

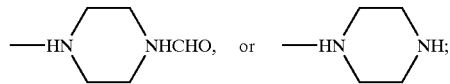

$R_y$ is NH; and
$R_z$ is CH$_3$; or
$R_x$ is —SCH$_3$;

$R_y$ is a group of the formula

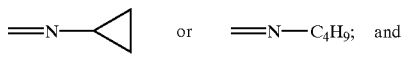

$R_z$ is hydrogen; or
$R_x$ is a group of the formula

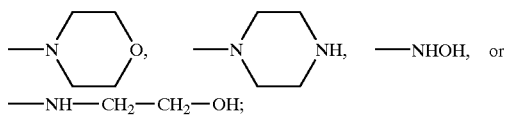

$R_y$ is N—CH$_3$; and
$R_z$ is hydrogen; or
$R_x$ is

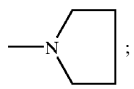

$R_y$ is N—C$_2$H$_5$; and
$R_z$ is hydrogen; or
$R_x$ is

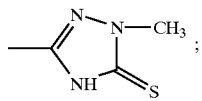

$R_y$ is oxygen; and
$R_z$ is hydrogen.

* * * * *

UNITED STATES PATENT AND TRADEMARK OFFICE
CERTIFICATE OF CORRECTION

PATENT NO. : 6,531,465 B1
DATED : March 11, 2003
INVENTOR(S) : Ascher et al.

It is certified that error appears in the above-identified patent and that said Letters Patent is hereby corrected as shown below:

<u>Title page,</u>
Item [63], should read
-- Related U.S. Application Data
[63] Continuation of 09/357,194, filed on Jul 20, 1999, abandoned, which is a continuation of 08/952,244, October 29, 1997, abandoned, which is a 371 of PCT/EP96/02023, October 5, 1996. --.

<u>Column 13,</u>
Line 40, should read -- A compound of formula IIIc may be obtained --.

<u>Column 22,</u>
Table 1, Example 15 the structural formula should read 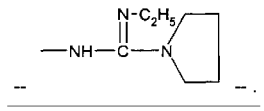 --.

<u>Column 46,</u>
Line 12, should read: -- 7H-azeto[2,1-b]furo[3,4-d] [1,3-thiazin-6-yl)-2-(2- --.

<u>Column 50,</u>
Line 36, should read -- allowed to stand for ca. 2 hours at 4°. The hydrochloride of --.

<u>Column 51,</u>
Line 43, should read -- methyliodide. The mixture is stirred at 40° under nitrogen --.

<u>Column 54,</u>
Line 60, should read -- 14 (90 MHz, DMSO-$d_6$): 3,65 (broad s, 4H, N-$CH_2$- --.
Last line should read -- $CH_2$-N-$CH_2$- and 1H of SCH); 3.91 (s, 3H, N-O- --.

<u>Column 55,</u>
Line 10, should read -- (m, 5H,-$CH_2$-N-$CH_2$- and 1H of $SCH_2$); 4.5 (part of --.
Line 14, should read -- 18 (90 MHz, DMSO-$d_6$: 2.86 (broad s, 6H, N-$CH_3$), 3); --.
Line 20, should read -- 19 (90 MHz, DMSO-$d_6$): 3.7 (broad s, 4H, N-$CH_2$)- --.
Line 55, should read -- Hz, 2H, $SCH_2$); 3.9 to 4.1 (m, 5 H, -$OCH_3$ and -N-C --.
Line 57, should read -- -N-$CH_2$-CH=$C\underline{H}_2$; 5.7 to 6.1 (m, 2H, β-lactam-H and --.

UNITED STATES PATENT AND TRADEMARK OFFICE
CERTIFICATE OF CORRECTION

PATENT NO.    : 6,531,465 B1
DATED         : March 11, 2003
INVENTOR(S)   : Ascher et al.

It is certified that error appears in the above-identified patent and that said Letters Patent is hereby corrected as shown below:

<u>Column 68,</u>
Line 47, should read -- (s) (2H, S-CH$_2$); 5.19 (d, J=5.2 Hz, 1H, β-lactam-H); 6.01 --.

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,531,465 B1
DATED        : March 11, 2003
INVENTOR(S)  : Ascher et al.

It is certified that error appears in the above-identified patent and that said Letters Patent is hereby corrected as shown below:

Title page,
Item [63], should read
                    -- Related U.S. Application Data
   [63]   Continuation of 09/357,194, filed on Jul 20, 1999, abandoned, which is
          a continuation of 08/952,244, October 29, 1997, abandoned, which is a
          371 of PCT/EP96/02023, May 10, 1996. --.

Column 13,
Line 40, should read -- A compound of formula IIIc may be obtained --.

Column 22,
Table 1, Example 15 the structural formula should read

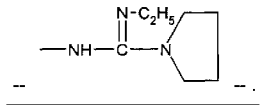

Column 46,
Line 12, should read -- 7H-azeto[2,1-b]furo[3,4-d] [1,3-thiazin-6-yl)-2-(2- --.

Column 50,
Line 36, should read -- allowed to stand for ca. 2 hours at 4°. The hydrochloride of --.

Column 51,
Line 43, should read -- methyliodide. The mixture is stirred at 40° under nitrogen --.

Column 54,
Line 60, should read -- 14 (90 MHz, DMSO-$d_6$): 3,65 (broad s, 4H, N-$CH_2$- --.
Last line should read -- $CH_2$-N-$CH_2$- and 1H of SCH); 3.91 (s, 3H, N-O- --.

Column 55,
Line 10, should read -- (m, 5H,-$CH_2$-N-$CH_2$- and 1H of $SCH_2$); 4.5 (part of --.
Line 14, should read -- 18 (90 MHz, DMSO-$d_6$: 2.86 (broad s, 6H, N-$CH_3$), 3); --.
Line 20, should read -- 19 (90 MHz, DMSO-$d_6$): 3.7 (broad s, 4H, N-$CH_2$)- --.
Line 55, should read -- Hz, 2H, $SCH_2$); 3.9 to 4.1 (m, 5 H, -$OCH_3$ and -N-C --.
Line 57, should read -- -N-$CH_2$-CH=C$\underline{H}_2$; 5.7 to 6.1 (m, 2H, β-lactam-H and --.

UNITED STATES PATENT AND TRADEMARK OFFICE
CERTIFICATE OF CORRECTION

PATENT NO. : 6,531,465 B1
DATED : March 11, 2003
INVENTOR(S) : Ascher et al.

It is certified that error appears in the above-identified patent and that said Letters Patent is hereby corrected as shown below:

Column 68,
Line 47, should read -- (s) (2H, S-CH$_2$); 5.19 (d, J=5.2 Hz, 1H, β-lactam-H); 6.01 --.

This certificate supersedes Certificate of Correction issued April 6, 2004.

Signed and Sealed this

Fifth Day of October, 2004

JON W. DUDAS
*Director of the United States Patent and Trademark Office*